(12) United States Patent
Armour et al.

(10) Patent No.: US 7,041,667 B1
(45) Date of Patent: *May 9, 2006

(54) CCR5 MODULATORS

(75) Inventors: Duncan Robert Armour, Ramsgate (GB); David Anthony Price, Ringwould Deal (GB); Blanda Luzia Christa Stammen, Sandwich (GB); Anthony Wood, Margate (GB); Manoussos Perros, Ramsgate (GB); Martin Paul Edwards, Ringwould Deal (GB)

(73) Assignee: Pfizer, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/452,634

(22) Filed: Dec. 1, 1999

(30) Foreign Application Priority Data

Dec. 23, 1998 (GB) ............................................. 9828420
Sep. 25, 1999 (GB) ............................................. 9922702

(51) Int. Cl.
*A61K 31/535* (2006.01)

(52) U.S. Cl. .................... 514/235.2; 514/253; 514/256; 514/258; 514/266; 514/299; 514/303; 514/304; 514/307; 514/311; 544/127; 544/238; 544/242; 544/262; 544/263; 544/277; 544/295; 544/335; 544/336; 544/408; 546/112; 546/118; 546/119; 546/124; 546/125; 546/126; 546/139; 546/146; 546/152; 546/175; 546/176

(58) Field of Classification Search ....................... None
See application file for complete search history.

(56) References Cited

U.S. PATENT DOCUMENTS 6,586,430 B1 * 7/2003 Armour et al. .......... 514/235.2

FOREIGN PATENT DOCUMENTS

| EP | 0256181 | 2/1988 |
|---|---|---|
| EP | 0630887 | 5/1994 |
| EP | 0903349 | 3/1999 |
| WO | 9719060 | 5/1997 |
| WO | 9724325 | 7/1997 |
| WO | 9802151 | 1/1998 |
| WO | 9825604 | 6/1998 |
| WO | 9825605 | 6/1998 |
| WO | 9825617 | 6/1998 |
| WO | 9831364 | 7/1998 |
| WO | 9904794 | 2/1999 |
| WO | 9909984 | 3/1999 |
| WO | 9917773 | 4/1999 |
| WO | 9937617 | 7/1999 |
| WO | 9937619 | 7/1999 |
| WO | 9624582 | 8/1999 |

* cited by examiner

*Primary Examiner*—J. S. Parkin
(74) *Attorney, Agent, or Firm*—Keith D. Hutchinson; Bryan C. Zielinski; Peter C. Richardson

(57) ABSTRACT

Compounds of Formula 1

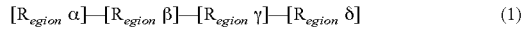

which are useful as modulators of chemokine activity. The invention also provides pharmaceutical formulations and methods of treatment using these compounds.

1 Claim, No Drawings

CCR5 MODULATORS

This application claims priority under 35 U.S.C. §119 of Great Britain applications 9828420.1 and 9922702.7, filed respectively on Dec. 23, 1998 and Sep. 25, 1999, the texts of which are hereby incorporated by reference herein in their entireties.

This invention relates to new chemical compounds. These compounds find particular but not exclusive use as pharmaceuticals, especially as CCR5 antagonists and agonists.

This invention also relates to formulations or dosage forms including these compounds, to use of these compounds in manufacture of pharmaceutical formulations or dosage forms and methods of treatment, especially treatment of anti-inflammatory diseases and conditions and in the treatment and prevention of HIV-1 and genetically related retroviral infections.

The compositions of matter of the present invention may be modulators of the activity of chemokine CCR5 receptors, particularly those which occur on the surfaces of certain cells within the human body. Modulators of CCR5 receptor activity may be useful in the treatment and prevention of various inflammatory diseases and conditions, and in the treatment and prevention of infection by HIV-1 and genetically related retroviruses.

The name "chemokine", is a contraction of "chemotactic cytokines". The chemokines comprise a large family of proteins which have in common important structural features and which have the ability to attract leukocytes. As leukocyte chemotactic factors, chemokines play an indispensable role in the attraction of leukocytes to various tissues of the body, a process which is essential for both inflammation and the body's response to infection. Because chemokines and their receptors are central to the pathophysiology of inflammatory and infectious diseases, agents which are active in modulating, for example agonising or antagonizing, the activity of chemokines and their receptors, are useful in therapeutic treatment.

The chemokine receptor CCR5 is of particular importance in the context of treating inflammatory and infectious diseases. CCR5 is a receptor for chemokines, especially for the macrophage inflammatory proteins (MIP) designated MIP-1α and MIP-1β, and for a protein which is regulated upon activation and is normal T-cell expressed and secreted (RANTES). The relationship between modulators, especially antagonists of CCR5 activity and therapeutic usefulness in treating inflammation and HIV infection, and the manner in which such a relationship may be demonstrated, is explained in more detail further below.

There is ongoing in the art a substantial investigation of different classes of modulators of chemokine receptor activity, especially that of the CCR5 chemokine receptor. A representative disclosure is Mills et al. WO 98/25617 relating to substituted aryl piperazines as modulators of chemokine receptor activity. However, the compositions described therein are not the same as, nor suggestive of those of the present invention. Further disclosures are: WO 98/025605; WO 98/025604; WO 98/002151; WO 98/004554; and WO 97/024325.

The present invention relates to compounds which may be conveniently considered to have four independently variable regions, reading from the left-hand side to right-hand side of said compound: $R_{region}$ α, $R_{region}$ β, $R_{region}$ γ, and $R_{region}$ δ, of Formula (I):

$$[R_{region}\ \alpha]-[R_{region}\ \beta]-[R_{region}\ \gamma]-[R_{region}\ \delta] \qquad (I)$$

and pharmaceutically acceptable salts and prodrug derivatives thereof. The compounds of the present invention may be selective CCR5 receptor modulators and are non-peptidyl in structure.

The compounds as exemplified by Formula (I) may contain one or more stereogenic centers and the present invention includes the recited compounds in both their separated and their unseparated forms. The separated forms can be obtained by conventional means, e.g., by asymmetric synthesis, by using high performance liquid chromatography employing a chiral stationary phase, or by chemical resolution via the formation of suitable salts or derivatives. It will be understood that the separate optically active forms of the compositions of the present invention, as well as racemic mixtures thereof, will usually vary with respect to their biological properties because of the chirality-dependent conformation of the active site of an enzyme, receptor, etc.

The description which follows provides details of the particular moieties which comprise each of said $R_{egions}$. In order to present said details in an orderly and space-saving fashion, each major group in each Region is set out with a single dash ("—"), and each successive subdivision within each said group is set out in turn with two, three, etc. dashes as required.

In this specification and claims a reference to a range or class of groups for example ($C_1$-$C_3$)alkyl is to be understood as an express disclosure and reference of each member of the range or class, including isomers.

According to the present invention there is provided a compound of Formula (I):

$$[R_{region}\ \alpha]-[R_{region}\ \beta]-[R_{region}\ \gamma]-[R_{region}\ \delta] \qquad (I)$$

wherein $[R_{region}\ \alpha]$ is selected from the group consisting of:
A. Aryl heterocyclyl substituent components comprising:
  1. hetero-phenylmethylene moieties of partial Formula (1.0.0):

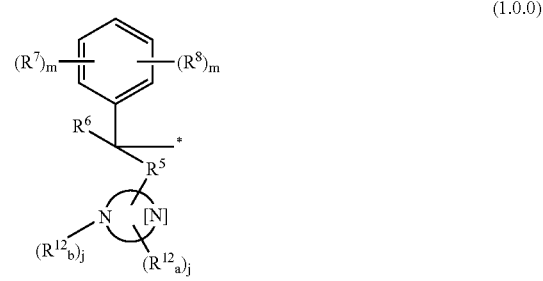

wherein: the symbol "*" indicates the point of attachment of the moiety of partial Formula (1.0.0) to $R_{region}\ \beta$, as hereinafter defined;

$R^5$ is a member selected from the group consisting of a direct bond; —O—; —C(=O)—; —NR$^4$—; and —S(=O)$_p$—; where:

$R^4$ is hydrogen or ($C_1$-$C_2$)alkyl;

$R^6$ is a member selected from the group consisting of hydrogen; ($C_1$-$C_2$)alkyl; ($C_1$-$C_2$)alkoxy; —CN; —OH; and —C(=O)NH$_2$;

j is an integer selected from 0, 1, and 2;

m is an integer selected from 0, 1, and 2;

$R_7$ and $R^8$ are each a member selected from the group consisting of —F; —Cl; —CO$_2$R$^4$; —OH; —CN; —CONR$^4{}_aR^4{}_b$; —NR$^4{}_aR^4{}_b$—; —NR$^4{}_aC(=O)R^4{}_b$; —NR$^4{}_b$; —NR$^4{}_aC(=O)OR^4{}_b$; —NR$^4{}_aS(=O)_pR^4{}_b$; —S(=O)$_p$NR$^4{}_aR^4{}_b$; ($C_1$-$C_4$)alkyl, and ($C_1$-$C_4$)alkoxy wherein said alkyl and alkoxy are each substituted with 0 to 3 substituents independently selected from F and Cl; ($C_1$-$C_2$)alkoxycarbonyl; ($C_1$-$C_2$)alkylcarbonyl; and ($C_1$-$C_2$)alkylcarbonyloxy; where:

p is an integer selected from 0, 1, and 2;

$R^4_a$ and $R^4_b$ are each independently selected from hydrogen and $(C_1-C_2)$alkyl;

the moiety represented by partial Formula (1.0.1):

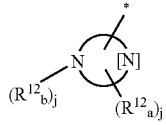

(1.0.1)

in partial Formula (1.0.0) represents a monocyclic heterocyclic group, or a bicyclic benzo-fused ring system containing said heterocyclic group wherein said heterocyclic group contains a total of 5- or 6-members of which one or two of said members is nitrogen, the presence of the optional second nitrogen atom being represented by: "[N]"; wherein said heterocyclic group or ring system are selected from the group consisting of pyrrolyl; pyrazolyl; imidazolyl; pyridinyl; pyrazinyl; pyrimidinyl; pyridazinyl; piperazinyl; indolyl; indazolinyl; benzimidazolyl; quinolinyl; isoquinolinyl; and quinazolinyl; wherein:

$R_{12a}$ is a member selected from the group consisting of hydrogen; F; Cl; $-CO_2R^4$; oxo; $-OH$; CN; $NH_2$; $NH(C_1-C_2)$alkyl; $N(C_1-C_2)_2$dialkyl; $-CF_3$; $(C_1-C_4)$alkyl; $(C_2-C_4)$alkenyl; $(C_1-C_4)$alkoxy; $(C_3-C_7)$cycloalky; and phenyl; wherein said alkyl, alkenyl, alkoxy, cycloalkyl and phenyl are substituted with 0 to 2 substituents $R^9$ where:

$R^9$ is a member independently selected from the group consisting of F; Cl; $-CO_2R^4$; $-OH$; cyano; $-CONR^4_aR^4_b$; $-NR^4_aR^4_b-$; $-NR^4_aC(=O)R^4_b$; $-NR^4_aC(=O)OR^4_b$; $-NR^4_aS(=O)_pR^4_b$; $-S(=O)_pNR^4_aR^4_b$; $(C_1-C_4)$alkyl including dimethyl, and $(C_1-C_4)$alkoxy wherein said alkyl and alkoxy are each independently substituted with 0 to 3 substituents independently selected from F and Cl; $(C_1-C_2)$alkoxycarbonyl; $(C_1-C_2)$alkylcarbonyl; and $(C_1-C_2)$alkylcarbonyloxy; and $R^{12}_b$ is absent or is a member selected from the group consisting of hydrogen; $(C_1-C_4)$alkyl; $(C_2-C_4)$alkenyl; $(C_1-C_2)$alkoxy; $(C_3-C_7)$cycloalkyl; and phenyl; wherein said alkyl, alkenyl, alkoxy, cycloalkyl and phenyl are substituted with 0 to 2 substituents $R^9$ wherein $R^9$ has the same meaning as above, except that it is selected independently selected therefrom; and 2. hetero-phenylmethylene moieties of partial Formula (1.1.0):

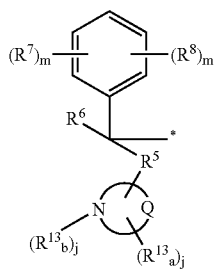

(1.1.0)

wherein: the symbol "*"; $R^5$; $R^6$; $R^7$; $R^8$; j and m are as defined further above, except that all of the above-recited substituents are selected independently of their selection above;

the moiety represented by partial Formula (1.1.1):

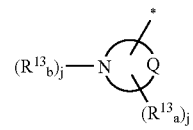

(1.1.1)

in partial Formula (1.1.0) represents:

a. a monocyclic heterocyclic group containing a total of 5 or 6 members of which one said member is nitrogen and Q is selected from O and S where said S may optionally be in the sulfonate form, $-S(=O)_2$; wherein said heterocyclic group is selected from the group consisting of oxazolyl; oxazolidinyl; isoxazolyl; thiazolyl; thiazolidinyl; iso-thiazolyl; morpholinyl; and thiomorpholinyl; or b. a monocyclic heterocyclic group containing a total of 5- or 6-member s of which two said members are nitrogen and a third or fourth said member is independently selected from N, O, and S where said S may optionally be in the sulfonate form, $-S(=O)_2$; wherein said heterocyclic group is selected from the group consisting of triazolyl; triazinyl; tetrazolyl; oxadiazolyl; thiadiazolyl; and $R^{13}_a$ is selected from the group consisting of hydrogen; F; Cl; $-CO_2R^4$; oxo; $-OH$; CN; $NH_2$; $NH(C_1-C_2)$alkyl; $N(C_1-C_2)_2$dialkyl; $-CF_3$; $(C_1-C_4)$alkyl; $(C_2-C_4)$alkenyl; $(C_1-C_2)$alkoxy; $(C_3-C_7)$cycloalkyl; and phenyl; wherein said alkyl, alkenyl, alkoxy, cycloalkyl and phenyl are substituted with 0 to 2 substituents $R^{11}$ where:

$R^{11}$ is a member selected from the group consisting of F; Cl; $-CO_2R^4$; $-OH$; $-CN$; $-CONR^4_aR^4_b$; $-NR^4_aR^4_b$; $-NR^4_aC(=O)R^4_b$; $-NR^4_aC(=O)OR^4_b$; $-NR^4_b$; $-NR^4_aS(=O)_pR^4_b$; $-S(=O)_pNR^4_aR^4_b$; $(C_1-C_4)$alkyl including dimethyl, and $(C_1-C_4)$alkoxy wherein said alkyl and alkoxy are each independently substituted with 0 to 3 substituents independently selected from F and Cl; $(C_1-C_2)$alkoxycarbonyl; $(C_1-C_2)$alkylcarbonyl; and $(C_1-C_2)$alkylcarbonyloxy; and $R^{13}_b$ is a member selected from the group consisting of hydrogen; $(C_1-C_4)$alkyl; $(C_2-C_4)$alkenyl; $(C_1-C_2)$alkoxy; $(C_3-C_7)$cycloalkyl; $C(=O)(_1-C_4)$alkyl; $S(=O)_2(C_1-C_4)$alkyl; and phenyl; wherein said alkyl, alkenyl, alkoxy, cycloalkyl and phenyl are substituted with 0 to 2 substituents $R^{11}$ wherein $R^{11}$ has the same meaning as in above, except that it is selected independently;

B. a (substituted)-amino-aryl or -heterocyclyl moiety selected from the group consisting of 1. alkyl-, alkenyl-, and alkynyl-substituted-amido-aryl moieties of partial Formula (2.0.0):

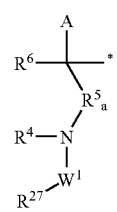

(2.0.0)

wherein: the symbol "*"; $R^4$ and $R^6$; are as defined above, except that all of the above-recited substituents are selected independently of their selection above;

A is a member selected from the group consisting of:
1. the moiety of partial Formula (2.0.3)

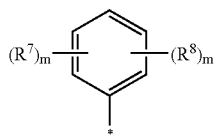

(2.0.3)

wherein: the symbol $R^7$; $R^8$ and m are as defined above, except that all of the above-recited substituents are selected independently of their selection above; and the symbol: "*" indicates the point of attachment of the moiety A to the, remaining portions of partial Formula (2.0.0);

2. the moiety of partial Formula (2.0.4)

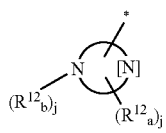

(2.0.4)

which represents a monocyclic heterocyclic group, selected from the group consisting of pyrrolyl; pyrazolyl; imidazolyl; pyridinyl; pyrazinyl; pyrimidinyl; wherein: the symbol $R^{12}_a$ and $R^{12}_b$ are as defined above, except that all of the above-recited substituents are selected independently of their selection above; and the symbol: "*" indicates the point of attachment of the moiety A to the other, remaining portions of partial Formula (2.0.0);

3. the moiety of partial Formula (2.0.5)

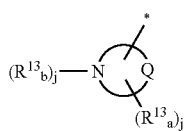

(2.0.5)

which represents
  a. a monocyclic heteroaromatic group containing a total of 5-members of which one said member is nitrogen and Q is selected from O and S where said S may optionally be in the sulfonate form, $-S(=O)_2$; selected from the group consisting of oxazolyl; isoxazolyl; thiazolyl; and iso-thiazolyl; or
  b. a monocyclic heterocyclic group containing a total of 5- or 6-members of which two said members are nitrogen and a third or fourth said member is independently selected from N, O, and S where said S may optionally be in the sulfonate form, $-S(=O)_2$; selected from the group consisting of triazolyl; triazinyl; tetrazolyl; oxadiazolyl; and thiadiazolyl; and
wherein: the $R^{13}_a$, $R^{13}_b$ and j are as defined above, except that all of the above-recited substituents are selected independently of their selection above; and the symbol: "*" indicates the point of attachment of the moiety A to the other, remaining portions of partial Formula (2.0.2);

$R^5_a$ is a member selected from the group consisting of a direct bond; $-C(=O)-$; and $-S(=O)_2-$;

$W^1$ is (1.) a direct bond; (2.) in the case where $R^5_a$ is $-C(=O)-$ or $-S(=O)_2$, $W^1$ is a direct bond or $-(C_1-C_3)$alkylene- wherein any single carbon atom thereof is substituted by 0 to 2 substituents $R^{23}$ where $R^{23}$ is a member selected from the group consisting of $-F$; $-Cl$; $-CO_2R^4$; $-OH$; $-CN$; $(C_1-C_4)$alkoxy; $(C_3-C_7)$cycloalkyl; and phenyl; wherein said alkoxy, cycloalkyl, and phenyl are substituted with 0 to 2 substituents $R^{11}$, wherein said $R^{11}$ is as defined above, except that all of the above-recited substituents are selected independently of their selection above; or (3.) is a member independently selected from the group consisting of the moieties of partial Formulas (2.0.6) through (2.0.16), inclusive:

(2.0.6)

(2.0.7)

(2.0.8)

(2.0.9)

(2.0.10)

(2.0.11)

(2.0.12)

(2.0.13)

(2.0.14)

(2.0.15)

(2.0.16)

wherein: the symbol "→" indicates the point of attachment of the moiety $W^1$ to the nitrogen atom in partial Formula (2.0.0), and the symbol: "*" indicates the point of attachment of the moiety $W^1$ to the other, remaining portions of partial Formula (2.0.0); and $R^4$ is as defined further above, but selected on an independent basis;

$R^{24}$ is selected from the group consisting of hydrogen and $(C_1-C_4)$alkyl; and $R^{25}$ and $R^{26}$ are each selected from the group consisting of —OH; $(C_1-C_2)$alkyl substituted by 0 to 3 substituents selected from F; and OH; and $(C_1-C_2)$alkoxy; and $R^{27}$ is selected from the group consisting of $(C_1-C_6)$alkyl; $(C_2-C_6)$alkenyl; and $(C_2-C_6)$alkynyl; wherein said alkyl, alkenyl, and alkynyl groups comprising $R^{27}$ are substituted with 0 to 3 substituents $R^{28}$ where:

$R^{28}$ is selected from the group consisting of phenyl; F or Cl; oxo; hydroxy; $(C_1-C_2)$alkyl; $(C_1-C_3)$alkoxy; —C(=O)OR$^{29}$; —C(=O)(C$_1$-C$_4$)alkyl; —S(=O)$_2$(C$_1$-C$_4$)alkyl; —C(=O)NR$^{29}$R$^{30}$; —NR$^{29}$R$^{30}$; —NR$^{29}$C(=O)R$^{30}$; —NR$^{29}$C(=O)OR$^{30}$; —NR$^{29}$S(=O)$_p$R$^{30}$; and —S(=O)$_2$NR$^{29}$R$^{30}$, where:

$R^{29}$ and $R^{30}$ are each a member independently selected from the group consisting of hydrogen and $(C_1-C_4)$ alkyl substituted by 0 to 3 substituents selected from the group consisting of F and Cl;

2. cycloalkyl-substituted-amino-aryl moieties of partial Formula (2.1.0):

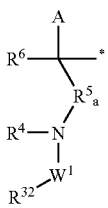

(2.1.0)

wherein A; $W^1$; the symbol "*"; $R^4$; $R^5_a$; and $R^6$ have the same meaning as set out above, except that all of the above-recited substituents are selected independently of their selection above; and $R^{32}$ is a member selected from the group consisting of —(CH$_2$)$_n$-(C$_3$-C$_7$)cycloalkyl, where n is an integer selected form 0, 1, and 2; in the event n is 0, then the α-carbon atom of said (C$_3$-C$_7$)cycloalkyl is substituted by 0 or 1 (C$_1$-C$_4$)alkyl or phenyl, where said alkyl or phenyl are substituted by 0, 1, or 2 of CH$_3$, OCH$_3$, OH or NH$_2$; and in the event that n is 1 or 2, the resulting methylene or ethylene is substituted by 0 or 1 of F; NH$_2$; N(CH$_3$)$_2$; OH; OCH$_3$; (C$_1$-C$_4$)alkyl; or phenyl; where said alkyl and phenyl are substituted by 0, 1, or 2 of CH$_3$, OCH$_3$, OH, and NH$_2$; and further wherein said (C$_3$-C$_7$)cycloalkyl is substituted by 0 to 3 substituents $R^{28}$ where $R^{28}$ is as defined further above, but selected independently 3. aryl and heterocyclic-substituted-amido-aryl moieties of partial Formula (2.2.0):

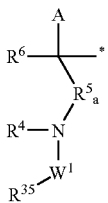

(2.2.0)

wherein: A; $W^1$; the symbol: "*"; $R^4$; $R^5_a$; and $R^6$ have the same meaning as set out above, except that all of the above-cited substituents are selected independently of their selection above; and $R^{35}$ is selected from the group consisting of phenyl; furyl; tetrahydrofuranyl; tetrahydropyranyl; oxetanyl; thienyl; pyrrolyl; pyrrolidinyl; oxazolyl; isoxazolyl; thiazolyl; isothiazolyl; imidazolyl; pyrazolyl; oxadiazolyl; thiadiazolyl; triazolyl; pyridyl; pyrazinyl; pyridazinyl; piperazinyl; pyrimidinyl; pyranyl; azetidinyl; morpholinyl; parathiazinyl; indolyl; indolinyl; benzo(b) furanyl; 2;3-dihydrobenzofuranyl; benzothienyl; 1H-indazolyl; benzimidazolyl; benzoxazolyl; benzisoxazolyl; benzthiazolyl; quinolinyl; isoquinolinyl; phthalazinyl; quinazolinyl; and quinoxalinyl; wherein (1.) said group $R^{35}$ may be substituted upon any one or more carbon atoms thereof by 0 to 3 substituents $R^{28}$ where $R^{28}$ is as defined above, except that it is selected independently; (2.) said group $R^{35}$ is substituted with respect to any one or more nitrogen atoms thereof that is not a point of attachment of said aryl or heterocyclic moiety, by 0 to 3 substituents $R^{13}_b$ is as defined above, except that it is selected independently; and (3.) said group $R^{35}$ with respect to any sulfur atom thereof that is not a point of attachment of said heterocyclic moiety, is substituted by 0 or 2 oxygen atoms;

[Region β] is an alkyl bridging element of partial Formula (3.0.0):

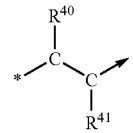

(3.0.0)

wherein:

"*" is a symbol which represents the point of attachment of the moiety of partial Formula (3.0.0) to R$_{egion}$ α;

"→" is a symbol which represents the point of attachment of the moiety of partial Formula (3.0.0) to R$_{egion}$ γ;

$R^{40}$ and $R^{41}$ are both selected from the group consisting of hydrogen; (C$_1$-C$_2$) alkyl including dimethyl; hydroxy; and (C$_1$-C$_3$) alkoxy;

[R$_{egion}$ γ] is an aza-monocyclic moiety of partial Formula (4.0.0):

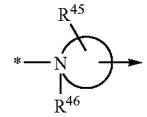

(4.0.0)

wherein:

"*" is a symbol which represents the point of attachment of the moiety of partial Formula (4.0.0) to R$_{egion}$ β of the compound of Formula (I);

"*→*" is a symbol representing a covalent bond attaching any carbon atom of said aza-monocyclic moiety of partial Formula (4.0.0) to R$_{egion}$ δ;

the moiety of partial Formula (4.0.1):

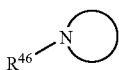
(4.0.1)

in partial Formula (4.0.0) represents a monocyclic heterocyclic group containing a total of from 4- to 7-members of which one said member is nitrogen, wherein said heterocyclic group is a member independently selected from the group consisting essentially of azetidinyl; pyrrolidinyl; piperidinyl; and azepinyl;

$R^{45}$ is absent or is a member independently selected from the group consisting essentially of $(C_1-C_4)$alkyl including dimethyl; $(C_3-C_6)$cycloalkyl; $(C_1-C_4)$alkoxy; $CF_3$; —$CO_2R^4$ where $R^4$ is as defined further above; oxo; —OH; cyano; —C(=O)$NR^4_aR^4_b$; —$NR^4_aR^4_b$; —$NR^4_aC(=O)R^4_b$; —$NR^4_aC(=O)OR^4_b$; —$NR^4_aS(=O)_pR^4_b$; —$S(=O)_pNR^4_aR^4_b$; $(C_1-C_2)$alkoxycarbonyl; $(C_1-C_2)$alkylcarbonyl; $(C_1-C_2)$alkylcarbonyloxy and $(C_1-C_2)$alkoxy$(C_1-C_2)$alkyl; it being understood that in the moiety of partial Formula (4.0.0) $R^{45}$ is a substituent attached to a single carbon atom thereof; where:

$R^4_a$ and $R^4_b$ are each independently selected from hydrogen and $(C_1-C_2)$alkyl;

$R^{46}$ is absent or is a member independently selected from the group consisting essentially of hydrogen; and $(C_1-C_4)$alkyl substituted by 0 or 1 substituent independently selected from $(C_1-C_2)$alkoxy and —$CO_2R^4$ where $R^4$ is as defined further above; and →O; it being understood that in the case where substituent $R^{46}$ is present, that it results in said nitrogen atom and said moiety of partial Formula (4.0.0) is in quaternary form;

[$R_{egion}$ δ] is a member consisting of:

an aryl and heterocyclyl-(substituted) amide, carbamate; or urea moiety of partial Formula (5.1.0):

(5.1.0)

wherein: the symbol "*" is as defined above;

$R^{73}$ is a member selected from the group consisting of hydrogen and $(C_1-C_2)$alkyl;

$W^5$ is selected from the group consisting the moieties of partial Formulas (5.1.1) through (5.1.12):

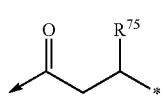
(5.1.1)

(5.1.2)

(5.1.3)

(5.1.4)

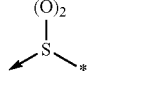
(5.1.5)

(5.1.6)

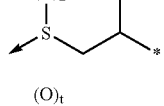
(5.1.7)

(5.1.8)

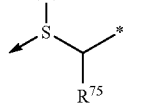
(5.1.9)

(5.1.10)

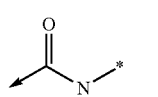
(5.1.11)

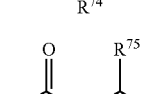

(5.1.12)

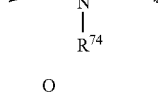

wherein: the symbol: "→" indicates the point of attachment of the moiety $W^5$ represented by partial Formulas (5.1.1) through (5.1.12), inclusive, to the nitrogen atom in partial Formula (5.1.0), and the symbol: "*" indicates the point of attachment of the moiety $W^5$ to $R^{62}$ as defined further below;

$R^{74}$ and $R^{75}$ are each selected from the group consisting of hydrogen; $(C_1-C_2)$alkyl substituted by 0 or 1 substituent independently selected from OH; and $(C_1-C_2)$alkoxy; and $R^{82}$ is a member selected from the group consisting of phenyl; cinnolinyl; furyl; thienyl; pyrrolyl; oxazolyl; isoxazolyl; thiazolyl; isothiazolyl; imidazolyl; imidazolinyl; pyrazolyl; pyrazolinyl; oxadiazolyl; thiadiazolyl; triazolyl; pyridyl; pyrazinyl; pyridazinyl; pyrimidinyl; parathiazinyl; indolyl; isoindolyl; indolinyl; benzo(b)furanyl; 2;3-dihydrobenzofuranyl; benzo(b) thiophenyl; 1H-indazolyl; benzimidazolyl; benzthiazolyl; quinolinyl; isoquinolinyl; phthalazinyl; quinazolinyl; quinoxalinyl; wherein:

the aryl or heterocyclyl moiety is substituted by 0 to 3 substituents $R^{78}$, where:

$R^{78}$ is a member selected from the group consisting of oxo; —Cl; —F; —OH; —$(C_1-C_2)$alkyl; —$(C_1-C_3)$ alkoxy; —CF$_3$; —CN; —C(=O)OR$^{79}$; —C(=O)NR$^{79}$R$^{80}$; —NR$^{79}$R$^{80}$; —NR$^{79}$C(=O)R$^{80}$; —NR$^{79}$C(=O)OR$^{80}$; —NR$^{79}$S(=O)$_2$R$^{80}$; and —S(=O)$_2$NR$^{79}$R$^{80}$, where:

R$^{79}$ and R$^{80}$ are each a member independently selected from the group consisting of hydrogen; and (C$_1$-C$_4$) alkyl.

Attention is drawn to our copending application Ser. Nos. 09/451,826 and 09/452,578.

An important aspect of the present invention is the limitation to R$_{egion}$ δ. The copending cases relate to alternative limitations of Formula (I).

This invention also provides pharmaceutical formulations and dosage forms including as an active ingredient a compound of Formula I. Use of a compound of Formula I in manufacture of a formulation or dosage form and methods of treatment are also provided.

[R$_{egion}$ α] is at the left-hand end of the CCR5 receptor modulator of the present invention. The region designated as R$_{egion}$ α may comprise a moiety selected from several different classes of substituent components, all of which may be isosteres of each other.

The first class of R$_{egion}$ α substituent components (under A.) are heterocyclyl phenylmethylene moieties as described further below. A preferred group of heterocyclyl phenylmethylene moiety embodiments (under A.1.) comprises the group consisting of heterophenylmethylene moieties of partial Formula (1.0.0).

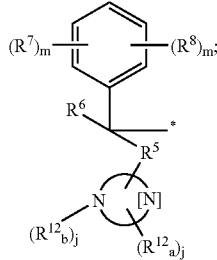

(1.0.0)

The substituent R$^5$ is a member independently selected from the group consisting of a direct bond; —O—; —C(=O)—; —NR$^4$—; and —S(=O)$_p$—; where R$^4$ is hydrogen or (C$_1$-C$_2$)alkyl.

The substituent R$^6$ is a member independently selected from the group consisting of hydrogen; (C$_1$-C$_2$)alkyl; (C$_1$-C$_2$)alkoxy; —C(=O)NH$_2$; —CN; and —OH. Most preferably R$^6$ is hydrogen and there is no substituent at this position.

Included within the partial Formula (1.0.0) are position isomer variations thereof that are not shown, but that arise where the optional substituents R$^7$ and R$^8$ are different. Substituents R$^7$ and R$^8$ are present once or twice or not at all, as indicated by their representation as: "(R$^7$)$_m$" and "(R$^8$)$_m$", where m is defined as being an integer selected from 0, 1, and 2. In the most preferred embodiments of the present invention, m is 0, although in alternative embodiments m is 1.

The substituents R$^7$ and R$^8$ comprise —F; —Cl; —CO$_2$R$^4$; —OH; —CN; —CONR$^4_a$R$^4_b$; —NR$^4_a$R$^4_b$; —NR$^4_a$C(=O)R$^4_b$; —NR$^4_a$C(=O)OR$^4_b$; —NR$^4_a$S(=O)$_p$R$^4_b$; —S(=O)$_p$NR$^4_a$R$^4_b$; (C$_1$-C$_4$)alkyl including dimethyl, and (C$_1$-C$_4$)alkoxy wherein said alkyl and alkoxy are each independently substituted with 0 to 3 substituents independently selected from —F and —Cl; (C$_1$-C$_2$)alkoxycarbonyl; (C$_1$-C$_2$)alkylcarbonyl; and (C$_1$-C$_2$)alkylcarbonyloxy. The substituents R$^4_a$ and R$^4_b$, in turn, are selected from hydrogen and (C$_1$-C$_2$)alkyl. With regard to the R$^7$ and R$^8$ substituent groups, it is preferred that they are absent (m=0); or that if they are present, that they be methyl; cyclopropyl; cyclobutyl; methoxy; —COOH; —OH; —F; —Cl; —COO(C$_1$-C$_2$) alkyl; or —CF$_3$. Of these choices, the more preferred substituent choices for R$^7$ and R$^8$ are that they are absent or that they are —F or Cl.

R$^5$ as defined by Formula (1.0.0) is preferably a direct bond. The moiety R$^5$ may alternatively be selected from —O—; —C(=O)—; —NR$^4$— where R$^4$ is hydrogen or (C$_1$-C$_2$)alkyl; and —S(=O)$_p$—.

In partial Formula (1.0.0), the presence of substituent R$^{12}_a$ is determined by the subscript "j", which is an integer independently selected from 0, 1, and 2. Where j is 0, accordingly, the substituent R$^{12}_a$ will be absent. Where j is 1 or 2, there may be one or two substituents R$^{12}_a$ present, and these may be attached to any available carbon atom in partial Formula (1.0.0).

R$^{12}_a$ is a member independently selected from the group consisting of hydrogen; —F; —Cl; —CO$_2$R$^4$ where R$^4$ is hydrogen or (C$_1$-C$_2$)alkyl as already defined above; -oxo; —OH; —CN; —NH$_2$; —NH(C$_1$-C$_2$)alkyl; —N(C$_1$-C$_2$)$_2$ dialkyl; —CF$_3$; (C$_1$-C$_4$)alkyl; (C$_2$-C$_4$)alkenyl; (C$_1$-C$_4$) alkoxy; (C$_3$-C$_7$)cycloalkyl; and phenyl; wherein said alkyl, alkenyl, alkoxy, cycloalkyl and phenyl groups are substituted with 0 to 2 substituents R$^9$ where R$^9$ is a member independently selected from the group consisting of —F; —Cl; —CO$_2$R$^4$ where R$^4$ is hydrogen or (C$_1$-C$_2$)alkyl; —OH; cyano; —CONR$^4_a$R$^4_b$; —NR$^4_a$R$^4_b$; —NR$^4_a$C(=O)R$^4_b$; —NR$^4_a$C(=O)OR$^4_b$; —NR$^4_a$S(=O)$_p$R$^4_b$; —S(=O)$_p$NR$^4_a$R$^4_b$; (C$_1$-C$_4$)alkyl including dimethyl, and (C$_1$-C$_4$) alkoxy wherein said alkyl and alkoxy are each independently substituted with 0 to 3 substituents independently selected from F and Cl; (C$_1$-C$_2$)alkoxycarbonyl; (C$_1$-C$_2$) alkylcarbonyl; and (C$_1$-C$_2$)alkylcarbonyloxy.

Where a R$^{12}_a$ substituent is present and consists of an alkyl, alkenyl, alkoxy, cycloalkyl or phenyl group, it may optionally be mono- or di-substituted in turn by a further substituent R$^9$, which is independently selected from the above-recited groups. This includes in particular (C$_1$-C$_4$) alkyl substituted with 1 to 3 substituents independently selected from F and Cl. Accordingly, the substituent —CF$_3$ is a preferred definition of R$^9$ in the compounds of partial Formula (1.0.0).

The R$^{12}_b$ substituent is attached directly to the nitrogen atom of the heterocyclic group depicted in partial Formula (1.0.0), and its presence is determined by the subscript "j", which is an integer independently selected from 0, 1, and 2. Where j is 0, accordingly, the substituent R$^{12}_b$ is absent. In that case that the nitrogen atom is attached by a covalent double bond to an adjacent atom in the heterocyclic group depicted in partial Formula (1.0.0). Where j is 1 or 2, there will be one or two substituents R$^{12}_b$ attached to the nitrogen atom of the heterocyclic group depicted in partial Formula (1.0.0). Where two such R$^{12}_b$ substituents are attached, the nitrogen atom is in quaternary form. The substituent R$^{12}_b$ is independently selected from the group consisting of hydrogen; (C$_1$-C$_4$)alkyl; (C$_2$-C$_4$)alkenyl; (C$_1$-C$_2$)alkoxy; (C$_3$-C$_7$) cycloalkyl; and phenyl; wherein said alkyl, alkenyl, alkoxy, cycloalkyl and phenyl are substituted with 0 to 2 substituents R$^9$ wherein R$^9$ has the same meaning as in R$^9$ defined above, except that it is selected independently therefrom.

The group represented by partial Formula (1.0.1):

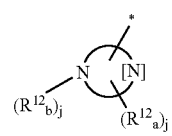

(1.0.1)

represents a monocyclic heterocyclic group, or a bicyclic benzo-fused ring system containing said heterocyclic group wherein said heterocyclic group contains a total of 5- or 6-members of which one or two of said members is nitrogen, the presence of the optional second nitrogen atom being represented by: "[N]"; wherein said heterocyclic group or ring system is selected from the group consisting of pyrrolyl; pyrazolyl; imidazolyl; pyridinyl; pyrazinyl; pyrimidinyl; pyridazinyl; indolyl; indazolinyl; benzimidazolyl; quinolinyl; iso-quinolinyl; and quinazolinyl.

N-containing heterocyclic moieties of partial Formula (1.0.0) result in some of the following preferred embodiments of $R_{egion}$ α, represented by partial Formulas (1.0.4) through (1.0.10), inclusive:

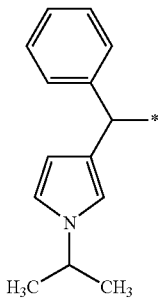
(1.0.4)

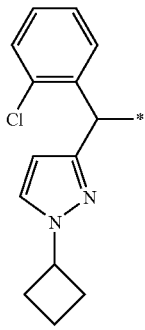
(1.0.5)

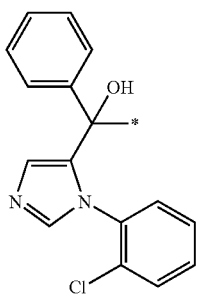
(1.0.6)

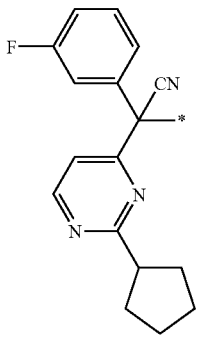
(1.0.7)

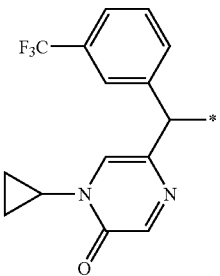
(1.0.8)

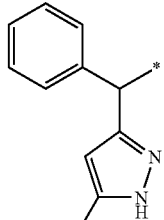
(1.0.9)

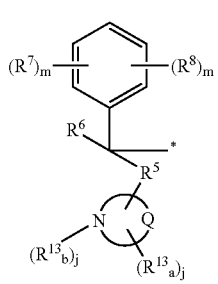
(1.0.10)

A further group of N-containing heterocyclic phenylmethylene moieties (under A.2 comprises several subgeneric groups within partial Formula (1.1.0):

(1.1.0)

where the symbol "*" and $R^5$; $R^6$; $R^7$; $R^8$; j and m are as defined above;
and $R^{13}_a$ is a member selected from the group consisting of hydrogen; F; Cl; —$CO_2R^4$; oxo; —OH; CN; $NH_2$; $NH(C_1$-$C_2)$alkyl; $N(C_1$-$C_2)_2$dialkyl; —$CF_3$; $(C_1$-$C_4)$alkyl; $(C_2$-$C_4)$alkenyl; $(C_1$-$C_2)$alkoxy; $(C_3$-$C_7)$cycloalkyl; and phenyl; wherein said alkyl, alkenyl, alkoxy, cycloalkyl and phenyl are substituted with 0 to 2 substituents $R^{11}$ wherein $R^{11}$ is a member independently selected from the group consisting of F; Cl; —$CO_2R^4$; —OH; —CN; —$CONR^4_aR^4_b$; —$NR^4_aR^4_b$; —$NR^4_aC(=O)R^4_b$; —$NR^4_aC(=O)OR^4_b$; —$NR^4_aS(=O)_p$ $R^4_b$; —$S(=O)_pNR^4_aR^4_b$; $(C_1$-$C_4)$alkyl including dimethyl, and $(C_1-C_4)$alkoxy wherein said alkyl and alkoxy are each independently substituted with 0 to 3 substituents independently selected from F and Cl; $(C_1-C_2)$alkoxycarbonyl; $(C_1-C_2)$alkylcarbonyl; and $(C_1-C_2)$alkylcarbonyloxy; and $R^{13}{}_b$ is selected from the group consisting of hydrogen; $(C_1-C_4)$alkyl; $(C_2-C_4)$alkenyl; $(C_1-C_2)$alkoxy; $(C_3-C_7)$cycloalkyl; $C(=O)(C_1-C_4)$alkyl; $S(=O)_2(C_1-C_4)$alkyl; and phenyl; wherein said alkyl, alkenyl, alkoxy, cycloalkyl and phenyl are substituted with 0 to 2 substituents $R^{11}$ wherein $R^{11}$ has the same meaning as in above, except that it is independently selected therefrom.

The moiety of partial Formula (1.1.1):

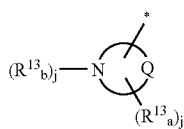

(1.1.1)

represents, inter alia, a monocyclic heterocyclic group containing a total of 5-members of which one said member is nitrogen and Q is selected from O and S The heterocyclic group may be selected from the group consisting of oxazolyl; oxazolidinyl; isoxazolyl; thiazolyl; thiazolidinyl; iso-thiazolyl; morpholinyl and thiamorpholinyl.

Moieties of partial Formula (1.1.0) containing the group of partial Formula (1.1.1) result in the following preferred embodiments of $R_{egion}$ α, represented by partial Formulas (1.1.3) through (1.1.9):

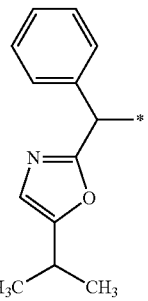

(1.1.3)

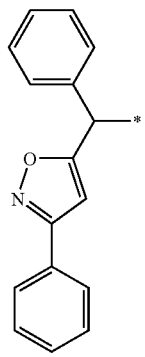

(1.1.4)

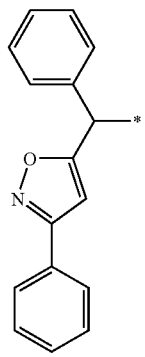

(1.1.5)

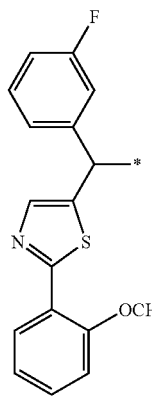

(1.1.6)

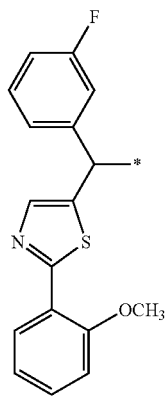

(1.1.7)

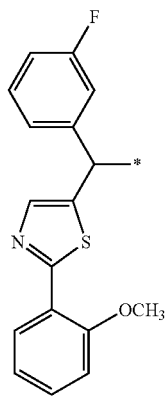

(1.1.8)

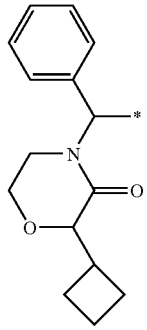

(1.1.9)

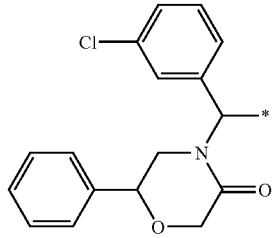

In alternative preferred embodiments the heterocyclic group may selected from the group consisting of triazolyl; triazinyl; tetrazolyl; oxadiazolyl; and thiadiazolyl.

Further preferred embodiments of $R_{egion}$ α, are represented by partial Formulas (1.1.20) through (1.1.24), inclusive:

(1.1.20)
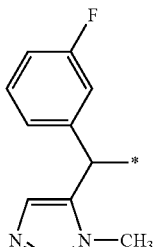

(1.1.21)
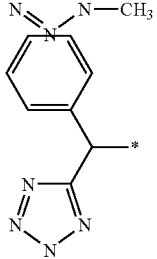

(1.1.22)
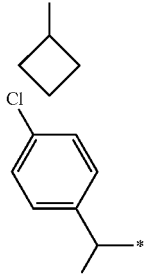

(1.1.23)
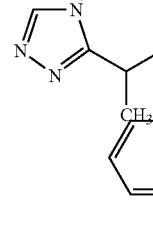

(1.1.24)
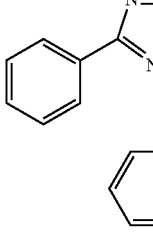

Another class of which $R_{egion}$ α moeities (under B) are (substituted)-amino-aryl or -heterocyclyl moieties which may be independently selected from several groups, as described in more detail below.

The first such class of (substituted)-amino-aryl or -heterocyclyl moieties of $R_{egion}$ α are those in which the amido-aryl or -heterocyclyl portion of the group is substituted by alkyl-, alkenyl-, or alkynyl, as represented by partial Formula (2.0.0)

(2.0.0)

where the symbol "*" and $R^4$ and $R^6$; and m, $R^7$ and $R^8$ in the further definition of A; are as defined in the partial formulas above, except that all of the above-recited substituents are selected independently.

The moiety A in partial Formula (2.0.0) is a member independently selected from the group consisting of several different classes of moieties, as discussed below. The first class represented by partial Formula (2.0.3) is a preferred embodiment of this invention.

(2.0.3)
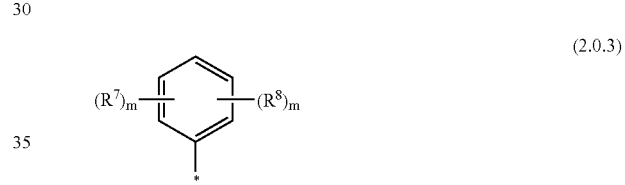

wherein the symbols $R^7$; $R^8$ and m are as defined in the partial formulas further above, except that all of the above-recited substituents are selected independently of their selection in said partial formulas further above; and the symbol: "*" indicates the point of attachment of the moiety A to the other, remaining portions of partial Formula (2.0.0).

Further embodiments of moiety A are depicted by partial Formulas (2.0.4) and (2.0.5). Partial Formula (2.0.4) is:

(2.0.4)

which represents a monocyclic heterocyclic group, selected from the group consisting of pyrrolyl; pyrazolyl; imidazolyl; pyridinyl; pyrazinyl; and pyrimidinyl. It is noted that in the moiety of partial Formula (2.0.3), the symbols $R^{12}_a$ and $R^{12}_b$, and the subscript "j" which determines their presence, are as defined in the partial formulas further above, except that "j" is 0 or 1 and all of the above-recited substituents are selected independently of their selection further above; and the symbol: "*" indicates the point of attachment of the moiety A to the other, remaining portions of partial Formula (2.0.0).

Further embodiments of moiety A are depicted by partial Formula (2.0.5)

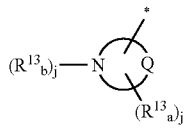
(2.0.5)

which represents a monocyclic heteroaromatic group containing a total of 5-members of which one said member is nitrogen and Q is selected from O and S where said S may optionally be in the sulfonate form, —S(=O)$_2$. Said heterocyclic group may be selected from the group consisting of oxazolyl; isoxazolyl; thiazolyl; and iso-thiazolyl; triazolyl; triazinyl; tetrazolyl; oxadiazolyl; and thiadiazolyl. It is noted that the symbols $R^{13}{}_a$ and $R^{13}{}_b$, and the subscript "j" which determines their presence, are as defined in the partial formulas further above, except that "j" is 0 or 1 and all of the above-recited substituents are selected independently of their selection in said partial formulas further above; and the symbol: "*" indicates the point of attachment of the moiety A to the other, remaining portions of partial Formula (2.0.0).

The group $R^5{}_a$ is selected from a direct bond; —C(=O)—; and —S(=O)$_2$—. In preferred embodiments of the present invention $R^5{}_a$ is a direct bond. It is provided, however, that where $R^5{}_a$ is —CO— or —SO$_2$—, the divalent moiety $W^1$ is defined to additionally include the meaning of being a direct bond.

In partial Formula (2.0.0), $R^{27}$ is a member selected from the group consisting of (C$_1$-C$_6$)alkyl; (C$_2$-C$_6$)alkenyl; and (C$_2$-C$_6$)alkynyl; wherein said alkyl, alkenyl, and alkynyl groups comprising $R^{27}$ may be substituted with 0 to 3 substituents $R^{28}$ where $R^{28}$ is selected from the group consisting of F; Cl; oxo; hydroxy; (C$_1$-C$_2$)alkyl; (C$_1$-C$_3$)alkoxy; —C(=O)OR$^{29}$; C(=O)(C$_1$-C$_4$)alkyl; —S(=O)$_2$(C$_1$-C$_4$)alkyl; —C(=O)NR$^{29}$R$^{30}$; —NR$^{29}$R$^{30}$; —NR$^{29}$C(=O)R$^{30}$; —NR$^{29}$C(=O)OR$^{30}$; —NR$^{29}$S(=O)$_2$R$^{30}$; and —S(=O)$_2$NR$^{29}$R$^{30}$, where $R^{29}$ and $R^{30}$ are independently selected from hydrogen and (C$_1$-C$_4$)alkyl.

The moiety $W^1$ is a member independently selected from the group consisting of divalent moieties of partial Formulas (2.0.6) through (2.0.16), inclusive:

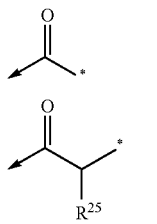
(2.0.6)

(2.0.7)

(2.0.8)

(2.0.19)

(2.0.10)

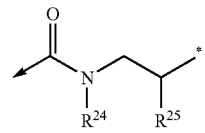
(2.0.11)

(2.0.12)

(2.0.13)

(2.0.14)

(2.0.15)

(2.0.16)

where the symbol: "→" indicates the point of attachment of the moiety $W^1$ to the nitrogen atom in partial Formula (2.0.0), and the symbol: "*" indicates the point of attachment of the moiety $W^1$ to the moiety $R^{27}$ which represents the remaining portions of partial Formula (2.0.0); and $R^{25}$ and $R^{26}$ are each independently a member selected from the group consisting of hydrogen; (C$_1$-C$_2$)alkyl substituted by 0 or 1 substituent independently selected from F and OH; and (C$_1$-C$_2$)alkoxy.

The bridging element —N(R$^4$)—W$^1$— may alternatively constitute or contain several different functionalities. The first and most preferred of these is an amide functionality, which may be represented as: —NR$^4$—C(=O)—. Other functionality types include sulfonamido and ureido moieties within the scope of partial Formulas (2.0.6) through (2.0.16).

Preferred alkyl and alkenyl groups $R^{27}$ include: methyl; ethyl; iso-propyl; t-butyl; and propenyl (allyl). These alkyl and alkenyl groups may be substituted by 0 to 3 substituents $R^{28}$. It is preferred that where a substituent is present that it be a single substituent independently selected from F; Cl; OH; CF$_3$; CH$_3$; OCH$_3$; CN; NH$_2$; NH(CH$_3$); N(CH$_3$)$_2$; NHCOCH$_3$; and NCH$_3$(COCH$_3$). Consequently, groups of partial Formula (2.0.0) which are preferred embodiments of the present invention constituting R$_{egion}$ α include the following moieties of partial Formulas (2.0.30) through (2.0.36), inclusive:

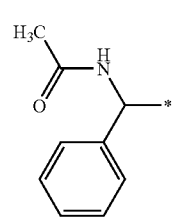
(2.0.30)

-continued (2.0.31) 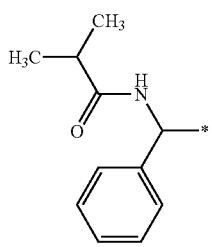

(2.0.32) 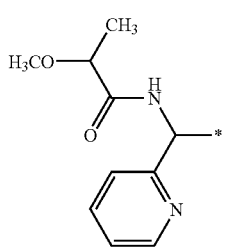

(2.0.33) 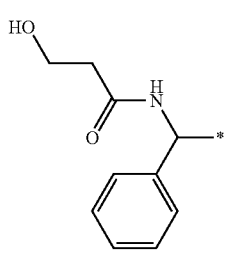

(2.0.34) 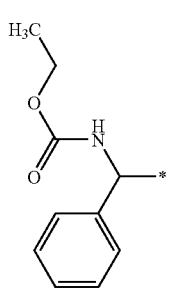

(2.0.35) 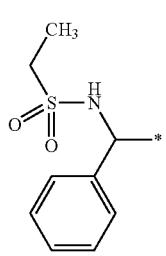

(2.0.36) 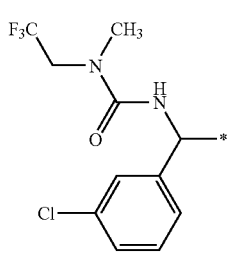

The second class of (substituted)-amido-aryl moieties comprising $R_{egion}$ α are those in which the amido-aryl portion of the group is substituted by -(cycloalkyl) or -alkyl(cycloalkyl), as represented by partial Formula (2.1.0).

(2.1.0) 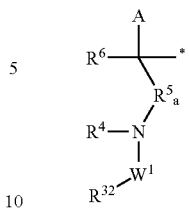

where; A; $W^1$; the symbol "*" and $R^4$; $R^5_a$; $R^6$; and m, $R^7$ and $R^8$ in the further definition of A; have the same meaning as set out in the partial formulas further above, except that all of the above-recited substituents are selected independently of their selection further above. $R^{32}$ is a member independently selected from the group consisting of —$(CH_2)_n$-$(C_3$-$C_7)$cycloalkyl, where n is an integer selected from 0, 1, and 2; in the event n is 0, then the α-carbon atom of said $(C_3$-$C_7)$cycloalkyl may be substituted by $(C_1$-$C_4)$ alkyl or phenyl, where said alkyl or phenyl may be substituted by 1, or 2 of $CH_3$, $OCH_3$, OH or $NH_2$; and in the event that n is 1 or 2, the resulting methylene or ethylene group may be substituted by of F; Cl; CN; $NH_2$; $N(CH_3)_2$; OH; $OCH_3$; $(C_1$-$C_4)$alkyl; or phenyl. It will also be further noted that the basic $(C_3$-$C_7)$cycloalkyl group comprising $R^{32}$ may also be substituted by 0 to 3 substituents $R^{28}$ where $R^{28}$ has the same meaning as defined further above with respect to substituents for group $R^{27}$ under partial Formula (2.0.0), but independently selected therefrom.

Representative cycloalkyl and alkylcycloalkyl groups within the scope of $R^{32}$ include cyclopropyl, cyclobutyl, cyclopentyl, cyclohexyl; cyclopropylmethyl; cyclobutylethyl; cyclopentylpropmethyl; and cyclopentylmethyl. More preferred single substituents for these cycloalkyl and alkylcycloalkyl groups include F, Cl, and CN, especially OH; $OCH_3$; and $NH_2$. Accordingly, groups of partial Formula (2.1.0) which are preferred embodiments of $R_{egion}$ α include partial Formulas (2.1.3) through (2.1.10).

(2.1.3) 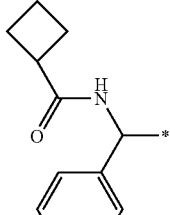

(2.1.4) 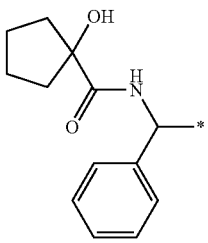

-continued (2.1.5) 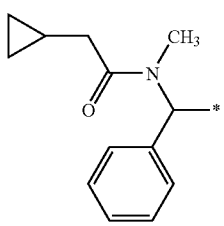

(2.1.6) 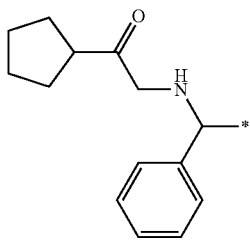

(2.1.7) 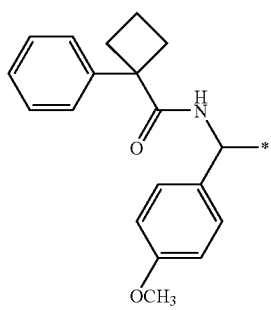

(2.1.8) 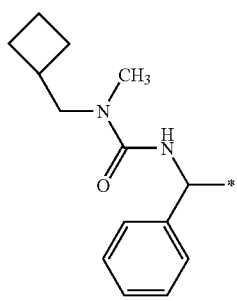

(2.1.9) 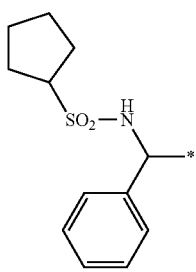

(2.1.10) 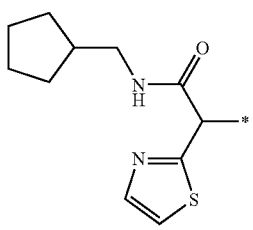

The third class of (substituted)-amido-aryl moieties of $R_{egion}$ α are those in which the amido-aryl portion of the group is substituted by aryl- and heterocyclyl-substituted-amido-aryl moieties of partial Formula (2.2.0).

(2.2.0) 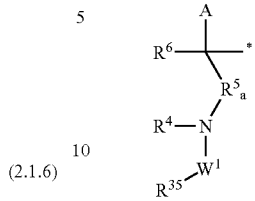

where A; $W^1$; the symbol "*" and $R^4$, $R^5_a$; $R^6$; and m, $R^7$ and $R^8$ in the definition of A; have the same meaning as set out above, except that all of the above-recited substituents are selected independently.

The moiety $R^{35}$ may be selected from the group consisting of phenyl; furyl; tetrahydropyranyl; tetrahydrofuranyl; oxetanyl; thienyl; pyrrolyl; pyrrolidinyl; oxazolyl; isoxazolyl; thiazolyl; isothiazolyl; imidazolyl; imidazolinyl; pyrazolyl; pyrazolinyl; oxadiazolyl; thiadiazolyl; triazolyl; pyridyl; pyrazinyl; pyridazinyl; piperazinyl; pyrimidinyl; pyranyl; azetidinyl; morpholinyl; parathiazinyl; indolyl; isoindolyl; 3H-indolyl; indolinyl, benzo(b)furanyl; 2;3-dihydrobenzofuranyl; benzothienyl; 1H-indazolyl; benzimidazolyl; benzoxazolyl; benzisoxazolyl; benzthiazolyl; benzoxdiazolyl; quinolinyl; isoquinolinyl; phthalazinyl; quinazolinyl; and quinoxalinyl.

Preferred meanings of $R^{35}$ are phenyl; pyrrolyl; oxazolyl; imidazolyl; pyridinyl; pyrimidinyl; triazolyl; indolyl; benzimidazolyl; benzotriazolyl; quinolinyl; thienyl; furfuryl; benzofuranyl; thiazolyl; oxazolyl; isoxazolyl; oxadiazolyl; and benzoxazolyl; and benzoxadiazolyl. Most preferred are tetrahydropyranyl; oxetanyl; azetidinyl and tetrahydrofuranyl. Group $R^{35}$ may be substituted by 3 substituents $R^{28}$ where $R^{28}$ has the same meaning as defined above but selected independently.

Alternative aryl and heterocyclyl groups failing within the scope of $R^{35}$ include phenyl; pyrroly; imidazolyl; pyridyl; oxazolyl; furyl; and benzofuranyl. Preferred single or double substituents for these groups include —CN; —F; —Cl; —CONH$_2$; —CH$_3$; —CF$_3$; and —OCH$_3$.

Accordingly, groups of partial Formula (2.2.0) which are preferred embodiments of $R_{egion}$ α include partial Formulas (2.2.3) through (2.2.14)

(2.2.3) 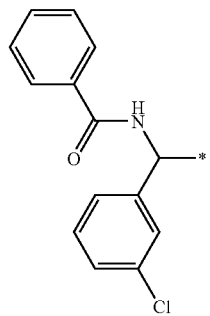

25
-continued
(2.2.4)
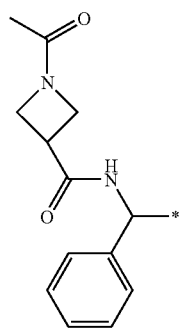
(2.2.5)
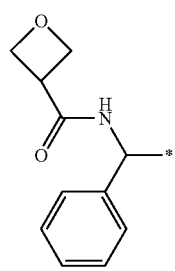
(2.2.6)
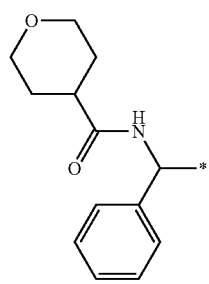
(2.2.7)
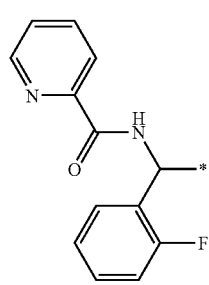
(2.2.8)
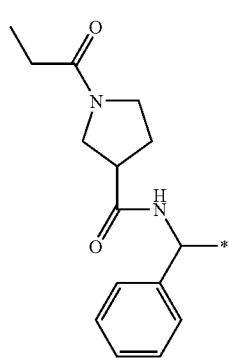
26
-continued
(2.2.9)
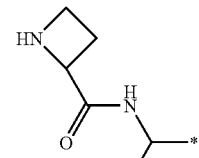
(2.2.10)
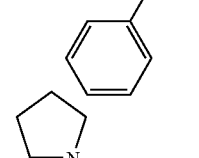
(2.2.11)
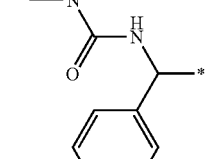
(2.2.12)
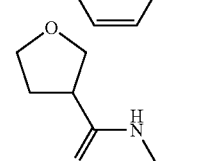
(2.2.13)
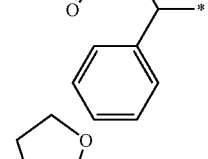
(2.2.14)
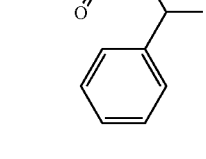
[R$_{egion}$ β] may be considered to be to the left-hand end of the molecule of the present invention as depicted, and comprises a bridging element between R$_{egion}$ α described above, and R$_{egion}$ γ described below.

The alkyl bridging element of $R_{egion}$ β comprises a moiety of partial Formula (3.0.0):

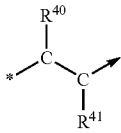

(3.0.0)

where the symbol "*" represents the point of attachment of the alkyl bridging element moiety of partial Formula (3.0.0) to $R_{egion}$ α of the antagonist compound of Formula (I); and the symbol "→" represents the point of attachment of the alkyl bridging element moiety of partial Formula (3.0.0) to $R_{egion}$ γ of the antagonist compound of Formula (I). Substituents $R^{40}$ and $R^{41}$ are both independently selected from the group consisting of hydrogen; ($C_1$-$C_2$) alkyl including dimethyl; hydroxy; and ($C_1$-$C_3$) alkoxy; provided that only one of $R^{40}$ and $R^{41}$ may be ($C_1$-$C_3$) alkoxy or hydroxy, the other one of $R^{40}$ or $R^{41}$ being selected from hydrogen and ($C_1$-$C_2$) alkyl including dimethyl.

Accordingly, $R^{40}$ and $R^{41}$ may be hydrogen; methyl; ethyl; dimethyl, i.e., two methyl groups joined to the single carbon atom to which $R^{40}$ or $R^{41}$ is attached; hydroxy; methoxy; ethoxy; or propoxy.

Some representative embodiments of the alkyl bridging element of partial Formula (3.0.0) include the following moieties of partial Formulas (3.0.1) through (3,0,7), inclusive:

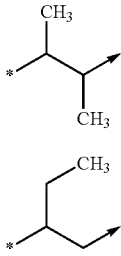

(3.0.1)

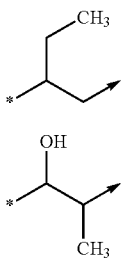

(3.0.2)

(3.0.3)

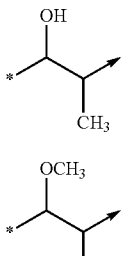

(3.0.4)

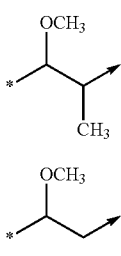

(3.0.5)

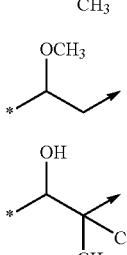

(3.0.6)

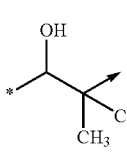

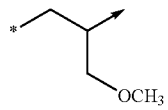

(3.0.7)

In the most preferred embodiments of the antagonist compounds of the present invention, both $R^{40}$ and $R^{41}$ are hydrogen, and the alkyl bridging element of partial Formula (3.0.0) is unsubstituted ethylene. In preferred embodiments a single methyl, hydroxy, or methoxy substituent may be present, resulting in alkyl bridging elements such as those of partial Formulas (3.0.8) through (3.0.10):

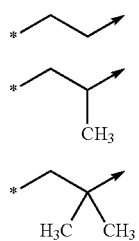

(3.0.8)

(3.0.9)

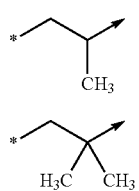

(3.0.10)

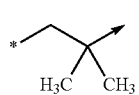

[$R_{egion}$ γ] comprises a member selected from the group consisting of a moiety of partial Formula (4.0.0):

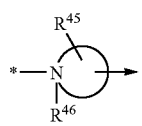

(4.0.0)

where "*" is a symbol representing the point of attachment of the aza-monocyclic moiety of partial Formula (4.0.0) to $R_{egion}$ β; and "→" is a symbol representing the point of attachment to $R_{egion}$ δ. It will be noted that in the moieties of partial Formula (4.0.0) the nitrogen atom covalently bonds said heterocyclic moieties to $R_{egion}$ β.

The heterocyclic moiety of partial Formula (4.0.1):

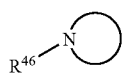

(4.0.1)

constituting a part of partial Formula (4.0.0) represents a monocyclic heterocyclic group containing a total of from 4- to 7-members of which one said member is nitrogen, wherein said heterocyclic group is a member independently selected from the group consisting essentially of azetidinyl; pyrrolidinyl; piperidinyl; and azepinyl, which may also be referred to as homopiperidinyl. With respect to the moieties of partial Formula (4.0.0) which define $R_{egion}$ X then, there is included the following groups represented by partial Formulas (4.0.2) through (4.0.5):

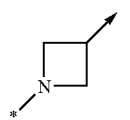

(4.0.2)

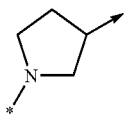

(4.0.3)

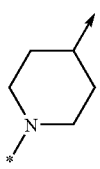

(4.0.4)

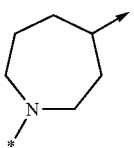

(4.0.5)

The above-defined moieties of partial Formula (4.0.0) are optionally mono-substituted by $R^{45}$ where $R^{45}$ is absent or is a member independently selected from the group consisting essentially of $(C_1-C_4)$ alkyl including dimethyl; $(C_3-C_8)$ cycloalkyl; $(C_1-C_4)$alkoxy; —$CF_3$; —$CO_2R^4$ where $R^4$ is as defined further above; oxo; —OH; —CN; . —C(=O)$NR^4{}_aR^4{}_b$; —NR $4_aR^4{}_b$; —$NR^4{}_aC(=O)R^4{}_b$; —$NR^4{}_aC(=O)OR^4{}_b$; —$NR^4{}_aS(=O)_pR^4{}_b$; —$S(=O)_pNR^4{}_aR^4{}_b$ where $R^4{}_a$ and $R^4{}_b$ are are each independently selected from hydrogen; $(C_1-C_2)$alkyl; $(C_1-C_2)$alkoxycarbonyl; $(C_1-C_2)$alkylcarbonyl; $(C_1-C_2)$alkylcarbonyloxy and $(C_1-C_2)$alkoxy$(C_1-C_2)$alkyl. It will be understood that in the moieties of partial Formula (4.0.0), the substituent $R^{45}$ is attached to a single carbon atom of the above-above-described heterocyclic group. It will be further understood that where $R^{45}$ is defined as $(C_1)$alkyl, the methyl substituent may occur twice on a single carbon atom of the heterocyclic group, i.e., be a dimethyl substituent.

The substituent group $R^{46}$ is absent or is a member independently selected from the group consisting essentially of hydrogen; $(C_1-C_4)$alkyl substituted by 0 or 1 substituent independently selected from $(C_1-C_2)$alkoxy and —$CO_2R^4$ where $R^4$ is as defined further above; and →O. It will be appreciated that in the case where substituent $R^{48}$ is selected to be other than absent, that it will result in said nitrogen atom and said moiety of partial Formula (4.0.0) being in quaternary form. However, generally the quaternary forms of the compounds of the present invention are less preferred than their non-quaternary counterparts, although the skilled artisan can readily foresee that some particular embodiment may have more advantageous properties in its quaternary form than in its non-quaternary form.

Although it is preferred that the moieties of partial Formula (4.0.0) remain unsubstituted, i.e., that $R^{45}$ be absent, some examples of substituted moieties which are included within the scope of preferred embodiments of the present invention are those depicted in partial Formulas (4.0.6) through (4.0.13), inclusive:

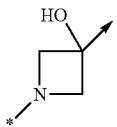

(4.0.6)

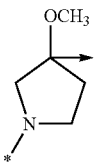

(4.0.7)

(4.0.8)

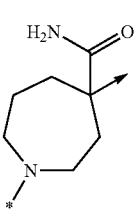

(4.0.9)

(4.0.10)

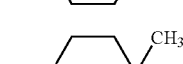

(4.0.11)

(4.0.12)

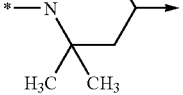

(4.0.13)

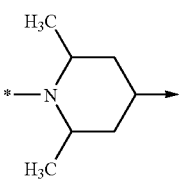

[$R_{egion}$ δ] constitutes the right-hand end of the compounds of Formula (I) and is attached directly to Region γ described above.

$R_{egion}$ δ consists of the compounds of Formula (I) which comprise subclasses having aryl and heterocyclyl-(substituted)-amides, carbamates or ureas of partial Formula (5.1.0):

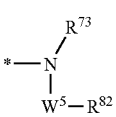

(5.1.0)

where the symbol "*" has the same meaning as defined further above; $R^{73}$ is hydrogen or $(C_1-C_2)$alkyl; and $W^5$ is selected from the moieties of partial Formulas (5.1.1) through (5.1.12), inclusive:

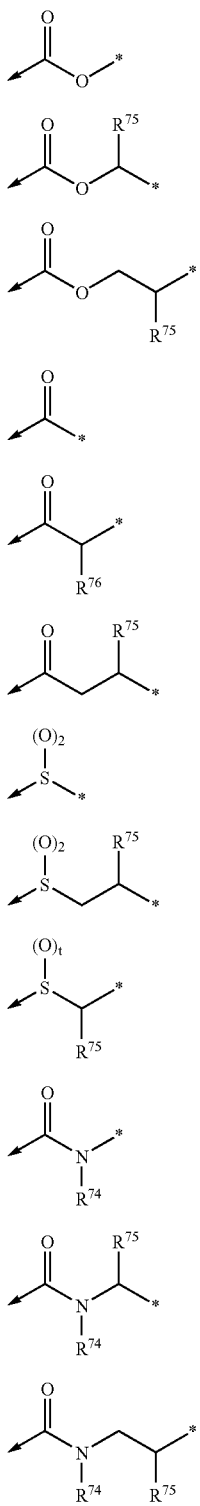

where the symbol: "→" indicates the point of attachment of the moiety W⁵ represented by partial Formulas (5.1.1) through (5.11.12) to the nitrogen atom in partial Formula (5.1.0), and the symbol: "*" indicates the point of attachment of the moiety W⁵ to R⁶². The substituents R⁷⁴ and R⁷⁵ are independently selected from hydrogen; $(C_1-C_2)$alkyl substituted by 0 or 1 substituent independently selected from OH; and $(C_1-C_2)$alkoxy.

The group $R^{82}$ may be selected from phenyl; cinnolinyl; furyl; thienyl; pyrrolyl; oxazolyl; isoxazolyl; thiazolyl; isothiazolyl; imidazolyl; imidazolinyl; pyrazolyl; pyrazolinyl; oxadiazolyl; thiadiazolyl; triazolyl; pyridyl; pyrazinyl; pyrazinyl; pyrimidinyl; parathiazinyl; indolyl; isoindolyl; indolinyl; benzo[b] furanyl; 2;3-dihydrobenzofuranyl; benzo[b] thiophenyl; 1H-indazolyl; benzimidazolyl; benzthiazolyl; quinolinyl; isoquinolinyl; phthalazinyl; quinazolinyl; and quinoxalinyl. The aryl or heterocyclyl groups comprising $R^{82}$ may be substituted with 0 to 3 substituents $R^{78}$, where $R^{78}$ is selected from oxo; —Cl; —F; —OH; $(C_1-C_2)$alkyl; $(C_1-C_3)$alkoxy; —CF$_3$; —CN; —C(=O)OR$^{79}$; —C(=O)NR$^{79}$R$^{80}$; —NR$^{79}$R$^{80}$; —NR$^{79}$C(=O)R$^{80}$; —NR$^{79}$C(=O)OR$^{80}$; —NR$^{79}$S(=O)$_2$R$^{80}$; and —S(=O)$_2$NR$^{79}$R$^{80}$, where $R^{79}$ and $R^{80}$ are each hydrogen or $(C_1-C_4)$ alkyl.

Preferred groups of Formula (5.1.0) include ureas and amides. Carbamates are most preferred.

Accordingly, preferred embodiments of the compounds of the present invention Include partial Formulas (5.1.1) through (5.1.10):

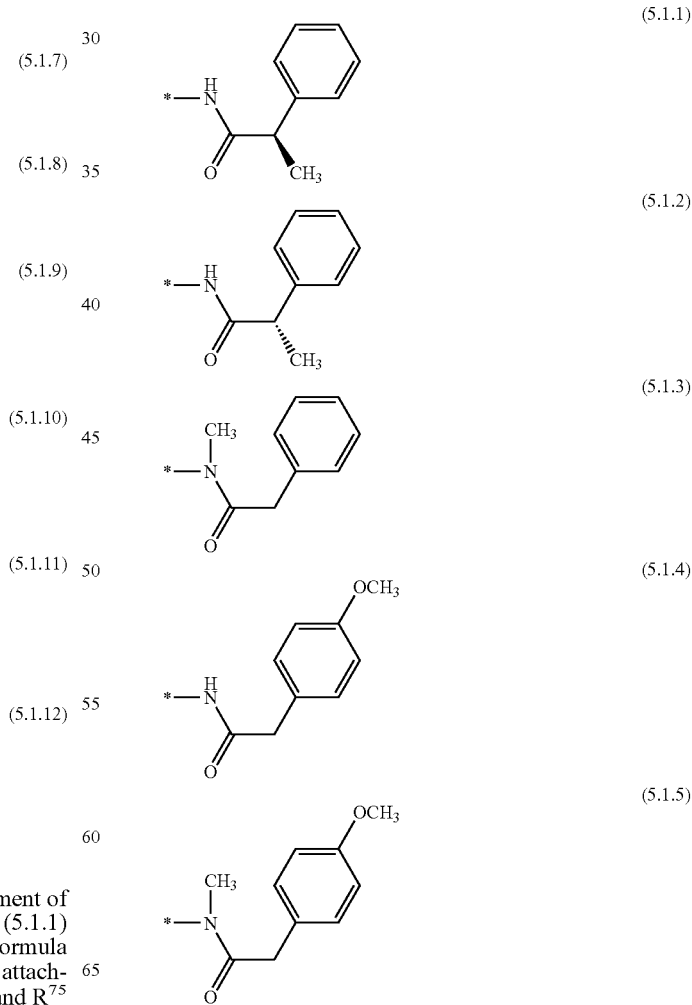

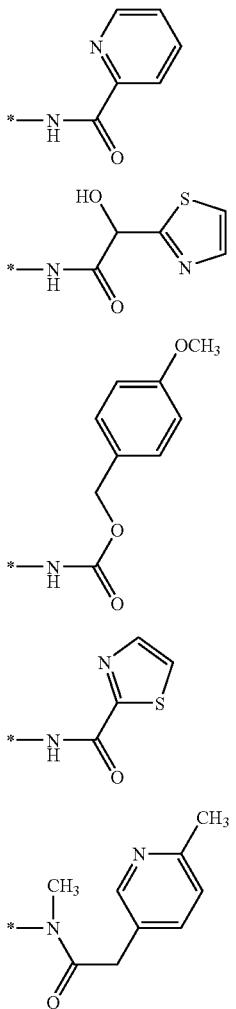

The compounds of the present invention may be utilized in the form of acids, esters, or other chemical derivatives. It is also within the scope of the present invention to utilize those compounds in the form of pharmaceutically acceptable salts derived from various organic and inorganic acids and bases in accordance with procedures well known in the art. The expression "pharmaceutically acceptable salt" as used herein is intended to mean an active ingredient comprising a compound of Formula (I) utilized in the form of a salt thereof, especially where said salt form confers on said active ingredient improved pharmacokinetic properties as compared to the free form of said active ingredient or other previously disclosed salt form.

A pharmaceutically acceptable salt form of said active ingredient may also initially confer a desirable pharmacokinetic property on said active ingredient which it did not previously possess, and may even positively affect the pharmacodynamics of said active ingredient with respect to its therapeutic activity in the body.

The pharmacokinetic properties of said active ingredient which may be favorably affected include, e.g., the manner in which said active ingredient is transported across cell membranes, which in turn may directly and positively affect the absorption, distribution, biotransformation or excretion of said active ingredient. While the route of administration of the pharmaceutical composition is important and various anatomical, physiological and pathological factors can critically affect bioavailability, the solubility of said active ingredient is usually dependent upon the character of the particular salt form thereof which it utilized. Further, an aqueous solution may provide the most rapid absorption of an active ingredient into the body of a patient being treated, while lipid solutions and suspensions, as well as solid dosage forms, may result in less rapid absorption. Oral ingestion of said active ingredient is the most preferred route of administration for reasons of safety, convenience, and economy, but absorption of such an oral dosage form can be adversely affected by physical characteristics such as polarity, emesis caused by irritation of the gastrointestinal mucosa, destruction by digestive enzymes and low pH, irregular absorption or propulsion in the presence of food or other drugs, and metabolism by enzymes of the mucosa, the intestinal flora, or the liver. Formulation of said active ingredient into different pharmaceutically acceptable salt forms may be effective in overcoming or alleviating one or more of the above-recited problems encountered with absorption of oral dosage forms.

Well-known pharmaceutically acceptable salts include, but are not limited to acetate, adipate, alginate, aspartate, benzoate, benzenesulfonate, besylate, bisulfate, butyrate, citrate, camphorate, camphorsulfonate, cyclopentanepropionate, digluconate, dodecysulfate, ethanesulfonate, fumarate, glucoheptanoate, gluconate, glycerophosphate, hemisuccinate, hemisulfate, heptanoate, hexanoate, hippurate, hydrochloride, hydrobromide, hydroiodide, 2-hydroxyethanesulfonate, isethionate, lactate, lactobionate, maleate, mandelate, methanesulfonate, 2-naphthalenesulfonate, nicotinate, nitrate, oxalate, oleate, pamoate, pectinate, persulfate, 3-phenylpropionate, phosphonate, picrate, pivalate, propionate, salicylate, sodium phosphate, stearate, succinate, sulfate, sulfosalicylate, tartrate, thiocyanate, thiomalate, tosylate, and undecanoate.

Base salts of the compounds of the present invention include, but are not limited to ammonium salts; alkali metal salts such as sodium and potassium; alkaline earth metal salts such as calcium and magnesium; salts with organic bases such as dicyclohexylamine, meglumine, N-methyl-D-glucamine, tris-(hydroxymethyl)-methylamine (tromethamine), and salts with amino acids such as arginine, lysine, etc. Compounds of the present invention which comprise basic nitrogen-containing groups may be quaternized with such eagents as ($C_1$–$C_4$) alkyl halides, e.g., methyl, ethyl, iso-propyl and tert butyl chlorides, bromides and iodides; di($C_1$–$C_4$) alkyl sulfate, e.g., dimethyl, diethyl and diamyl sulfates; ($C_{10}$–$C_{18}$) alkyl halides, e.g., decyl, dodecyl, lauryl, myristyl and stearyl chlorides, bromides and iodides; and aryl-($C_1$ . C4) alkyl halides, e.g., benzyl chloride and phenethyl bromide. Such salts permit the preparation of both water-soluble and oil-soluble compounds of the present invention.

Among the above-recited pharmaceutical salts those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate, and tromethamine.

Multiple salts forms are included within the scope of the present invention where a compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

The compounds of this invention can be administered alone but will generally be administered in admixture with one or more suitable pharmaceutical excipients, diluents or carvers selected with regard to the intended route of administration and standard pharmaceutical practice.

For example, the compounds of the formula (I) can be administered orally or sublingually in the form of tablets, capsules, ovules, elixirs, solutions or suspensions, which may contain flavouring or colouring agents, for immediate or controlled release applications.

Such tablets may contain excipients such as microcrystalline cellulose, lactose, sodium citrate, calcium carbonate, dicalcium phosphate and glycine, disintegrants such as starch (preferably corn, potato or tapioca starch), alginic acid and certain complex silicates, and granulation binders such as polyvinylpyrrolidone, sucrose, gelatin and acacia. Additionally, lubricating agents such as magnesium stearate, sodium lauryl sulfate and talc may be included.

Solid compositions of a similar type may also be employed as fillers in gelatin capsules. Preferred excipients in this regard include lactose or milk sugar as well as high molecular weight polyethylene glycols. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol and glycerin, and combinations thereof.

The compounds of the formula (I) can also be injected parenterally, for example, intravenously, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotopic with blood. The aqueous solutions should be suitably buffered (preferably to a pH of from 3 to 9). If necessary, the preparation of suitable parenteral formulations under sterile conditions is readily accomplished by standard pharmaceutical techniques well known to those skilled in the art.

For oral and parenteral administration to human patients, the daily dosage level of the compounds of the formula (I) will usually be from 1 microgram/kg to 25 mg/kg (in single or divided doses).

Thus tablets or capsules of the compound of the formula (I) may contain from 0.05 mg to 1.0 g of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container or a nebuliser with the use of a suitable propellant, eg dichlorodifluoromethane, trichlorofluoromethane, dichlorotetrafluoroethane, a hydrofluoroalkane such as 1,1,1,2-tetrafluorethane (HFA 134a), carbon dioxide or other suitable gas. In the case of a pressurised aerosol, the dosage unit may be determined by providing a valve to deliver a metered amount. The pressurised container or nebuliser may contain a solution or suspension of the active compound, eg using a mixture of ethanol and the propellant as the solvent which may additional contain a lubricant, eg sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol or dry powder formulations are preferably arranged so that each metered dose or "puff" contains from 20 µg to 20 mg of a compound of the formula (I) for delivery to the patient. The overall daily dose with an aerosol will be in the range of from 20 µg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. The compounds of the formula (I) may also be transdermally administered by the use of a skin patch. They may also be administered by the ocular route, particularly for treating neurological disorders of the eye.

For ophthalmic use, the compounds can be formulated as micronised suspensions in isotonic, pH adjusted, sterile saline, or, preferably, as solutions in isotonic, pH adjusted, sterile saline, optionally in combination with a preservative such as benzylalkonium chloride. Alternatively, they may be formulated in an ointment such as petrolatum.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benyl alcohol and water.

The compounds of Formula (I) are described herein as possessing biological activity such that they are able to modulate CCR5 chemokine receptor activity and consequent or associated pathogenic processes subsequently mediated by the CCR5 receptor and its ligands. The expression modulate CCR5 chemokine receptor activity as used herein is intended to refer to manipulation of the basic physiological processes and agencies which involve CCR5 chemokine receptors and their ligands. Included within the scope of this intended meaning are all types and subtypes of CCR5 receptors, in whatever tissues of a particular patient they are found, and in or on whatever components of the cells comprising those tissues they may b located. Most commonly, CCR5 receptors are situated on the cell membranes of particular cell types such as monocytes. CCR5 receptors participate in and define, along with various endogenous ligands to which they are naturally bound, signaling pathways which control important cellular and tissue functions by means of the influence which they exert on the movement of agents such as the chemokines, into and out of those cells and tissues.

The basic functioning of the CCR5 receptors and their ligands may be modulated in a number of ways, and the scope of the present invention is not limited in that regard to any particular existing or hypothesized pathway or process. Thus, included within the intended meaning of modulation of CCR5 chemokine receptor activity, is the use of synthetically derived modulators introduced into a patient being treated, such as the compounds of Formula (I) described herein. These exogenous agents may modulate CCR5 receptor activity by such well known mechanisms as competitive binding in which the natural ligands are displaced and their inherent functions disrupted. However, the present invention is not limited to any such specific mechanism or mode of action. Thus, "modulation" as used herein is intended to encompass preferably agonism, but also antagonism, partial agonism and/or partial antagonism. Correspondingly, the term "therapeutically effective amount" means the amount of the subject compound that will elicit the biological or medical response of a tissue, system, animal or human that is being sought.

The term "patient" in this specification refers particularly to humans. However the compounds, methods and pharmaceutical compositions of the present invention may be used in the treatment of animals.

Further included within the scope of the present invention are metabolites or residues of the compounds of Formula (I) which possess biological activity such that they are able to modulate CCR5 chemokine receptor activity and consequent or associated pathogenic processes subsequently mediated by the CCR5 receptor and its ligands. Once synthesized, the CCR5 chemokine receptor modulating activities and specificities of the compounds of Formula (I) according to the present invention may be determined using in vitro and in vivo assays which are described in detail further below.

The desirable biological activity of the compounds of Formula (I) may also be improved by appending thereto appropriate functionalities which enhance existing biological properties of the compound, improve the selectivity of the compound for the existing biological activities, or add to the existing biological activities further desirable biological activities. Such modifications are known in the art and include those which increase biological penetration into a given biological system, e.g., blood, the lymphatic system, and central nervous system; increase oral availability; increase solubility to allow administration by injection; alter metabolism; and alter the rate of excretion of the compound of Formula (I).

The dosage and dose rate of the compounds of Formula (I) effective for treating or preventing diseases and conditions in a patient which are mediated by or associated with modulation of CCR5 chemokine receptor activity as described herein, as well as for favorably affecting the outcome thereof in said patient, in accordance with the methods of treatment of the present invention comprising administering to said patient a therapeutically effective amount of a compound of Formula (I), will depend on a variety of factors such as the nature of the active ingredient, the size of the patient, the goal of the treatment, the nature of the pathology being treated, the specific pharmaceutical composition used, the concurrent treatments that the patient may be subject to, and the observations and conclusions of the treating physician.

Generally, however, the effective therapeutic dose of a compound of Formula (I) which will be administered to a patient will be between about 10 µg (0.01 mg)/kg and about 60.0 mg/kg of body weight per day, preferably between about 100 µg (0.1 mg/kg and about 10 mg/kg of body weight per day, more preferably between about 1.0 mg/kg and about 6.0 mg/kg of body weight per day, and most preferably between about 2.0 mg/kg and about 4.0 mg/kg of body weight per day of the active ingredient of Formula (I).

Included within the scope of the present invention are embodiments comprising coadministration of, and compositions which contain, in addition to a compound of the present invention as active ingredient, additional therapeutic agents and active ingredients. Such multiple drug regimens, often referred to as combination therapy, may be used in the treatment and prevention of any of the diseases or conditions mediated by or associated with CCR5 chemokine receptor modulation, particularly infection by human immunodeficiency virus, HIV. The use of such combinations of therapeutic agents is especially pertinent with respect to the treatment and prevention of infection and multiplication within a patient in need of treatment or one at risk of becoming such a patient, of the human immunodeficiency virus, HIV, and related pathogenic retroviruses. The ability of such retroviral pathogens to evolve within a relatively short period of time into strains resistant to any monotherapy which has been administered to said patient is well known in the technical literature.

In addition to the requirement of therapeutic efficacy which may necessitate the use of active agents in addition to the CCR5 chemokine receptor modulating compounds of Formula (I), there may be additional rationales which compel or highly recommend the use of combinations of drugs involving active ingredients which represent adjunct therapy, i.e., which complement and supplement the function performed by the CCR5 chemokine receptor modulating compounds of the present invention. Such supplementary therapeutic agents used for the purpose of auxiliary treatment include drugs which, instead of directly treating or preventing a disease or condition mediated by or associated with CCR5 chemokine receptor modulation, treat diseases or conditions which directly result from or indirectly accompany the basic or underlying CCR5 chemokine receptor modulated disease or condition. For example, where the basic CCR5 chemokine receptor modulated disease or condition is HIV infection and multiplication, it may be necessary or at least desirable to treat opportunistic infections, neoplasms, and other conditions which occur as the result of the immune-compromised state of the patient being treated. Other active agents may be used with the compounds of Formula (I), e.g., in order to provide immune stimulation or to treat pain and inflammation which accompany the initial and fundamental HIV infection.

Thus, the methods of treatment and pharmaceutical compositions of the present invention may employ the compounds of Formula (I) in the form of monotherapy, but said methods and compositions may also be used in the form of multiple therapy in which one or more compounds of Formula (I) are coadministered in combination with one or more known therapeutic agents such as those described in detail further herein.

The present invention also provides methods of treatment in which said pharmaceutical compositions are administered to a patient. Such methods relate to treating or preventing a disease or condition by modulating CCR5 chemokine receptor activity and consequent or associated pathogenic processes subsequently mediated by the CCR5 receptor and the active ligands with which it interacts or is bound. CCR5 and the other chemotactic cytokine, i.e., chemokine, receptors, play a key role in the control of a number of processes which take place in the bodies of animals. Chemokine receptors, of which more than forty different species divided into four families are presently known to exist, are proteins having a number of structural features in common, which act through chemical signaling. In the a family of chemokines, one amino acid (X) separates the first two cysteine © residues, while in the β-chemokines the first two cysteine residues are adjacent to each other (C—C). Accordingly, these two families are identified as CXC and CC chemokines, respectively. The chemokines bind specific cell-surface receptors belonging to the family of G-protein-coupled seven-transmembrane-domain proteins called "chemokine receptors", named in accordance with the class of chemokines which they bind, followed by "R" and a number. Thus, "CCR5" is a C—C chemokine receptor. See Horuk, *Trends Pharm. Sci.*, 15,159–165 (1994) for further details. CCR5 thus belongs to the β-chemokine receptor family, which is currently known to contain eight members, CCR1 through CCR8.

The CC type of chemokine receptor interacts with various signaling proteins, including the monocyte chemoattractant proteins, MCP-1, -2, -3, -4, and -5; eotaxin-1; macrophage inflammatory proteins MIP-1α, and MIP-1β; and those regulated upon activation which are normal T-cell expressed and secreted, RANTES. The CCR5 type of chemokine receptor in particular is known to interact with MIP-1α, MIP-1β; and RANTES in monocytes, activated T-cells, dendritic cells, and natural killer cells. These β-chemokines do not act on neutrophils but rather attract monocytes, eosinophils, basophils, and lymphocytes with varying degrees of selectivity.

The present invention relates to compounds of Formula (I) which are useful in treating or preventing HIV infection, and to methods of treatment and pharmaceutical compositions containing such compounds as the active ingredient. It will be understood, that the ten "HIV" as used herein refers to human immunodeficiency virus (HIV), which is the etiological agent of AIDS (acquired immune deficiency syndrome), a disease that results in progressive destruction of the immune system and degeneration of the central and peripheral nervous system. Several HIV replication inhibitors are currently used as therapeutic or prophylactic agents against AIDS, and numerous others are presently under investigation.

In addition to cell-surface CD4, it has recently been shown that for entry into target cells, human immunodeficiency viruses require a chemokine receptor, CCR5 and CXCR-4 among others, as well as the virus's primary receptor CD4. The principal cofactor for entry mediated by the envelope glycoproteins of primary macrophage-tropic strains of HIV-1 is CCR5, which as already mentioned, is a receptor for the β-chemokines RANTES, MIP-1α and MIP-1β. See Deng, et al. *Nature*, 381, 661–666 (1996) for a further description of CCR5 mediated HIV entry.

HIV attaches to the CD4 molecule on cells through a region of its envelope protein, gp120, and gp120 is part of a multi-subunit complex, most likely a trimer of gp160, i.e., gp120+gp41. It is believed that the CD4 binding site on the gp120 of HIV interacts with the CD4 molecule on the cell surface, triggering conformational changes across the trimer, which allow it to bind to another cell-surface receptor, such as CCR5. This in turn enables gp41 to induce fusion with the cell membrane, and entry of the viral core into the cell. In addition, macrophage-tropic HIV and SIV envelope proteins have been shown to induce a signal through CCR5 on CD4+ cells, which may enhance the replication of the virus. See Weissman, et al., *Nature*, 389, 981–985 (1997) for a description of this phenomenon. Further, it has been shown that a complex of gp120 and soluble CD4 interacts specifically with CCR5 and inhibits the binding of the natural CCR5 ligands, as described in Wu, et al., *Nature*, 384, 179–183 (1998); and Trkola, et al., *Nature*, 384, 184–187 (1996). It has further been demonstrated that β-chemokines and related molecules, e.g., (AOP)-RANTES, prevent HIV fusion to the cell membrane and subsequent infection, both in vitro, as described in Dragic, of al., *Nature*, 381, 667–673 (1996), and in animal models. Finally, absence of CCR5 appears to confer protection from HIV-1 infection, as described in *Nature*, 382, 668–669 (1996). In particular, an inherited frame-shifting mutation in the CCR5 gene, Δ2, has been shown to abolish functional expression of the gene in vitro, and individuals homozygous for the mutation are apparently not susceptible to HIV infection, white at the same time they do not seem to be immuno-compromised by this variant. Furthermore, those heterozygote individuals that have been infected by HIV progress more slowly to full-blown clinical AIDS. In addition to validating the role of CCR5 in the infectious cycle of HIV, the above observations suggest that CCR5 is dispensable in the adult organism.

Although most HIV-1 isolates studied to date utilize CCR5 or CXCR-4, at least nine other chemokine receptors, or structurally related molecules, have also been described as supporting HIV-1 env-mediated membrane fusion or viral entry in vitro. These include CCR2b, CCR3, BOB/GPR15, Bonzo/STRL33/TYMSTR, GPR1, CCR8, US28, V28/CX3CR1, LTB-4, and APJ. There is good evidence that CCR3 can be used efficiently by a significant fraction of HIV-1 isolates in vitro, provided that this protein is over-expressed in transfected cells. Nevertheless, consistent evidence indicates that anti-HIV drugs targeted to chemokine receptors may not be compromised by this variability. Indeed, the chemokines RANTES, MIP-1α, MIP-1β, SDF-1 have been shown to suppress replication of primary HIV isolates. A derivative of RANTES, (AOP)-RANTES, is a sub-nanomolar antagonist of CCR5 function in monocytes. Monoclonal antibodies to CCR5 have been reported to block infection of cells by HIV in vitro. A small molecule antagonist of CXCR4, identified as AMD3100, has been reported to inhibit infection of susceptible cultures by $CXCR^4$ dependent primary and lab-adapted HIV viruses while another small molecule called TAK 779 blocks entry of CCR5-tropic strains (Baba, et al, *PNAS*, 96 (10), 5698–5703 (1999); in addition, the majority of primary strains from early and late disease stages utilize CCR5 exclusively or in addition to other chemokine receptors, indicating that CCR5 dependent infection may play an essential role in the initiation and maintenance of productive HIV infection in a host. Accordingly, an agent which blocks CCR5 in patients including mammals, and especially humans who possess normal chemokine receptors, can reasonably be expected to prevent infection in healthy individuals and slow or halt viral progression in infected patients.

Accordingly, the present invention is directed to the compounds of Formula (I) which inhibit the entry of human immunodeficiency virus into target cells and are therefore of value in the prevention and/or treatment of infection by HIV, as well as the prevention and/or treatment of the resulting acquired immune deficiency syndrome (AIDS). Evidence can be produced which is probative of the fact that the compounds of Formula (I) described herein inhibit viral entry through selective blockade of CCR5 dependent fusion. Consequently, the present invention also relates to pharmaceutical compositions containing the compounds of Formula as an active ingredient, as well as to the corresponding method of use of the compounds of Formula (I) as stand-alone agents, or in conjunction with other agents for the prevention and treatment of infection by HIV and resulting AIDS.

The utility of the compounds of Formula (I) of the present invention as inhibitors of HIV infection may be demonstrated by any one or more methodologies known in the art, such as the HIV microculture assays described in Dimitrov et al., *J. Clin. Microbiol.* 28, 734–737 (1990)), and the pseudotyped HIV reporter assay described in Connor et al., *Virology* 206 (2) 935–44 (1995). In particular, specific compounds of Formula (I) disclosed herein as preferred embodiments are shown to inhibit p24 production following replication of laboratory-adapted and primary HIV strains in primary blood lymphocytes (PBLs) and clonal cell-lines known to support replication of both CCR5 and CXCR-4 tropic viruses, e.g., PM-1 and MOLT4-clone 8. It is also noted that only those viral strains known to use CCR5 are shown to be inhibited. whereas replication of CXCR-4 tropic viruses is shown to be unaffected, indicating that compounds of Formula (I) disclosed herein are able to prevent viral entry through selective blockade of CCR5 dependent fusion. Furthermore, compounds of Formula (I) are shown to inhibit entry of chimeric HIV reporter viruses pseudotyped with envelope from a CCR5 dependent strain (ADA). Finally, compounds of Formula (I) are shown to inhibit infection of primary cells by HIV isolated from infected patient blood. Further confirmation of this anti-HIV mechanism is provided by experiments outlined below.

The ability of the compounds of Formula (I) to modulate chemokine receptor activity is demonstrated by methodology known in the art, such as the assay for CCR5 binding following procedures disclosed in Combadiere et al., J. Leukoc. *Biol.* 60, 147–152 (1996); and/or intracellular calcium mobilisation assays as described by the same authors. Cell lines expressing the receptor of interest include those naturally expressing the receptor, such as PM-1, or IL-2 stimulated peripheral blood lymphocytes (PBL), or a cell engineered to express a recombinant receptor, such as CHO, 300.19, L1.2 or HEK-293. In particular, the compounds of Formula (I) disclosed herein are shown to have activity in preventing binding of all known chemokine ligands to CCR5 in the above-mentioned binding assays. In addition, the compounds of Formula (I) disclosed herein are shown to prevent intracellular calcium mobilization in response to endogenous agonists, which is consistent with their functioning as CCR5 antagonists. For the treatment of infection by HIV and the prevention and/or treatment of the resulting acquired immune deficiency syndrome (AIDS), compounds of Formula (I) which are shown to be antagonists are preferred to compounds of Formula (I) which are shown to be agonists.

The present invention in one of its preferred embodiments is directed to the use of the compounds of Formula (I) disclosed herein for the prevention or treatment of infection by a retrovirus, in particular, the human immunodeficiency virus (HIV) and the treatment and/or delaying of the onset of consequent pathological conditions, including but no limited to AIDS. The expressions "treating or preventing AIDS", and "preventing or treating infection by HIV" as used herein are intended to mean the treatment of a wide range of states of HIV Infection: AIDS, ARC (AIDS related complex), both symptomatic and asymptomatic, and actual or potential exposure to HIV. The quoted expressions are not intended, however, to be limited to the recited treatments, but rather are contemplated to include all beneficial uses relating to conditions attributable to an AIDS causative agent. For example, the compounds of Formula (I) are useful in treating infection by HIV after suspected past exposure to HIV by, e.g., blood transfusion, organ transplant, exchange of body fluids, sexual intercourse, bites, needle stick, or exposure to patient blood. In addition, a compound of Formula (I) may be used for the prevention of infection by HIV and the prevention of AIDS, such as in pre-or post- coital prophylaxis or in the prevention of maternal transmission of the HIV virus to a fetus or a child, whether at the time of birth, during the period of nursing, or in any other manner as above-described.

In a preferred embodiment of the present invention, a compound of Formula (I) may be used in a method of inhibiting the binding of human immunodeficiency virus to a chemokine receptor such as CCR5, which comprises contacting the target cell with a therapeutically effective amount of a compound of Formula (I) which is effective to inhibit the binding of the virus to the chemokine receptor. The subject treated by these preferred methods of the present invention is a mammal, preferably a human, male or female, in whom modulation of chemokine receptor activity is desired and contemplated to be efficacious. As already pointed out, the term "modulation" as used herein is intended to encompass preferably antagonism, but also agonism, partial antagonism and/or partial agonism. Also, the expression "therapeutically effective amount" as used herein is intended to mean the amount of a compound of Formula (I) as disclosed herein that will elicit the biological or medical response of a tissue, system, or animal, especially human that is being sought.

In another preferred embodiment of the present invention, a compound of Formula (I) may be used to evaluate putative retrovirus, especially HIV, mutants considered to be resistant to anti-HIV therapeutic agents, including the compounds of Formula (I) disclosed herein. Mutant viruses may be isolated from in vitro cultures by methods known in the art, but may also be isolated from in vivo animal infection models which have been disclosed in the art. More significantly, mutant viruses may be isolated from samples of patients undergoing treatment, whether optimal or sub-optimal, comprising administration of a compound of Formula (I), or any combination thereof with other known or to-be-discovered therapeutic agents. Such mutant viruses or their components, particularly their envelope proteins, may be used for several advantageous purposes, including but not limited to the following; (i) the evaluation and/or development of novel chemokine modulators or other agents having improved activity against such mutant viruses, and (ii) the development of diagnostics capable of assisting physicians or other clinicians in the choice of a therapeutic regimen and/or outcome prediction for a patient.

In a further preferred embodiment of the present invention, compounds of Formula (I) disclosed herein are used as tools for determining the co-receptor affinity of retroviruses including HIV and SIV, or their components, especially their envelope proteins. This affinity data can be used for several advantageous purposes, including but not limited to phenotyping a given viral population, e.g. prior to administration of anti-retroviral therapy. The affinity data may also be used to predict the progression and outcome of the infection by the virus population involved.

In another preferred embodiment of the present invention, a compound of Formula (I) is used in the preparation and execution of screening assays for compounds which modulate the activity of chemokine, especially CCR5 receptors. For example, compounds of Formula (I) as disclosed herein are useful for isolating receptor mutants, which can then be made into screening tools for the discovery of even more potent compounds, following procedures well known in the art. Furthermore, the compounds of Formula (I) are useful in establishing or characterizing the binding sites of other ligands, including compounds other than those of Formula (I) and viral envelope proteins, to chemokine receptors, e.g., by competitive inhibition. The compounds of Formula (I)

are also useful for the evaluation of putative specific modulators of various chemokine receptors. As will be appreciated by the artisan, thorough evaluation of specific agonists and antagonists of the above-described chemokine receptors has been hampered by the lack of non-peptidyl, i.e., metabolically resistant compounds with high binding affinity for these receptors. Thus, the compounds of Formula (I) are useful as products which may be commercially exploited for these and other beneficial purposes.

Included within the scope of the present invention are combinations of the compounds of Formula (I) with one or more therapeutic agents useful in the prevention or treatment of AIDS. For example, the compounds of the present invention may be effectively administered, whether at periods of pre-exposure and/or post-exposure to HIV, in combination with therapeutically effective amounts of known AIDS antivirals, immunomodulators, anti-infectives, or vaccines familiar to those skilled in the art. It will be understood that the scope of such combinations which include the compounds of Formula (I) is not limited to the above-recited list, but includes as well any combination with another pharmaceutically active agent which is useful for the prevention or treatment of HIV and AIDS.

Preferred combinations of the present invention include simultaneous, or sequential treatments with a compound of Formula (I) and one or more inhibitors of HIV protease and/or inhibitors of HIV reverse transcriptase, preferably selected from the class of non-nucleoside reverse transcriptase inhibitors (NNRTI), including but not limited to nevirapine, delavirdine, and efavirenz; from among the nucleoside/nucleotide inhibitors, including but not limited to zidovudine, didanosine, zalcitabine, stavudine, lamivudine, abscavir, and adefovir dipivoxil; and from among the protease inhibitors, including but not limited to indinavir, ritonavir, saquinavir, nelfinavir, and amprenavir. Other agents useful in the above-described preferred embodiment combinations of the present invention include current and to-be-discovered investigational drugs from any of the above classes of inhibitors, including but not limited to FTC, PMPA, fozivudine tidoxil, talviraline, S-1153, MKC-442, MSC-204, MSH-372, DMP450, PNU-140690, ABT-378, and KNI-764. There is also included within the scope of the preferred embodiments of the present invention, combinations of a compound of Formula (I) together with a supplementary therapeutic agent used for the purpose of auxiliary treatment, wherein said supplementary therapeutic agent comprises one or more members independently selected from the group consisting of proliferation inhibitors, e.g., hydroxyurea; immunomodulators, e.g., sargramostim, and various forms of interferon or interferon derivatives; fusion inhibitors, e.g., AMD3100, T-20, PRO-542, AD-349, BB-10010 and other chemokine receptor agonists/antagonists; integrase inhibitors, e.g., AR177; RNaseH inhibitors; inhibitors of viral transcription and RNA replication; and other agents that inhibit viral infection or improve the condition or outcome of HIV-infected individuals through different mechanisms.

Preferred methods of treatment of the present invention for the prevention of HIV infection, or treatment of aviremic and asymptomatic subjects potentially or effectively infected with HIV, include but are not limited to administration of a member independently selected from the group consisting of (i) a compound within the scope of Formula (I) as disclosed herein; (ii) one NNRTI in addition to a compound of (i); (iii) two NRTI in addition to a compound of (i); (iv) one NRTI in addition to the combination of (ii); and (v) a compound selected from the class of protease inhibitors used in place of an NRTI in combinations (iii) and (iv).

The preferred methods of the present invention for therapy of HIV-infected individuals with detectable viremia or abnormally low CD4 counts further include as a member to be selected: (vi) treatment according to (i) above in addition to the standard recommended initial regimens for the therapy of established HIV infections, e.g., as described in Bartlett, J. G., "1998 Medical management of HIV infection", Johns Hopkins University publishers, ISBN 0-9244-2809-0. Such standard regimens include but are not limited to an agent from the class of protease inhibitors in combination with two NRTIs; and (vii) a standard recommended initial regimens for the therapy of established HIV infections, e.g., as described in Bartlett, J. G., "1998 Medical management of HIV infection", Johns Hopkins University publishers, ISBN 0-9244-2809-0), where either the protease inhibitor component, or one or both of the NRTIs is/are replaced by a compound within the scope of Formula (I) as disclosed herein.

The preferred methods of the present invention for therapy of HIV-infected individuals that have failed antiviral therapy further include as a member to be selected: (viii) treatment according to (i) above, in addition to the standard recommended regimens for the therapy of such patients, e.g., as described in Bartlett, J. G., "1998 Medical management of HIV infection", Johns Hopkins University publishers, ISBN 0-9244-2809-0); and (ix) a standard recommended initial regimens for the therapy of patients who have failed antiretroviral therapy, e.g., as described in Bartlett, J, G., "1998 Medical management of HIV infection", Johns Hopkins University publishers, ISBN 0-9244-2809-0), where either one of the protease inhibitor components, or one or both of the NRTIs is/are replaced by a compound within the scope of Formula (I) as disclosed herein.

In the above-described preferred embodiment combinations of the present invention, the compound of Formula (I) and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

The compounds of Formula (I) may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In particular, however, the treatment of retroviral infections, and more particularly HIV, may be guided by genotyping and phenotyping the virus in the course of or prior to the initiation of administration of the therapeutic agent. In this way, it is possible to optimise dosing regimens and efficacy when administering a compound of Formula (I) for the prevention or treatment of infection by a retrovirus, in particular, the human immunodeficiency virus (HIV).

The compounds of this invention may be used for treatment of respiratory disorders, including: adult respiratory distress syndrome (ARDS), bronchitis, chronic bronchitis, chronic obstructive pulmonary disease, cystic fibrosis, asthma, emphysema, rhinitis and chronic sinusitis.

The invention is further described by means of examples, but not in any limitative sense.

The following general synthetic routes may be employed.

METHODS OF PREPARING COMPOUNDS OF THE PRESENT INVENTION

Synthesis I

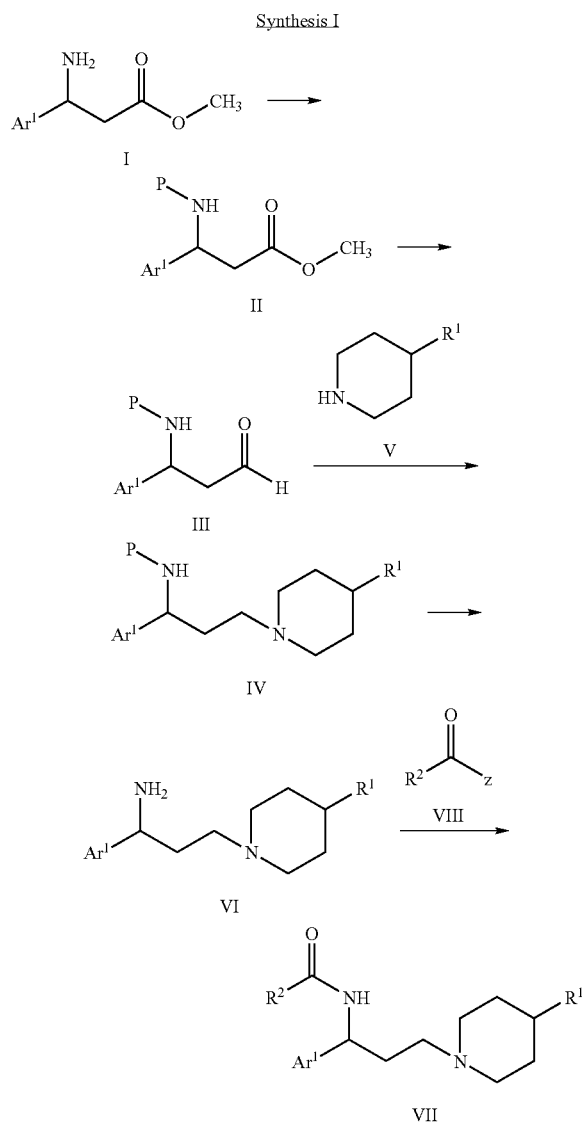

Preparation of the compounds of formula II from the amino acid derivative I where P is a suitable protecting group (preferably BOC), may be achieved for example, by reaction with di-tert-butyl dicarbonate in the presence of a base such as aqueous sodium hydroxide in a suitable solvent such as tetrahydrofuran.

Compounds of formula III may be prepared by reduction of compounds of formula II, using a suitable reducing agent, preferably diisobutylaluminium hydride in dichloromethane at −78° C.

Compounds of the general formula IV may be prepared by the reductive alkylation of an appropriate amine of formula V, with an aldehyde, of formula III. The reaction may be carried out in the presence of an excess of suitable reducing agent (e.g. sodium triacetoxyborohydride) in a probe solvent system (acetic acid in dichloromethane or 1,1,1-trichloroethane), at room temperature.

Subsequent removal of the nitrogen protecting group may be achieved using trifluoroacetic acid or hydrochloric acid in a solvent such as dioxane or dichloromethane at room temperature for from 1 to 60 hours to provide the compound of formula VI. Compounds of general formula VII may be prepared by coupling the amine of formula VI with an acid (Z=OH) or acid derivative (e.g., Z=Cl) of formula VIII using conventional amide bond forming techniques. For example, the acid VIII may be activated using a carbodiimide such as 3-(3-dimethylamino-1-propyl)-1-ethylcarbodiimide, optionally in the presence of 1-hydroxybenzotriazole hydrate. These reactions may be performed in a suitable solvent such as dichloromethane, optionally in the presence of a tertiary amine, such as triethylamine or N-ethyldiisopropylamine at about room temperature.

Alternatively an acyl chloride of formula VIII, may be reacted with an amine of formula VI in the presence of a tertiary amine, such as triethylamine or N-diisopropylethylamine in a suitable solvent such as dichloromethane at room temperature.

In a further variation a compound of formula VII, may be formed in a "one-pot procedure" by deprotection of a compound of formula IV, and coupling the resultant amine of formula VI with the acid derivative of formula VIII, using methods previously described.

When a compound of formula 1 is required as a single enantiomer it may be obtained according to the method of Davies et al. (J. Chem. Soc. Perk. Trans. I; 9; 1994;1129).

Synthesis II

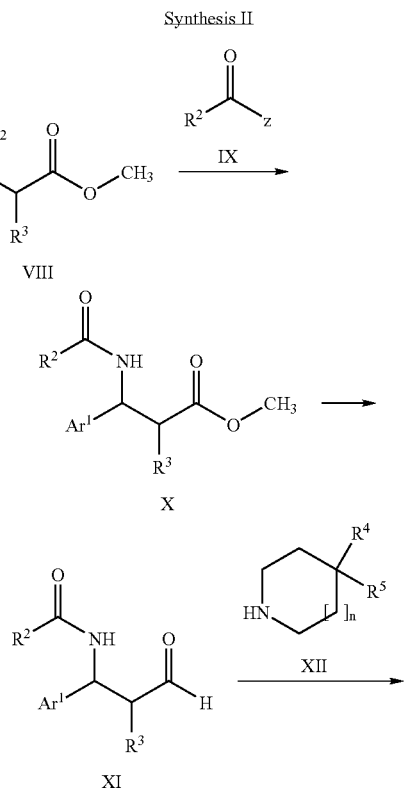

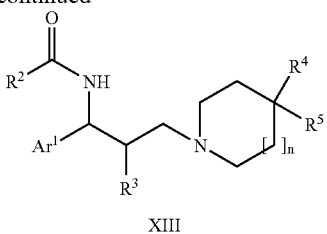

XIII n = 0 or 1

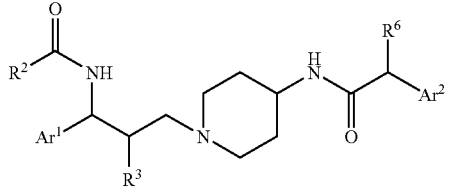

XVII

Compounds of formula X may be prepared by coupling the amino acid derivative of formula VIII with an acid (Z=OH) or acid derivative (e.g., Z=Cl) of formula IX using conventional amide bond forming techniques as described in synthesis I. R³ may be hydrogen or OH. In the case of R³=OH methylation to R³=OCH₃ may be performed using, for example, iodomethane and silver oxide in acetonitrile at reflux. Compounds of formula XI may be prepared by reduction of compounds of formula X, according to the method described in synthesis I. Reductive alkylation of the amine of formula XII, with the aldehyde of formula XI, according to the method described in synthesis I, may provide the compounds of formula XIII.

When a compound of formula VIII is required as a single enantiomer it may be obtained according to the method of Davies et al, (J. Chem. Soc. Perk. Trans. I; 9; 1994; 1129).

Compounds of the general formula XVI may be prepared by the reductive alkylation of an appropriate amine of formula XV, where P is a suitable protecting group (preferably trifluoroacetyl), with an aldehyde of formula XI. The reaction may be carried out in the presence of an excess of suitable reducing agent (e.g. sodium triacetoxyborohydride) in a protic solvent system (acetic acid in 1,1,1-trichloroethane), at room temperature.

Subsequent removal of the nitrogen protecting group in a "one-pot procedure" may be achieved using, for example, an excess of aqueous sodium hydroxide in a solvent such as ethanol at room temperature for 1 hour to provide the compound of formula XVI.

Compounds of formula XVII may be prepared by coupling the amine of formula XVI with an acid (Z=OH) or acid derivative (e.g., Z=Cl) of formula XVIII using conventional amide bond forming techniques as described in synthesis I.

Synthesis III

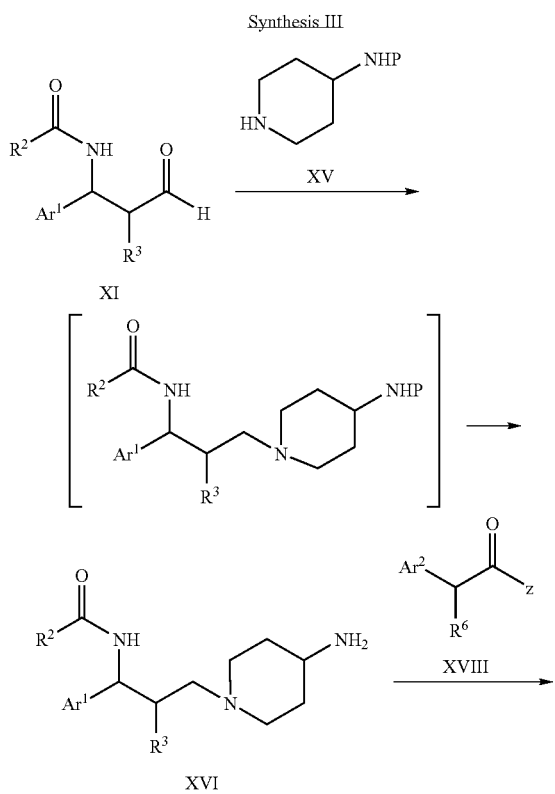

Synthesis IV

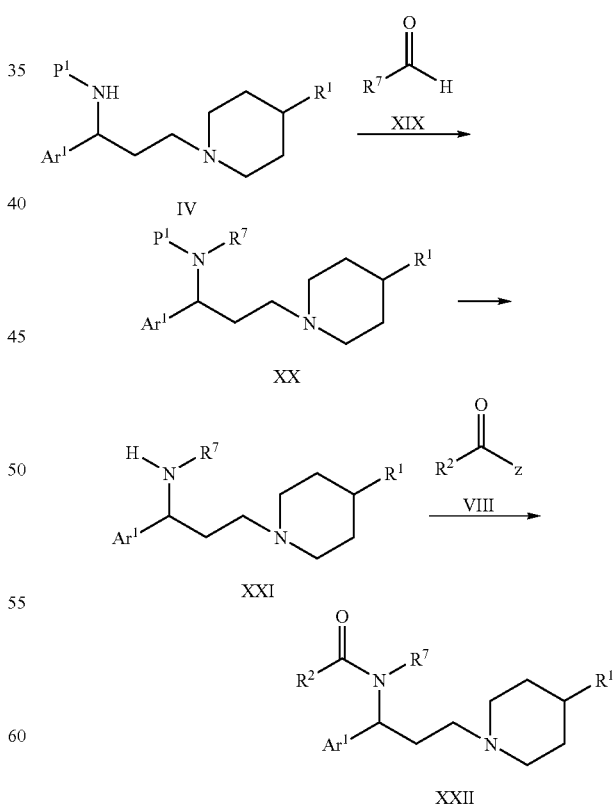

Compounds of the formula XX (R⁷ is preferably lower alkyl, for example methyl) may be prepared by reacting the protected amine (where P¹ is preferably benzyl) of formula IV, and the aldehyde of formula XIX. Typically, the reaction may be carried out with formaldehyde in formic acid and stirring the reaction mixture at 100° C. for 1 hour following the Eschweiler-Clarke procedure.

Subsequent removal of the nitrogen protecting group may be achieved under conditions of transfer hydrogenation, using a catalyst such as Pearlman's catalyst in the presence of excess ammonium formate in a suitable solvent conditions such as ethanol at reflux to provide the compound of formula XXI.

Compounds of formula XXII may be prepared by coupling the amine derivative of formula XXI with an acid (Z=OH) or acid derivative (e.g., Z=Cl) of formula VIII using conventional amide bond forming techniques as described in synthesis I.

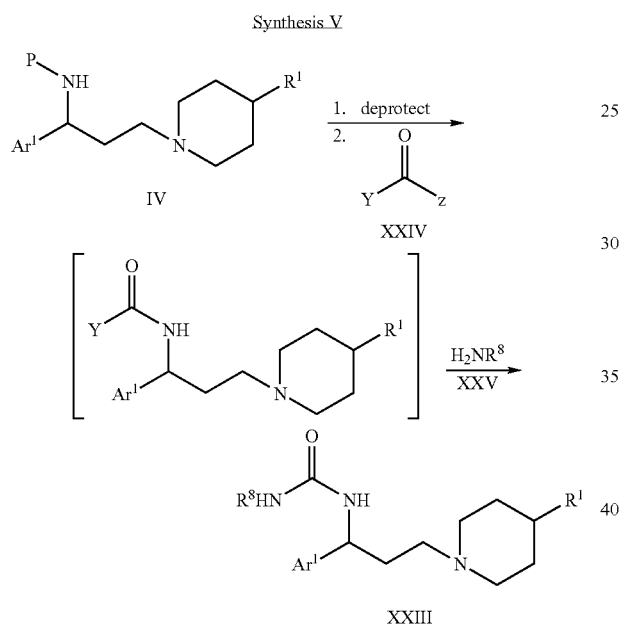

Compounds of the general formula XXIII may be prepared from the amine of formula IV by removal of the nitrogen protecting group as described in synthesis 1 and subsequent coupling with an acyl derivative (preferably Y=Z=imidazolyl), using aprotic solvents such as dichloromethane, and base, preferably imidazole, between 0° C. and room temperature over 1 hour. The intermediate may then be treated at room temperature with the amine of formula XXV, for example pyrrolidine, to yield the urea of the general structure XXIII.

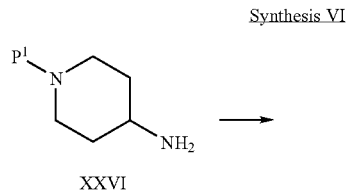

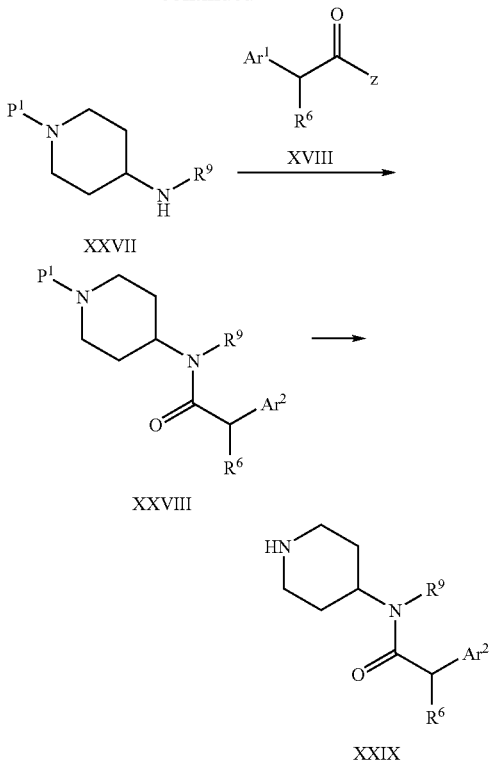

The preparations of the intermediates of the general formula V, for example compounds of substructures such as XXIX and XXXII, are described in more detail in syntheses VI and VII.

The amine of formula XXVII may be prepared from the compound of formula XXVI, where P1 is a suitable protecting group (preferably benzyl), by treatment with a carbamoyl chloride, for example benzyl chloroformate, at about 0° C. and subsequent reduction of the intermediate, using a suitable reducing agent, such as lithium aluminium hydride at reflux for 12 hours in a suitable solvent such as ether or tetrahydrofuran.

Compounds of formula XXVIII may be prepared by coupling the amine derivative of formula XXVII with an acid (Z=OH) or acid derivative (e.g., Z=Cl) of formula XVIII using conventional amide bond forming techniques as described in synthesis I.

Subsequent removal of the nitrogen protecting group may be achieved under conditions of transfer hydrogenation, using a catalyst such as Pearlman's catalyst in the presence of excess ammonium formate in a suitable solvent conditions such as ethanol at reflux to provide the compound of formula XXIX.

Synthesis VII

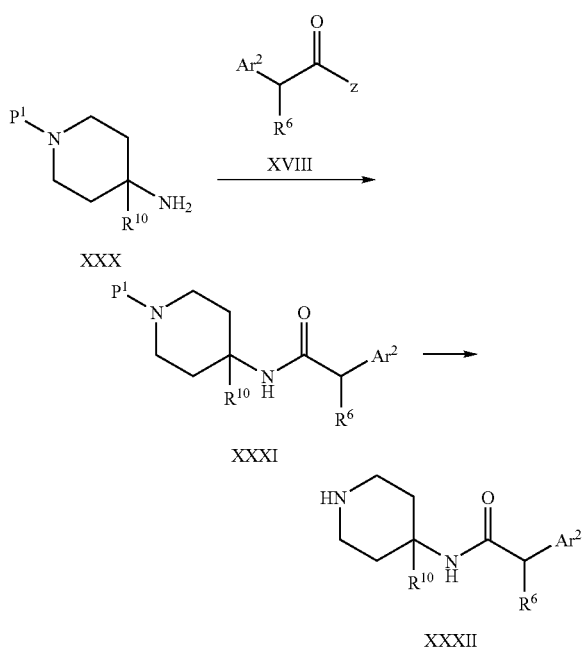

The amide derivative of formula XXXI may be prepared from compound XXX, where P¹ is a suitable protecting group (preferably benzyl), by coupling with an acid (Z=OH) or acid derivative (e.g., Z=Cl) of formula XVIII using conventional amide bond forming techniques as described in synthesis I.

Subsequent removal of the nitrogen protecting group may be achieved under conditions of transfer hydrogenation, using a catalyst such as Pearlman's catalyst in the presence of excess ammonium formate in a suitable solvent conditions such as ethanol at reflux to provide the compound of formula XXXII.

EXPERIMENTAL SECTION

PREPARATION 1

N-(1-Benzyo-4-piperidinyl)-2-phenylacetamide

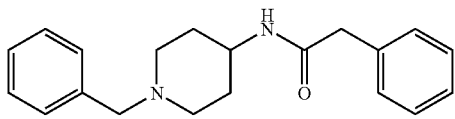

Phenacetyl chloride (7.29 ml, 55.2 mmol) was added dropwise to a diethyl ether (100 ml) solution of 1-benzyl-4-piperidinamine (10.0 g, 52.6 mmol) and triethylamine (1.60 ml, 11.5 mmol) at 0° C. The reaction mixture was stirred for 30 minutes. The solution was washed with saturated sodium bicarbonate solution, water and brine, then dried (MgSO₄), filtered and the solvent removed under reduced pressure to afford the title compound as a white solid, 16.2 g.

¹H NMR (300 MHz, CDCl3): δ [ppm] 1.23–1.39 (2H, m), 1.79–1.90 (2H, m), 2.08 (2H, t), 2.68–2.77 (2H, m), 3.45 (2H, s), 3.55 (2H, s), 3.73–3.87 (1H, m), 5.13–5.24 (1H, m), 7.20–7.39 (10H, m).

PREPARATION 2

2-Phenyl-N-(4-piperidinyl)acetamide

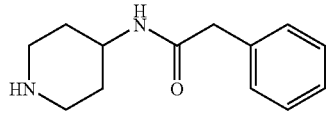

To a solution of the title compound of preparation 1 (16 g, 52 mmol) in ethanol (100 ml) was added palladium hydroxide (5 g), followed by portionwise addition of ammonium formate (16.3 g, 259 mmol). The reaction was heated to reflux for 30 minutes, then cooled and filtered through a pad of Arbocel®. The solvent was removed under reduced pressure to yield the title product as white foam, 8 g.

¹H NMR (300 MHz, CDCl₃): δ [ppm] 1.11–1.27 (2H, m), 1.81–1.90 (2H, m), 2.08 (1H, s), 2.65 (2H, t), 2.94–3.03 (2H, m), 3.55 (2H, s), 3.80–3.94 (1H, m), 5.19–5.32 (1H, m), 7.26–7.40 (5H, m).

PREPARATION 3

N-(1-Benzyl-4-piperidinyl)-2-(4-fluorophenyl)acetamide

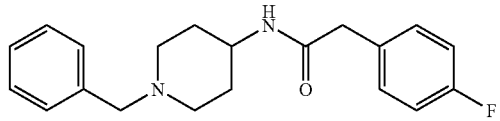

1-Benzyl-4-piperidinylamine (5 g, 26.1 mmol), 2-(4-fluorophenyl)acetic acid (4 g, 26 mmol), 1-hydroxybenzotriazole monohydrate (3.89 g, 28.6 mmol), 1-(3-dimethylaminopropyl)-3-ethyl-carbodiimide hydrochloride (6 g, 31.2 mmol) and triethylamine (4.4 ml, 31.2 mmol) were stirred together for 18 hours in dichloromethane (250 ml). The mixture was evaporated under reduced pressure and the residue dissolved in ethyl acetate before washing with water (x3). The organic layer was dried (MgSO₄), filtered and evaporated under reduced pressure to afford the title compound as a white solid, 9 g.

¹H NMR (400 MHz, CDCl₃): δ [ppm] 1.24–1.40 (2H, m), 1.77–1.87 (2H, m), 2.00–2.11 (2H, m), 2.65–2.74 (2H, m), 3.47 (2H, s), 3.48 (2H, s), 3.71–3.82 (1H, m), 5.13–5.23 (1H, m), 6.97–7.06 (2H, m), 7.16–7.32 (7H, m).

PREPARATION 4

2-(4—Fluorophenyl-N-(4-piperidinyl)acetamide

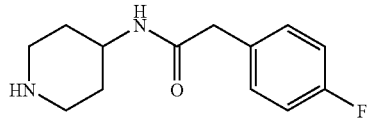

The title compound of preparation 3 (2.85 g, 8.73 mmol), ammonium formate (2.85 g, 45.2 mmol) and 20% palladium hydroxide on carbon (600 mg) were heated in ethanol (50 ml) at reflux unto gas evolution ceased. After cooling to room temperature the mixture was filtered through Arbocel® and the filtrate evaporated under reduced pressure to afford the title compound as a gum, 2.2 g.

PREPARATION 5

N-(1-Benzyl-4-piperidinyl)-2-(4-methoxyphenyl) acetamide

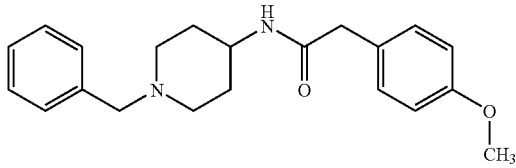

1-(3-Dimethylaminopropyl)-3-ethylcarbodiimide hydrochloride (2.42 g, 12.6 mmol) was added to a solution of 1-benzyl-4-piperidinamine (2.0 g, 10.5 mmol), 4-methoxyphenylacetic acid (1.83 g, 11.0 mmol), 1-hydroxybenzotriazole hydrate (1.56 g, 11.5 mmol) and triethylamine (2.70 ml, 26.2 mmol) in dichloromethane (100 ml). The reaction mixture was stirred for 18 hours after which time the solvent was evaporated under reduced pressure. The residue was dissolved in ethyl acetate and washed with water (3×), dried (MgSO$_4$), filtered and the solvent removed under reduced pressure to afford the title compound as a white solid, 3.44 g.

$^1$H-NMR (300 MHz, CDCl$_3$): δ [ppm] 1.22–1.40 (2H, m), 1.81 (2H, d), 2.09 (2H, t), 2.70 (2H, d), 3.45 (2H, s), 3.50 (2H, s), 3.72–3.87 (4H, m), 5.20 (1H, d) 6.88 (2H, d), 7.15 (2H, d), 7.26 (5H, m).

LRMS: m/z 339 (MH$^+$)

PREPARATION 6

2-(4-Methoxyphenyl)-N-(4-piperidinyl)acetamide

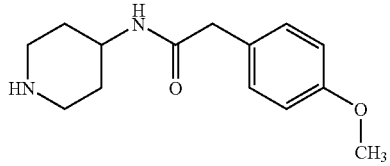

Obtained from the title compound of preparation 5 as a clear oil in 92% yield using a similar procedure to that in preparation 2.

$^1$H-NMR (300 MHz, CDCl$_3$): δ [ppm] 1.32–1.68 (2H, m), 1.88 (2H, d), 2.36 (2H, s), 2.50 (2H, t), 2.96–3.05 (2H, m), 3.46 (2H, s), 3.79–3.92 (3H, m), 5.27 (1H, d), 6.88 (2H, d), 7.15 (2H, d).

$^1$H NMR (400 MHz, CDCl$_3$): δ [ppm] 1.26–1.40 (2H, m), 1.84–1.94 (2H, m), 2.65–2.74 (2H, m), 3.03–3.11 (2H, m), 3.50 (2H, s), 3.82–3.94 (1H, m), 5.40–5.48 (1H, m), 6.98–7.05 (2H, m), 7.18–7.24 (2H, m).

PREPARATION 7

1-Benzyl-N-methyl-4-piperidinamine Hydrochloride

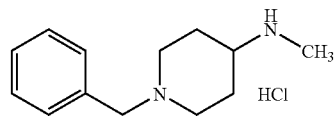

Benzyl chloroformate (4.44 g, 26.0 mmol) in ether (10 ml) was added dropwise to an ether (50 ml) solution of N-benzyl-4-piperidinamine (4.50 g, 23.6 mmol) and aqueous sodium hydrogen carbonate (50 ml) at 0° C. After addition was complete the reaction was warmed to room temperature and the layers separated, the organic layer was washed with brine, dried (MgSO$_4$), filtered and the solvent removed under reduced pressure. The residue was dissolved in tetrahydrofuran (80 ml) and lithium aluminium hydride (2.69 g, 70.8 mmol) was added portionwise and the reaction heated under reflux for 12 hours. Upon cooling to 0° C. water (4 ml) was cautiously added followed by 2N sodium hydroxide (4 ml) and the precipitate removed by filtration. The solvent was removed under reduced pressure to yield a yellow oil which was dissolved in ether (100 ml) and hydrogen chloride gas was bubbled through to give a white precipitate. Filtration furnished the title compound as a white solid, 4.30 g.

$^1$H NMR (400 MHz, CDCl$_3$): δ [ppm] 2.04 (2H, m), 2.38 (2H, d), 2.78 (3H, s), 3.18 (2H, t), 3.43 (1H, t), 3.60 (2H, d), 4.38 (2H, s), 7.45 (3H, M), 7.58 (2H, m).

LRMS: m/z 205 (MH$^+$)

PREPARATION 8

N-(1-Benzyl-4-piperidinyl)-2-(4-methoxyphenyl)-N-methylacetamide

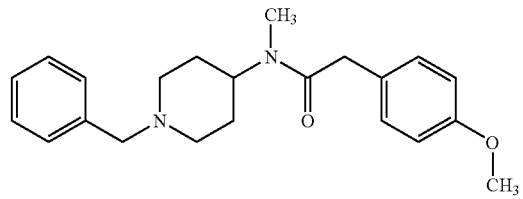

4-Methoxyphenylacetic acid (895 mg, 5.39 mmol), triethylamine (2.40 ml, 17.1 mmol) and 1-(3-dimethylaminopropy)-3-ethyl-carbodiimide hydrochloride (1.12 g, 5.88 mmol) were added to a solution of the title compound of preparation 7 (1.00 g, 4.90 mmol) in dichloromethane (20 ml). The mixture was stirred for 12 hours at room temperature, then partitioned between dichloromethane and water. The aqueous layer was separated and extracted with dichloromethane (2×). The combined organic extracts were washed with brine, dried (MgSO$_4$), filtered and evaporated under reduced pressure. The residual yellow oil was purified by column chromatography on silica gel using ethyl acetate:methanol (90:10) as eluant to afford the title compound as a clear oil, 1.26 g.

$^1$H NMR (300 MHz, CDCl$_3$): δ [ppm] 1.28–1.38 (1H, m), 1.45–1.95 (3H, m), 2.09–2.17 (1H, m), 2.81 (3H, s), 2.83–2.98 (2H, m), 3.42–3.52 (2H, m), 3.61–3.70 (2H, m), 3.78 (3H, s), 4.42–4.59 (1H, m), 6.80–6.90 (2H, m), 7.10–7.20 (2H, m), 7.20–7.37 (5H, m).

LRMS: m/z 353 (MH$^+$)

PREPARATION 9

2-(4-Methoxyphenyl)-N-methyl-N-(4-piperidinyl) acetamide

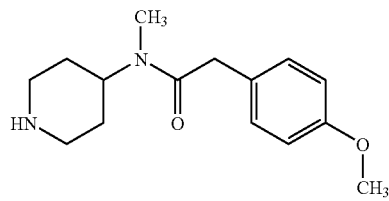

Obtained from the title compound of preparation 8 as a clear oil in 82% yield using a similar procedure to that is preparation 2.

$^1$H NMR (300 MHz, CDCl$_3$): δ [ppm] 1.23–1.35 (1H, m); 1.45–1.65 (3H, m); 2.40–2.58 (3H, m); 2.75 (3H, s); 2.99–3.15 (2H, m); 3.57–3.69 (2H, m); 3.73 (3H, s); 4.45–4.61 (1H, m); 6.79 (2H, d); 7.10 (2H, d).

LRMS: m/z 263 (MH$^+$)

PREPARATION 10

N-[(3S)-1-Benzylpyrrolidinyl]-2-(4-methoxyphenyl) acetamide

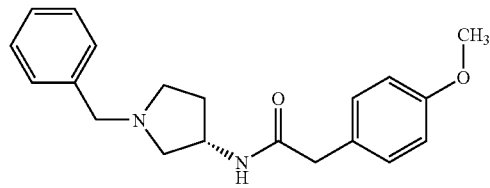

4-Methoxyphenylacetic acid (519 mg, 3.13 mmol), 1-(3-dimethylaminopropyl)-3-ethylcarbodiimide hydrochloride (651 mg, 3.39 mmol) and 1-hydroxybenzotriazole hydrate (458 mg, 3.39 mmol) were added to a solution of (3S)-1-benzyl-3-aminopyrrolidine (500 mg, 2.83 mmol) in dichloromethane (10 ml). The mixture was stirred for 12 hours at room temperature, then partitioned between dichloromethane and water. The aqueous layer was separated and extracted with dichloromethane (2×). The combined organic extracts were washed with brine, dried (MgSO$_4$), filtered and evaporated under reduced pressure to give the title compound as a pale pink solid, 600 mg.

$^1$H NMR (300 MHz, CDCl$_3$): δ [ppm] 1.43 (1H, m), 2.20 (2H, m), 2.46 (2H, m), 2.78 (1H, t), 3.47 (2H, s), 3.52 (2H, q), 3.80 (3H, s), 4.40 (1H, m), 5.78 (1H, br d), 6.87 (2H, d), 7.15–7.35 (7H, m).

LRMS: m/z 325 (MH$^+$)

PREPARATION 11

2-(4-Methoxyphenyl)-N-[(3S)-pyrrolidinyl] acetamide

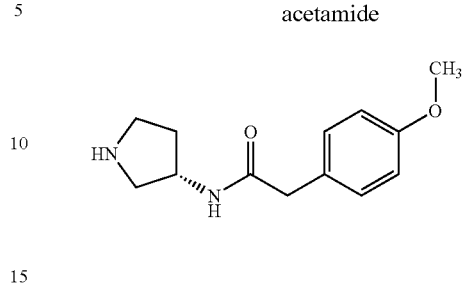

Obtained from the title compound of preparation 10 as a white solid in 98% yield using a similar procedure to that in preparation 2.

R$_F$=0.23 (dichloromethane:methanol:0.88 ammonia 80:20:1)

LRMS: m/z 235 (MH$^+$)

PREPARATION 12

N-[(3R)-1-Benzylpyrrolidinyl]-2-(4-methoxyphenyl) acetamide

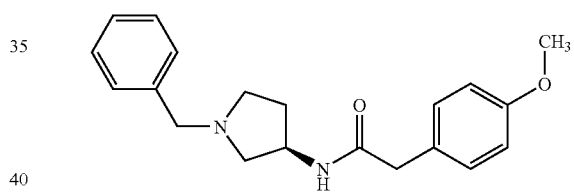

4-Methoxyphenylacetic acid (519 mg, 3.13 mmol), 1-(3-dimethylaminopropyl)-3-ethylcarbodiimide hydrochloride (651 mg, 3.39 mmol) and 1-hydroxybenzotriazole hydrate (458 mg, 3.39 mmol) were added to a solution of (3R)-1-benzyl-3-aminopyrrolidine (500 mg, 2.83 mmol) in dichloromethane (10 ml). The mixture was stirred for 12 hours at room temperature, then partitioned between dichloromethane and water. The aqueous layer was separated and extracted with dichloromethane (2×). The combined organic extracts were washed with brine, dried (MgSO$_4$), filtered and evaporated under reduced pressure. The residual pink solid was purified by column chromatography on silica gel using dichloromethane:methanol:0.88 ammonia (95:5:0.5) as eluant to afford the title compound as a white solid, 760 mg.

$^1$H NMR (400 MHz, CDCl$_3$): δ [ppm] 1.43 (1H, m), 2.20 (2H, m), 2.46 (2H, m), 2.78 (1H, t), 3.47 (2H, s), 3.52 (2H, q), 3.80 (3H, s), 4.40 (1H, m), 5.78 (1H, br d), 6.87 (2H, d), 7.15–7.35 (7H, m).

LRMS: m/z 325 (MH$^+$)

PREPARATION 11

2-(4-Methoxyphenyl)-N-[(3R)-pyrrolidinyl]acetamide

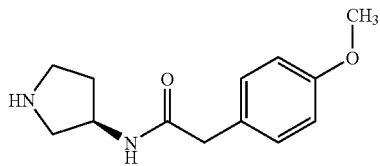

Obtained from the title compound of preparation 12 as a white solid in 92% yield using a similar procedure to that in preparation 2.

$R_F$=0.23 (dichloromethane:methanol:0.88 ammonia 80:20:1)

LRMS: m/z 235 (MH$^+$)

PREPARATION 14

N-(1-Benzyl-4-methyl-4-piperidinyl)acetamide

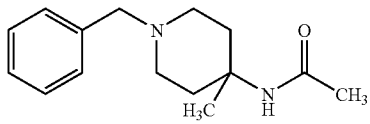

Concentrated sulphuric acid (3 ml) was added dropwise to a solution of 1-benzyl-4-methyl-4-piperidinol (640 mg, 2.56 mmol) in acetonitrile (4 ml) at 0° C. After 1 hour the reaction was cautiously poured onto 2N sodium hydroxide (20 ml), the layers separated and the aqueous extracted with dichloromethane (3×). The combined organic extracts were washed with water, brine, dried (K$_2$CO$_3$), filtered and evaporated under reduced pressure to afford the title compound as a clear oil, 600 mg.

$^1$H NMR (400 MHz, CDCl$_3$): δ [ppm] 1.38 (3H, s), 1.61–1.71 (2H, m), 1.92 (3H, s), 1.98–2.08 (2H, m), 2.18–2.24 (2H, m), 2.56–2.60 (2H, m), 3.50 (2H, s), 7.20–7.38 (5H, m).

LRMS: m/z 247 (MH$^+$)

PREPARATION 15

1-Benzyl-4-methyl-4-piperidinamine

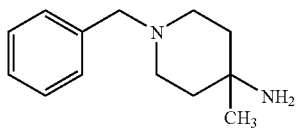

A solution of the title compound of preparation 14 (670 mg, 3.28 mmol) in concentrated hydrochloric acid (15 ml) was heated under reflux for 24 hours and then cooled. The reaction mixture was cautiously poured onto 2N sodium hydroxide (50 ml) solution and the aqueous solution extracted with dichloromethane (3×). The combined organic extracts were washed with brine, dried (MgSO$_4$), filtered and evaporated under reduced pressure to afford the title compound as a brown oil, 490 mg.

$^1$H NMR (400 MHz, CD$_3$OD): δ [ppm] 1.09 (3H, s), 1.43–1.60 (4H, m), 2.38–2.53 (4H, m), 3.51 (2H, s), 7.20–7.37 (5H, m).

LRMS: m/z 204 (MH$^+$)

PREPARATION 16

N-(1-Benzyl-4-methyl-4-piperidinyl)-2-(4-methoxyphenyl)acetamide

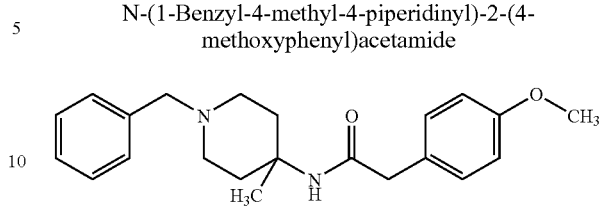

4-Methoxyphenylacetic acid (390 mg, 2.36 mmol) and 1-(3-dimethylaminopropyl)-3-ethyl-carbodiimide hydrochloride (330 mg, 1.73 mmol) were added to a solution of the title compound of preparation 15 (320 mg, 1.57 mmol) in dichloromethane (10 ml). The mixture was stirred for 12 hours at room temperature, then partitioned between dichloromethane and water. The aqueous layer was separated and extracted with dichloromethane (2×). The combined organic extracts were washed with brine, dried (MgSO$_4$), filtered and evaporated under reduced pressure. The residual yellow oil was purified by column chromatography on silica gel using an elution gradient of ethyl acetate:methanol:0.88 ammonia (100:0:0 to 95:5:0.5) to afford the title compound as a white solid, 270 mg.

$^1$H NMR (400 MHz, CDCl$_3$): δ [ppm] 1.32 (3H, s), 1.50–1.61 (2H, m), 1.82–1.98 (4H, m), 2.43–2.52 (2H, m), 3.40 (2H, s), 3.43 (2H, s), 3.81 (3H, s), 6.90 (2H, d), 7.15 (2H, d), 7.21–7.35 (5H, m).

LRMS: m/z 353 (MH$^+$)

PREPARATION 17

2-(4-Methoxyphenyl)-N-(4-methyl-4-piperidinyl)acetamide

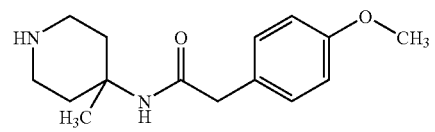

Obtained from the title compound of preparation 16 as a yellow oil in 94% yield using a similar procedure to that in preparation 2.

$^1$H NMR (400 MHz, CDCl$_3$): δ [ppm] 1.12 (3H, s), 1.41–1.52 (2H, m), 1.85–1.95 (2H, m), 2.35 (2H, br s), 2.48–2.60 (2H, m), 2.70–2.80 (2H, m), 3.42 (2H, s), 3.69 (3H, s), 6.83 (2H, d), 7.15 (2H, d).

LRMS: m/z 263 (MH$^+$)

PREPARATION 18

3-[(t-Butoxycarbonyl)amino]-3-phenylpropanoic acid

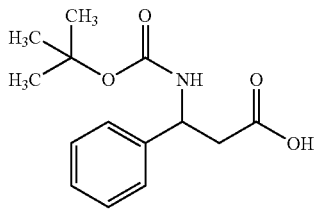

A solution of di-t-butyldicarbonate (17.1 g, 78.7 mmol) in tetrahydrofuran (60 ml) was added to a solution of DL-3-amino-3-phenylpropionic acid (10.0 g, 60.5 mmol) in aqueous 2N sodium hydroxide solution (145 ml) and the reaction stirred at room temperature for 18 hours. The reaction was diluted with water, washed with ethyl acetate (2×) and then acidified to pH 3 using concentrated hydrochloric acid. This acidic solution was extracted with ethyl acetate (2×), the combined organic extracts dried (MgSO$_4$), filtered and evaporated under reduced pressure to afford the title compound as an off-white solid, 15.3 g.

$^1$H NMR (300 MHz, CDCl$_3$): δ [ppm] 1.40 (9H, s), 2.86 (2H, br s), 5.08 (1H, br s), 7.30 (5H, m).

PREPARATION 19

Methyl-3-amino-3-phenylpropanoate Hydrochloride

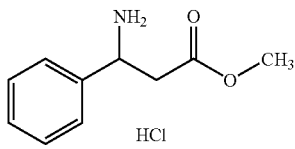

3-Phenyl-β-alanine (13.0 g, 78.8 mmol) was dissolved in methanolic hydrochloride acid (200 ml, 2.25M). The reaction mixture was heated under reflux for 18 hours, then the cooled reaction mixture was concentrated under reduced pressure to afford the title compound as a yellow oil, 16.9 g.

$^1$H-NMR (400 MHz, CD$_3$OD): δ [ppm] 3.00–3.19 (2H, m), 3.72 (3H, s), 4.74 (1H, t), 7.48 (5H, s).

PREPARATION 20

Methyl-3-[(cyclobutylcarbonyl)amino]-3-phenylpropanoate

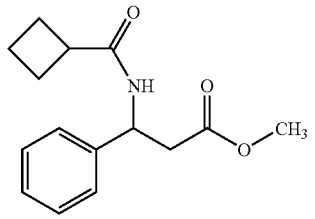

Cyclobutanecarbonyl chloride (6.91 ml, 86.7 mmol) was added dropwise to a solution of the title compound of preparation 19 (17.0 g, 78.8 mmol) and triethylamine (24.2 ml, 173.4 mmol) in dichloromethane (200 ml) at 0° C. The reaction mixture was stirred for 56 hours at room temperature after which time the mixture was washed with water then brine, dried (MgSO$_4$), filtered and the solvent removed under reduced pressure to afford the title compound as a yellow oil, 20.8 g.

$^1$H-NMR (400 MHz, CDCl$_3$): δ [ppm] 2.00–2.10 (2H, m), 2.10–2.35 (4H, m), 2.80–3.00 (2H, m), 3.03 (1H, m), 3.62 (3H, s), 5.42 (1H, m), 6.50 (1H, d), 7.25–7.35 (5H, m).

LRMS: m/z 262 (MH$^+$)

PREPARATION 21

N-(3-Oxo-1-phenylpropyl)cyclobutanecarboxamide

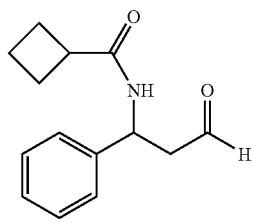

Diisobutylaluminium hydride (42.1 ml) of a 1.0M solution in dichloromethane, 42.1 mmol) was added dropwise to a solution of the title compound of preparation 20 (5.0 g, 19.1 mmol) in dichloromethane (100 ml) at −78° C. The reaction mixture was stirred at this temperature for a further 1 hour, then methanol (5 ml) precooled to −78° C. was added. The mixture was warmed to room temperature and washed with 2N hydrochloric acid, water, brine, dried (MgSO$_4$), filtered and the solvent evaporated under reduced pressure to afford the title compound as a yellow oil, 3.3 g.

$^1$H-NMR (400 MHz, CDCl$_3$): δ [ppm] 1.81–2.35 (6H, m), 2.90–3.10 (3H, m), 5.50 (1H, m), 6.00 (1H, br d), 7.23–7.39 (5H, m), 9.75 (1H, m).

LRMS: m/z 232 (MH$^+$)

PREPARATION 22

(3R)-3-[(t-Butoxycarbonyl)amino]-3-phenylpropanoic Acid

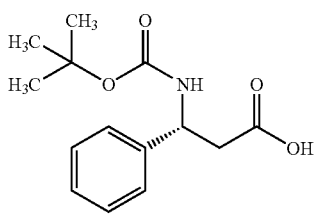

Obtained from (3R)-3-amino-3-phenylpropanoic acid as a white solid in 98% yield using a similar procedure to that in preparation 18.

$^1$H-NMR (400 MHz, CDCl$_3$): δ [ppm] 1.43 (9H, br s), 2.83 (2H, br m), 5.12 (1H, br m), 5.40 (1H, br m), 7.36 (5H, m).

PREPARATION 23

Methyl(3R)-3-[(t-butoxycarbonyl)amino]-3-phenylpropanoate

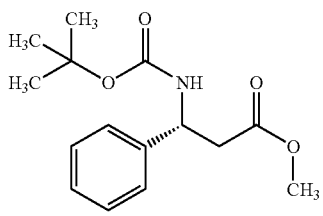

A mixture of the title compound of preparation 22 (3.1 g, 11.7 mmol), 4-dimethylaminopyridine (0.11 g, 0.90 mmol), N,N'-dicyclohexylcarbodiimide (2.5 g, 12.1 mmol) and dry methanol (1.8 ml, 44 mmol) in dichloromethane (80 ml) was stirred at room temperature for 18 hours. The mixture was filtered, the filtrate evaporated under reduced pressure and the solid re-suspended in ether. This suspension was filtered, and the filtrate evaporated under reduced pressure. The crude product was purified by column chromatography on silica gel, using an elution gradient of dichloromethane:methanol (99:1 to 95:5) to afford the title compound, 3.2 g.

$^1$H-NMR (400 MHz, CDCl$_3$): δ [ppm] 1.42 (9H, br s), 2.83 (2H, br m), 3.62 (3H, s), 5.12 (1H, br m), 5.42 (1H, br m), 7.28 (5H, m).

LRMS: m/z 280 MH$^+$)

PREPARATION 24

Methyl-(3S)-3-amino-3-phenylpropanoate

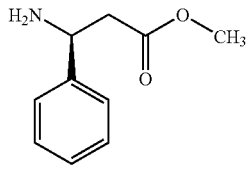

t-Butyl (3S)-3-amino-3-phenylpropanoate (1.0 g, 4.97 mmol) was dissolved in methanolic hydrochloric acid (2.25M, 25 ml). The reaction mixture was heated under reflux for 3 hours, after which time the solvent was evaporated under reduced pressure and the residue basified with aqueous saturated sodium carbonate solution. The product was then extracted using dichloromethane (x2), the combined organic layers were dried (MgSO$_4$), filtered and the solvent removed under reduced pressure to afford the title compound as a white solid, 778 mg.

$^1$H-NMR (400 MHz, CDCl$_3$): δ [ppm] 1.70 (2H, s), 2.66 (2H, d), 3.68 (3H, s), 4.43 (1H, t), 7.25–7.40 (5H, m).

PREPARATION 25

Methyl-(3S)-3-[(cyclobutylcarbonyl)amino]-3-phenylpropanoate

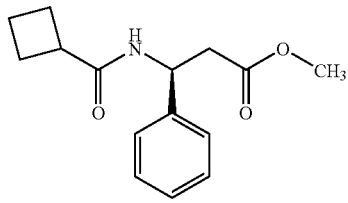

Obtained from the title compound of preparation 24 as a brown solid in 82% yield using a similar procedure to that in preparation 20. $^1$H-NMR (300 MHz, CDCl$_3$): δ [ppm] 1.81–2.06 (2H, m), 2.10–2.40 (5H, m), 2.82–3.08 (2H, m), 3.62 (3H, s), 5.42 (1H, m), 6.42 (1H, d), 7.22–7.38 (5H, m).

PREPARATION 26

N-[(1S)-3-Oxo-1-phenylpropyl]cyclobutanecarboxamide

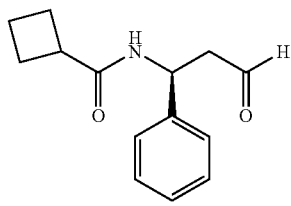

Obtained from the title compound of preparation 25 as a brown oil in 82% yield using a similar procedure to that in preparation 21.

$^1$H-NMR (300 MHz, CDCl$_3$): δ [ppm] 1.81–2.35 (6H, m), 2.90–3.10 (3H, m), 5.53 (1H, m), 5.98 (1H, br d), 7.23–7.39 (5H, m), 9.78 (1H, m).

PREPARATION 27 tert-Butyl(E)-3-(3-fluorophenyl)-2-propenoate

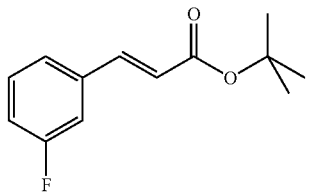

To a solution of 3-fluorobenzaldehyde (10 g, 80 mmol) in tetrahydrofuran (370 ml) was added tert-butyl 2-(triphenylphosphoranylidene)acetate (27.6 g, 73.3 mmol) in 1 g portions over 30 minutes. Upon final addition, the mixture was heated to reflux for 10 minutes. The solvent was removed under reduced pressure. The white waxy residue was triturated with pentane (x2). The pentane extracts were combined and evaporated under reduced pressure. The residue was purified by filtration through a plug of silica gel using an eluent of diethyl ether:hexane (1:2) to afford the title compound as a colorless oil, 16.2 g.

$^1$H NMR (400 MHz, CDCl$_3$): δ 1.52 (9H, s), 6.32–6.39 (1H, d), 7.00–7.06 (1H, m), 7.16–7.21 (1H, m), 7.26–7.29 (1H, m), 7.29–7.37 (1H, m), 7.48–7.55 (1H, d).

PREPARATION 28 tert-Butyl(3S)-3-(benzyl[(1R)-1-phenylethyl]amino)-3-(3-fluorophenyl)propanoate

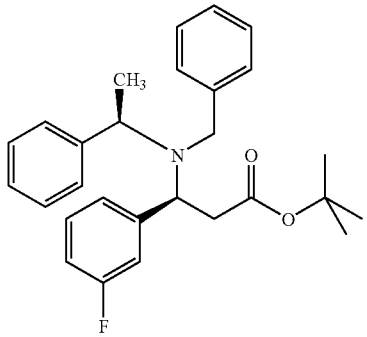

To a solution of (1R)-N-benzyl-1-phenyl-1-ethanamine (23.1 g, 109.3 mmol) in tetrahydrofuran (100 ml) at −10° C. under an atmosphere of nitrogen gas was added 1.6M n-butyl lithium in hexanes (66 ml, 105.7 mmol) dropwise. The purple solution was stirred for 15 minutes, cooled to −78° C. A solution of the title compound of preparation 27 in tetrahydrofuran (100 ml) was added dropwise. After stirring for 30 minutes, the mixture was quenched with 100 ml of saturated ammonium chloride solution and stirred to room temperature. The mixture was extracted with diethyl ether (x2). The combined organic layers were dried (MgSO$_4$), filtered and evaporated under reduced pressure. The residue was dissolved in diethyl ether and was washed with 1N citric acid (x2) and then water. The organic layer was dried (MgSO$_4$), filtered and evaporated under reduced pressure. The pale yellow oily residue was purified by column chromatography on silica gel using a gradient elution of diethyl ether:hexane (0:100 to 5:95) to afford the title compound as a colorless oil, 23.0 g.

$^1$H NMR (400 MHz, CDCl$_3$): δ [ppm] 1.19–1.32 (3H, m), 1.23 (9H, s), 2.42–2.52 (2H, m), 3.68 (2H, s), 3.90–4.00 (1H, m), 4.35–4.42 (1H, m), 6.89–6.97 (1H, m), 7.10–7.35 (11H, m), 7.35–7.42 (2H, m).

LRMS: m/z 434.5 (MH$^+$)

PREPARATION 29

Methyl (3S)-3-amino-3-(3-fluorophenyl)propanoate

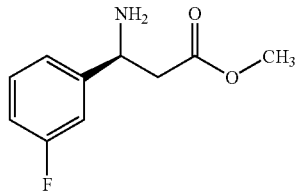

A mixture of the title compound of preparation 28 (23.0 g, 53.1 mmol), ammonium formate (33.5 g, 531 mmol) and 20% palladium hydroxide on carbon (12.5 g) were heated to reflux for 30 minutes in ethanol (300 ml). After cooling to room temperature the mixture was filtered through Arbocel® and the filtrate evaporated under reduced pressure. The residue (16.3 g, 68.1 mmol) was refluxed for 1.5 hours in a 2.25M solution of anhydrous hydrogen chloride in methanol (150 ml). The mixture was evaporated under reduced pressure and the residue was triturated with ethyl acetate to afford the title compound as a white solid, 4.4 g.

$^1$H NMR (400 MHz, CD$_3$OD): δ [ppm] 3.00–3.16 (2H, m), 3.71 (3H, s), 4.74–4.81 (1H, m), 7.13–7.23 (1H, m), 7.24–7.34 (2H, m), 7.44–7.53 (1H, m).

LRMS: m/z 198.2 (MH$^+$)

PREPARATION 30

Methyl (3S)-3-[(tert-butoxycarbonyl)amino]-3-(3-fluorophenyl)propanoate

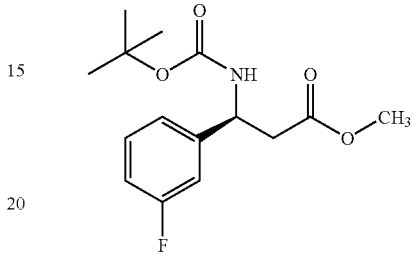

To a suspension of the title compound of preparation 29 (3.8 g, 16.3 mmol) in tetrahydrofuran (55 ml) was added di-tert-butyl dicarbonate (4.26 g, 19.5 mmol) and 18 ml of 2N aqueous sodium hydroxide. The mixture was stirred for 16 hours at room temperature. The mixture was diluted with water and extracted with diethyl ether (x3). The combined organic layers were dried (MgSO$_4$), filtered and evaporated under reduced pressure. The residue was purified by recrystalizing from hexane to afford the title compound as a white solid, 4.1 g.

$^1$H NMR (400 MHz, CHCl$_3$): δ [ppm] 1.40 (9H, s), 2.76–2.89 (2H, m), 3.63 (3H, m), 5.01–5.13 (1H, m), 5.42–5.65 (1H, bs), 6.90–6.97 (1H, m), 6.97–7.02 (1H, m), 7.03–7.10 (1H, m), 7.26–7.32 (1H, m).

PREPARATION 31

Methyl-3-amino-3-(3,4-dichlorophenyl)propanoate

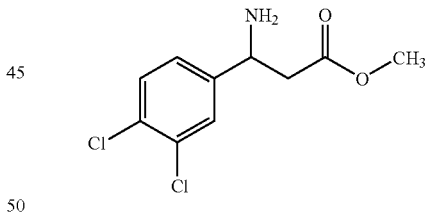

Malonic acid (7.61 g, 73.1 mmol), 3,4-dichlorobenzaldehye (12.5 g, 71.4 mmol) and ammonium acetate (11.2 g, 146.3 mmol) were heated in ethanol (15 ml) at 55° C. for 15 hours. The solvent was removed under reduced pressure and the resulting white solid was suspended in methanolic hydrochloric acid (2.25M, 100 ml) and heated under reflux for 5 hours. Upon cooling the solvent was removed under reduced pressure and the residue was suspended in water and basified to pH 8 using saturated sodium carbonate solution. The aqueous solution was extracted with dichloromethane (3x) and the combined organic extracts were washed with brine, dried (MgSO$_4$), filtered and evaporated under reduced pressure. The residual brown oil was purified by column chromatography on silica gel using ethyl acetate as eluant to afford the title compound as a cream solid, 5.72 g.

¹H-NMR (300 MHz, CDCl₃): δ [ppm] 2.61 (2H, m), 3.69 (3H, s), 4.39 (1H, t), 7.20 (1H, d), 7.40 (1H, d), 7.50 (1H, s).

LRMS: m/z 248 (MH⁺)

PREPARATIONS 32 TO 34

The compounds of the following tabulated preparations with the general formula;

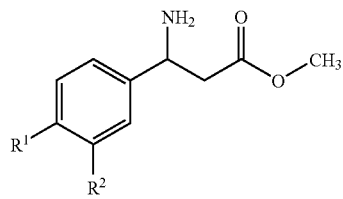

were obtained from the corresponding aldehydes using a similar procedure to that in preparation 31.

| PREP. NO. | R¹ | R² | YIELD | CHARACTERIZATION DATA |
|---|---|---|---|---|
| 32 | H | F | 49% | ¹H-NMR(300MHz, CDCl₃): δ[ppm] 1.58–1.82(2H, br m), 2.63(2H, m), 3.68(3H, s), 4.42(1H, m), 6.93(1H, m), 7.02(2H, m), 7.28(1H, m). LRMS: m/z 198(MH⁺) |
| 33 | H | Cl | 36% | ¹H-NMR(300MHz, CDCl₃): δ[ppm] 2.54–2.77(2H, m), 3.69(3H, s), 4.29–4.55(1H, m), 7.08–7.35(3H, m), 7.39 (1H, s). LRMS: m/z 214(MH⁺) |
| 34 | OMe | H | 27% | ¹H-NMR(300MHz, CDCl₃): δ[ppm] 1.80(2H, br s), 2.62(2H, d), 3.71(3H, s), 3.83(3H, s), 4.38(1H, t), 6.93(2H, d), 7.23(2H, d). |

PREPARATION 35

3-(4-Chlorophenyl)-β-alanine

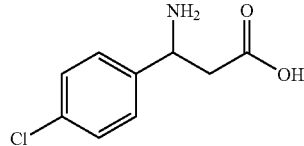

Malonic acid (7.29 g, 70.0 mmol), 4-chlorobenzaldehye (9.84 g, 70.0 mmol) and ammonium acetate (10.9 g, 140 mmol) were heated in ethanol (15 ml) at 55° C. for 15 hours. Upon cooling the solvent was removed under reduced pressure and the residue was suspended in water and basified to pH 8 using saturated sodium carbonate solution. The aqueous was extracted with dichloromethane (3×) and the combined organic extracts were washed with brine, dried (MgSO₄), filtered and evaporated under reduced pressure to afford the title compound as a cream solid, 3.48 g.

¹H-NMR (400 MHz, CF₃CO₂D): δ [ppm] 3.28–3.40 (1H, m), 3.52 (1H, m), 5.08 (1H, m), 7.47–7.55 (2H, d), 7.55–7.63 (2H, d), 11.46 (1H, s).

LRMS: m/z 200 (MH⁺)

PREPARATION 36

Methyl-3-amino-3-(4-chlorophenyl)propanoate

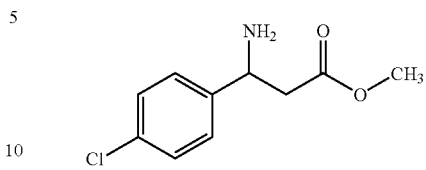

The title compound of preparation 35 (3.48 g, 17.47 mmol) was suspended in methanolic hydrochloric acid (2.25M, 100 ml) and heated under reflux for 5 hours. Upon cooling the solvent was removed under reduced pressure and the residue was suspended in water and basified to pH 8 using saturated sodium carbonate solution. The aqueous was extracted with dichloromethane (3×) and the combined organic extracts were washed with brine, dried (MgSO₄), filtered and evaporated under reduced pressure. The residual brown oil was purified by column chromatography on silica gel using ethyl acetate:hexane (80:20) as eluant to afford the title compound as a cream solid, 2.62 g.

¹H-NMR (400 MHz, CDCl₃): δ [ppm] 1.55–1.78 (2H, br s), 2.62 (2H, d), 3.68 (3H, s), 4.37–4.45 (1H, br s), 7.31 (4H, s).

LRMS: m/z 214 (MH⁺)

PREPARATION 37

Methyl-3-[(t-butoxycarbonyl)amino]-3-(4-methoxyphenyl)propanoate

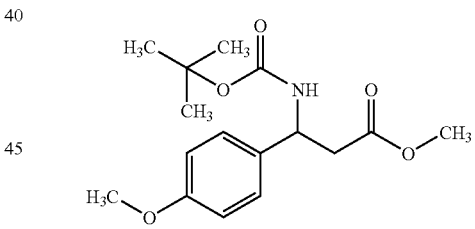

Di-t-butyl dicarbonate (2.30 g, 10.5 mmol) in dichloromethane (5 ml) was added dropwise to a solution of triethylamine (1.52 ml, 10.5 mmol) and the title compound of preparation 34 (2.00 g, 9.57 mmol) in dichloromethane (20 ml) at 0° C. The reaction was allowed to warm to room temperature and stirred for 12 hours. The solvent was removed under reduced pressure and the residue was partitioned between ethyl acetate and water and the layers separated. The organic layer was washed with brine, dried (MgSO₄), filtered and the solvent removed under reduced pressure to give a cream solid that was recrystallised from hexane to afford the title compound as a white solid, 2.15 g.

¹H NMR (300 MHz, CDCl₃): δ [ppm] 1.42 (9H, s), 2.73–2.94 (2H, m), 3.61 (3H, s), 3.79 (3H, s), 4.97–5.06 (1H, m), 5.23–5.39 (1H, br s), 6.87 (2H, d), 7.19 (2H, d).

PREPARATION 38

Methyl-3-(3,4-dichlorophenyl)-3-{[(9H-fluoren-9-ylmethoxy)carbonyl]amino}propanoate

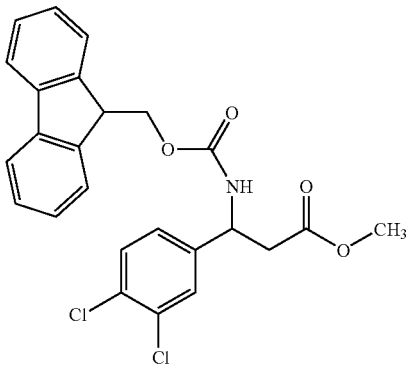

N-(9-Fluorenylmethoxycarbonyloxy)succinimide (7.07 g, 20.9 mmol) was added to a suspension of the title compound of preparation 31 (5.72 g, 23.0 mmol) and sodium hydrogencarbonate (1.94 g, 23.0 mmol) in water (140 ml) and acetone (70 ml). The reaction stirred at room temperature for 12 hours. The reaction mixture was evaporated under reduced pressure, the residue was partitioned between ethyl acetate and water and the layers separated. The organic phase was washed with brine, dried (MgSO$_4$), filtered and the solvent removed under reduced pressure to afford the title compound as a cream solid, 7.68 g.

$^1$H NMR (300 MHz, CDCl$_3$): δ [ppm] 2.70–2.97 (2H, br m), 3.65 (3H, s), 4.11–4.26 (1H, br m), 4.55–4.73 (2H, m), 5.00–5.17 (1H, br m), 5.71–5.92 (1H, br m), 7.01–7.20 (1H, br m), 7.27–7.34 (2H, m), 7.47–7.68 (2H, b), 7.68–7.84 (6H, m).

PREPARATION 39

Methyl-3-[(t-butoxycarbonyl)amino]-3-(4-chlorophenyl)propanoate

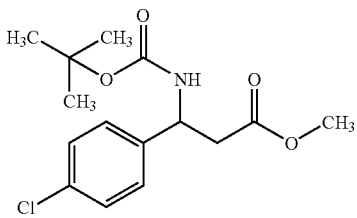

Di-t-butyl dicarbonate (11.6 g, 53.2 mmol) was added to a mixture of 2N sodium hydroxide (25 ml) and the title compound of preparation 36 (8.78 g, 41.1 mmol) in tetrahydrofuran (80 ml) at room temperature and stirred for 12 hours. The reaction mixture was evaporated under reduced pressure and the residue was partitioned between ethyl acetate and water and the layers separated. The organic phase was washed with brine, dried (MgSO$_4$), filtered and evaporated under reduced pressure to afford the title compound as a white solid, 12.51 g.

$^1$H-NMR (400 MHz, CDCl$_3$): δ [ppm] 1.42 (9H, s), 2.71–2.90 (2H, m), 3.61 (3H, s), 4.98–5.13 (1H, br s), 5.39–5.61 (1H, br m), 7.23 (2H, m).

PREPARATIONS 40 TO 41

The compounds of the following tabulated preparations with the general formula:

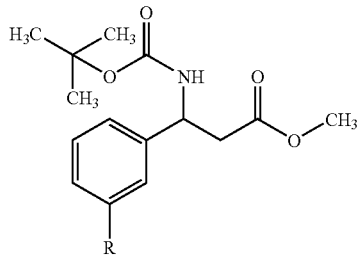

where obtained from the corresponding amines, using a similar procedure to that in preparation 39.

| PREP. NO. | R | YIELD | CHARACTERIZATION DATA |
|---|---|---|---|
| 40 | Cl | 100% | $^1$H-NMR(300MHz, CDCl$_3$): δ[ppm] 1.53(9H, s), 2.81–2.93(2H, d), 3.63(3H, s), 5.08(1H, br s), 5.56(1H, br s), 7.20(4H, m). |
| 41 | F | 100% | $^1$H-NMR(300MHz, CDCl$_3$): δ[ppm] 1.42(9H, s), 2.77–2.89(2H, d), 3.63(3H, s), 4.99–5.15(1H, br s), 6.87–7.18(3H, m), 7.24–7.35(1H, m). |

PREPARATION 42 t-Butyl-1-(4-methoxyphenyl)-3-oxopropylcarbamate

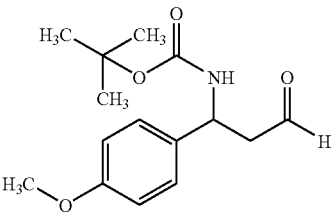

Obtained from the title compound of preparation 37 as a clear oil in 88% yield using a similar procedure to that in preparation 21.

$^1$H NMR (300 MHz, CDCl$_3$): δ [ppm] 1.42 (9H, s), 2.82–3.03 (2H, m), 3.81 (3H, s), 4.94–5.03 (1H, br s), 5.06–5.19 (1H, m), 6.87 (2H, d), 7.23 (2H, d), 9.74 (1H, s).

PREPARATIONS 43 TO 45

The compounds of the following tabulated examples with the general formula:

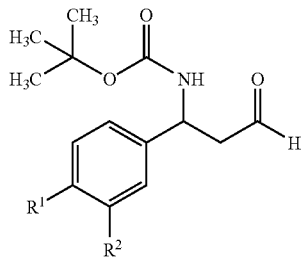

were obtained from the corresponding methyl esters, using a similar procedure to that in preparation 21.

| PREP. NO. | R¹ | R² | YIELD | CHARACTERIZATION DATA |
|---|---|---|---|---|
| 43 | H | F | 83% | ¹H-NMR(300MHz, CDCl₃): δ[ppm] 1.42(9H, s), 2.98(2H, m), 5.03–5.26 (2H, br m), 6.98(3H, m), 7.30(1H, m), 9.74(1H, s). |
| 44 | H | Cl | 85% | ¹H-NMR(300MHz, CDCl₃): δ[ppm] 1.43(9H, s), 2.87–3.03(2H, br m), 5.09 (2H, br s), 7.20(4H, m), 9.76(1H, s). |
| 45 | Cl | H | 92% | ¹H NMR(300MHz, CDCl₃): δ[ppm] 1.42(9H, s), 2.83–3.00(2H, m), 5.00–5.21(1H, br m), 7.17–7.28 (4H, m), 9.73(1H, s). |

PREPARATION 46

9H-Fluoren-9-ylmethyl-1-(3,4-dichlorophenyl)-3-oxopropylcarbamate

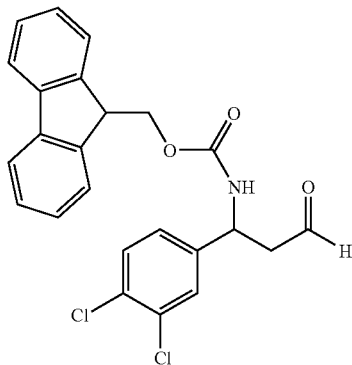

Obtained from the title compound of preparation 38 as a clear oil in 62% yield using a similar procedure to that in preparation 21.

¹H-NMR (300 MHz, CDCl₃): δ [ppm] 2.85–3.13 (2H, br s), 4.14 (1H, m), 4.53 (2H, m), 5.06–5.24 (1H, br s), 5.28–5.48 (1H, br s), 6.93–7.17 (1H, br s), 7.28 (2H, m), 7.39 (4H, m), 7.58 (2H, m), 7.66 (2H, m), 9.68 (1H, s).

LRMS: m/z 440 (MH⁺)

PREPARATION 47 tert-Butyl (2R,3R)-3-{benzyl[(1R)-1-phenylethyl]amino}-2-hydroxy-3-phenylpropanoate

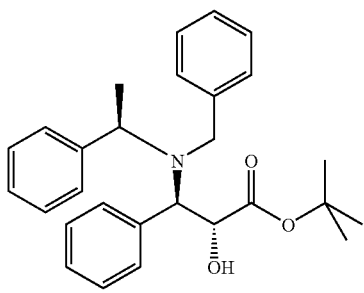

To a solution of (1R)-N-benzyl-1-phenyl-1-ethanamine (16.6 g, 79 mmol) in tetrahydrofuran (200 ml) at –10° C. was added n-butyl lithium (46 ml of a 1.6M solution in hexane, 74 mmol) dropwise. The purple solution was stirred for 15 minutes, cooled to –78° C. and a solution of tert-butylcinnamate (10.0 g, 49 mmol) in tetrahydrofuran (100 ml) added dropwise. After stirring for 2 hours (–)-camphorsulphonyl oxaziridine (18 g, 79 mmol) was added portionwise and the reaction stirred at –78° C. for 1 hour. The reaction was warmed to room temperature and saturated aqueous ammonium chloride solution added and the solvent removed under reduced pressure. The remaining aqueous mixture was extracted with dichloromethane (x2) and the combined organic layers were dried (MgSO₄), filtered and evaporated under reduced pressure. The residue was dissolved in diethyl ether, filtered and the filtrate washed with water, dried (MgSO₄), filtered and evaporated under reduced pressure. The pale yellow oily residue was purified by column chromatography on silica gel using a gradient elution of diethyl ether:hexane (0:100 to 10:90) to afford the title compound as a colourless oil, 10.0 g.

¹H NMR (300 MHz, CDCl₃): δ [ppm] 1.23 (12H, m), 2.78 (1H, d), 3.81 (1H, d), 4.11 (1H, d), 4.18 (1H, d), 4.20 (1H, d), 4.39 (1H, m), 7.15–7.50 (15H, m)

LRMS: m/z 432.0 (MH⁺)

PREPARATION 48 tert-Butyl (2R,3R)-3-amino-2-hydroxy-3-phenylpropanoate

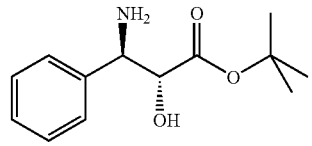

A mixture of the title compound of preparation 47 (650 mg, 1.50 mmol), ammonium formate (481 mg, 7.52 mmol) and 20% palladium hydroxide on carbon (500 mg) were heated under reflux in ethanol for 30 minutes (10 ml). The reaction was cooled and filtered through Arbocel® and the filtrate evaporated under reduced pressure to afford the title compound as a brown oil, 355 mg.

¹H NMR (400 MHz, CDCl₃): δ [ppm] 1.23 (9H, s), 4.45 (1H, bs), 4.60 (1H, bs), 7.20–7.35 (5H, m), 8.60 (3H, bs)

LRMS: m/z 238.1 (MH⁺)

PREPARATION 49

Methyl (2R,3R)-3-amino-2-hydroxy-3-phenylpropanoate Hydrochloride

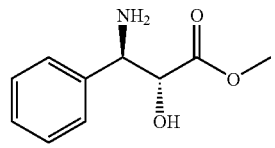

The title compound of preparation 48 (1.00 g, 4.21 mmol) was heated under reflux in methanolic hydrochloric acid (50 ml, 2.25M) for 1 hour. The mixture was cooled and the solvent evaporated under reduced pressure to afford the title compound as a brown oil, 950 mg.

¹H NMR (400 MHz, CD₃OD): δ [ppm] 3.60 (3H, s), 4.65 (1H, bs), 4.78 (1H, bs), 7.38–7.55 (5H, m)

LRMS: m/z 196.9 (MH⁺)

PREPARATION 50

Methyl (2R,3R)-3-[(cyclobutylcarbonyl)amino]-2-hydroxy-3-phenylpropanoate

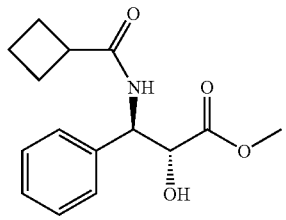

Cyclobutanecarbonyl chloride (0.65 ml, 5.19 mmol) was added dropwise to a solution of the title compound of preparation 49 (920 mg, 4.72 mmol) and triethylamine (1.58 ml, 11.3 mmol) in dichloromethane (20 ml) at 0° C. The reaction mixture was stirred for 2 hours at room temperature after which time the mixture was washed with water then brine, dried (MgSO$_4$), filtered and the solvent removed under reduced pressure to afford the title compound as a yellow oil, 1.23 g.

$^1$H-NMR (400 MHz, CDCl$_3$): δ [ppm] 2.00 (2H, m), 2.10–2.35 (4H, m), 3.08 (1H, m), 3.25 (1H, m), 3.62 (3H, s), 4.59 (1H, m), 5.42 (1H, dd), 6.30 (1H, d), 7.25–7.35 (5H, m)

LRMS: m/z 279.0 (MH$^+$)

PREPARATION 51

Methyl (2R,3R)-3-[(cyclobutylcarbonyl)amino]-2-methoxy-3-phenylpropanoate

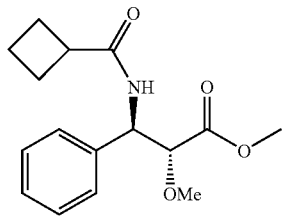

The title compound of preparation 50 (1.00 g, 3.61 mmol), silver oxide (917 mg, 3.97 mmol) and iodomethane (1.79 ml, 28.8 mmol) were heated under reflux in acetonitrile (20 ml) for 24 hours. The reaction was cooled and filtered through Arbocel® and the filtrate evaporated under reduced pressure. The residue was purified by flash column chromatography on silica gel using ethyl acetate:hexane (70:30) as eluant to afford the titl compound as a white solid, 470 mg.

$^1$H NMR (400 MHz, CDCl$_3$): δ [ppm] 1.90 (2H, m), 2.10–2.35 (4H, m), 3.08 (1H, m), 3.38 (3H, s), 3.79 (3H, s), 4.07 (1H, d), 5.42 (1H, dd), 6.30 (1H, d), 7.25–7.35 (5H, m)

LRMS: m/z 314.0 (MNa$^+$)

PREPARATION 52 t-Butyl-3-(4-{[2-(4-methoxyphenyl)acetyl]amino}-1-piperidinyl)-1-(4-methoxyphenyl)propylcarbamate

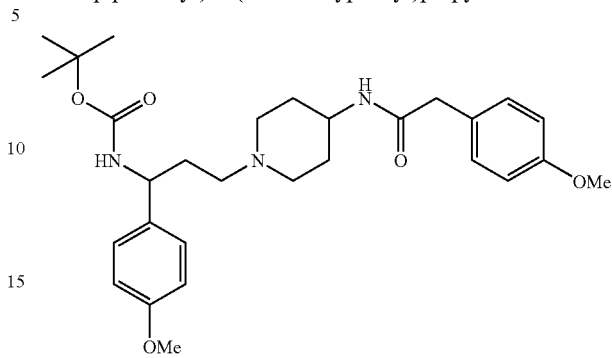

The title compound of preparation 6 (444 mg, 1.79 mmol) was dissolved in dichloromethane/acetic acid (20 ml, 10% solution) and the title compound of preparation 42 (500 mg, 1.79 mmol) was added followed by sodium triacetoxyborohydride (570 mg, 2.69 mmol). The reaction mixture was stirred for 18 hours after which time the solution was basified using saturated aqueous sodium carbonate and the product was extracted using dichloromethane (x3). The combined organic extracts were dried (MgSO$_4$) and the solvent evaporated under reduced pressure to give a brown oil This was purified by column chromatography on silica gel using dichloromethane:methanol:0.88 ammonia (98:2:0.25) as eluant to afford the title compound as a clear oil, 800 mg.

PREPARATIONS 53–55

The compounds of the following tabulated examples with the general formula:

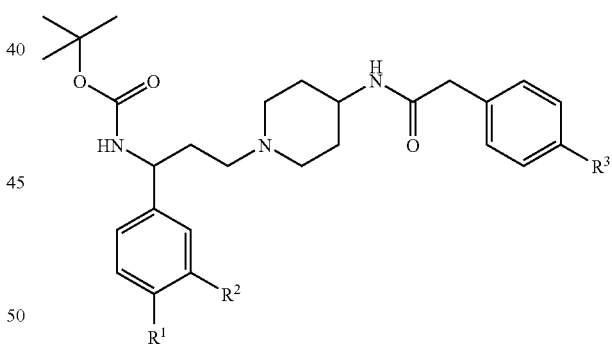

were obtained from the corresponding aldehydes, using a similar procedure to that in preparation 52.

| PREP. NO. | R1 | R2 | R3 | YIELD | CHARACTERIZATION DATA |
|---|---|---|---|---|---|
| 53 | H | Cl | H | | $^1$H NMR(400MHz, CDCl$_3$): δ [ppm] 1.18–1.42(11H, m), 1.66(1H, bs), 1.92–2.16(5H, m), 2.20–2.36(2H, m), 2.63(1H, bs), 2.79(1H, bs), 3.58 (2H, s), 3.80(1H, m), 4.73(1H, bs), 5.18 (1H, bs), 6.80(1H, bs), 7.08(1H, d), 7.11–7.28 (8H, m). LRMS: m/z 486(MH$^+$) |

-continued

| PREP. NO. | R1 | R2 | R3 | YIELD | CHARACTERIZATION DATA |
|---|---|---|---|---|---|
| 54 | H | F | H | | $^1$H NMR(400MHz, CDCl$_3$): δ [ppm] 1.20–1.45(11H, bs), 1.61–1.77 (1H, bs), 1.82–2.14(5H, m), 2.18–2.37 (2H, m), 2.55–2.70(1H, bs), 2.71–2.94 (1H, bs), 3.55(2H, s), 3.71–3.85(1H, m), 4.66–4.83(1H, bs), 5.06–5.26(1H, bs), 6.72–6.85(1H, m), 6.85–7.05(3H, m), 7.23–7.40(6H, m). LRMS: m/z 470(MH$^+$) |
| 55 | Cl | H | H | | $^1$H NMR(400MHz, CDCl$_3$): δ [ppm] 1.20–1.45(10H, bs), 1.60–1.79 (1H, bs), 1.82–2.15(6H, m), 2.19–2.36 (2H, m), 2.55–2.71(1H, bs), 2.71–2.94 (1H, bs), 3.56(2H, s), 3.71–3.87(1H, bm), 4.60–4.80(1H, bs), 5.09–5.25(1H, bs), 6.67–6.85(1H, bs), 7.18(1H, d), 7.20–7.40(8H, m). LRMS: m/z 486(MH$^+$) |

PREPARATION 56 tert-Butyl (1S)-1-(3-fluorophenyl)-3-{4-[(2-phenylacetyl)amino]-1-piperidinyl}propylcarbamate

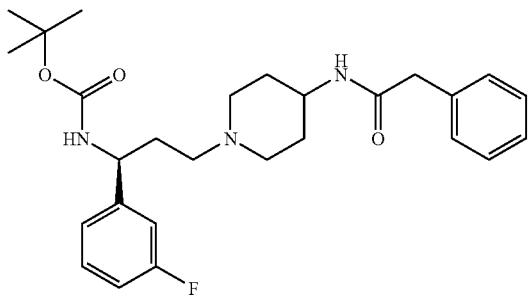

To a solution of the title compound of preparation 30 (1.64 g, 5.52 mmol) in dichloromethane (30 ml) at −78° C. under an atmosphere of nitrogen was added dropwise a 1M solution of diisobutylaluminium hydride in dichloromethane (11.6 ml, 11.6 mmol). After 30 minutes the mixture was quenched with methanol at −78° C. (4 ml). The mixture was poured in 30 ml of 2M aqueous hydrochloric acid and extracted with dichloromethane (x2). The combined organic layers were dried (MgSO$_4$), filtered and evaporated under reduced pressure. The residue (735 mg, 2.75 mmol), the title compound of preparation 2 (600 mg, 2.75 mmol) and sodium triacetoxyborohydride (875 mg, 4.12 mmol) were stirred together for 20 minutes in glacial a 30 ml mixture of acetic acid:dichloromethane (1:10). The solvents were removed under reduced pressure and the residue basified with saturated sodium carbonate solution before extracting with dichloromethane (x2). The organic layers were combined and dried (MgSO$_4$), filtered and evaporated under reduced pressure to afford the title compound as a white foam, 1.20 g.

$^1$H NMR (400 MHz, CHCl$_3$): δ [ppm] 1.24–1.40 (11H, m), 1.81–2.11 (6H, m), 2.18–2.32 (2H, m), 2.58–2.69 (1H, m), 2.69–2.85 (1H, m), 3.55 (2H, s), 3.71–3.85 (1H, m), 4.68–4.80 (1H, m), 5.13–5.24 (1H, m), 6.73–6.84 (1H, m), 6.84–6.97 (2H, m), 6.97–7.03 (1H, m), 7.20–7.39 (6H, m).

LRMS: m/z 470.1 (MH+)

PREPARATION 57 tert-Butyl(1S)-1-(3-fluorophenyl)-3-(4-{[2-(4-fluorophenyl)acetyl]amino}-1-piperidinyl) propylcarbamate

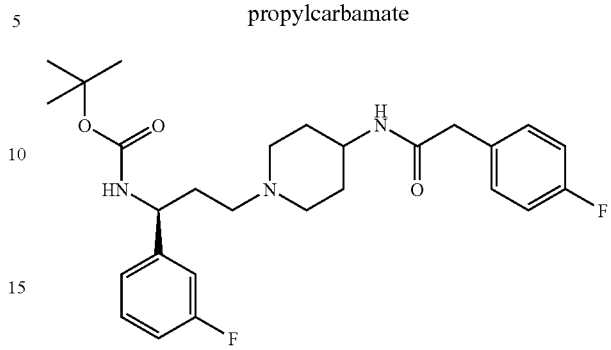

To a solution of the title compound of preparation 30 (2.52 g, 8.48 mmol) in dichloromethane (50 ml) at −78° C. under an atmosphere of nitrogen was added dropwise a 1M solution of diisobutylaluminium hydride in dichloromethane (17.8 g, 17.8 mmol). After 30 minutes the mixture was quenched with methanol at −78° C. (7 ml). The mixture was poured in 40 ml of 2M aqueous hydrochloric acid and extracted with dichloromethane (x2). The combined organic layers were dried (MgSO$_4$), filtered and evaporated under reduced pressure. The residue (1.13 g, 4.23 mmol), the title compound of preparation 4 (1 g, 4.23 mmol) and sodium triacetoxyborohydride (1.35 g, 6.37 mmol) were stirred together for 30 minutes in a 20 ml mixture of glacial acetic acid:dichloromethane (1:10). The mixture was evaporated under reduced pressure and basified with saturated sodium carbonate solution before extracting with ethyl acetate. The organic layer was washed with water, dried (MgSO$_4$), filtered and evaporated under reduced pressure to afford the title compound as a foam, 1.73 g.

$^1$H NMR (300 MHz, CDCl$_3$): δ [ppm] 1.29–1.48 (9H, m), 1.60–2.15 (8H, m), 2.20–2.40 (2H, m), 2.60–2.79 (1H, m), 2.79–2.90 (1H, m), 3.50 (2H, s), 3.65–3.87 (2H, m), 4.68–4.82 (1H, m), 5.13–5.29 (1H, m), 6.65–6.80 (1H, m), 6.85–7.10 (4H, m), 7.16–7.35 (3H, m).

PREPARATION 58 t-Butyl(1R)-3-(4-{[2-(4-methoxyphenyl)acetyl]amino}-1-piperidinyl)-1-phenylpropylcarbamate

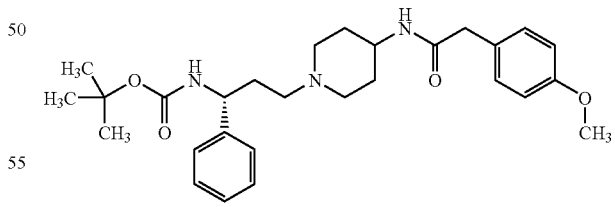

Diisobutylaluminium hydride (24.0 ml of a 1.0M solution in dichloromethane, 24.0 mmol) was added dropwise to a solution of the title compound of preparation 23 (3.2 g, 11.1 mmol) in dichloromethane (100 ml) at −78° C. The reaction mixture was stirred at this temperature for a further 1 hour. Methanol (5 ml) precooled to −78° C. was then added and the mixture was warmed to room temperature and washed with 2N hydrochloric acid, water, brine, dried (MgSO$_4$), filtered and the solvent removed under reduced pressure to afford a yellow oil. The oil was dissolved in dichloromethane/acetic acid (50 ml, 10% solution) and th title compound of preparation 9 (3.0 g, 12.2 mmol) was added followed by sodium triacetoxyborohydride (3.5 g, 16.7 mmol). The reaction mixture was stirred for 30 minutes after which time the solution was basified using saturated aqueous sodium carbonate and the product was extracted using dichloromethane (×3). The combined organic extracts were dried (MgSO₄) and the solvent evaporated under reduced pressure to give a brown oil. This was purified by column chromatography on silica gel using dichloromethane:methanol:0.88 ammonia (95:5:0.5) as eluant to afford the title compound as a clear oil, 4.2 g.

LRMS: m/z 482 (MH⁺)

PREPARATION 59

9H-Fluoren-9-ylmethyl 1-(3,4-dichlorophenyl)-3-(4-{[2-(4-methoxy-phenyl)acetyl]amino}-1-piperidinyl) propylcarbamate

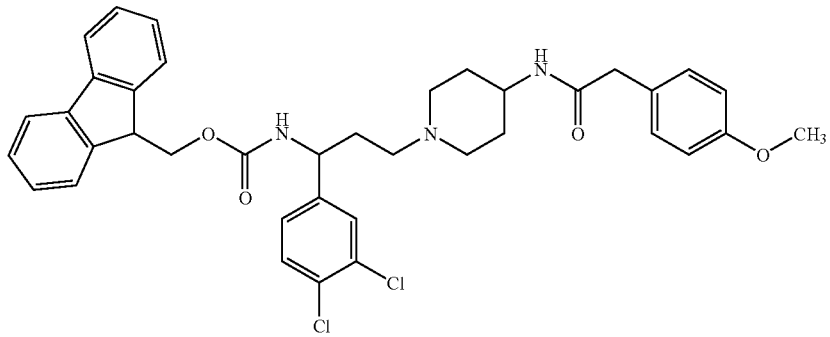

Obtained from the title compounds of preparation 46 and preparation 9 as a clear oil in 9% yield using a similar procedure to that in preparation 52.

¹H NMR (300 MHz, CDCl₃): δ [ppm] 1.15–1.42 (2H, m), 1.46–1.76 (2H, m), 1.80–2.16 (5H, m), 2.26 (2H, m), 2.60–2.90 (2H, m), 3.48 (2H, s), 2.60–2.88 (4H, m), 4.16 (1H, m), 4.32–4.56 (2H, m), 4.76 (1H, m), 5.19 (1H, m), 6.69–6.92 (3H, m), 6.94–7.21 (5H, m), 7.26–7.45 (4H, m), 7.57 (2H, m), 7.64–7.82 (1H, m).

LRMS: m/z 672 (MH⁺)

PREPARATION 60

N-{1-[(3S)-3-[Benzyl(methyl)amino]-3-(3-fluorophenyl)propyl]-4-piperidinyl}-2-(4-fluorophenyl)acetamide

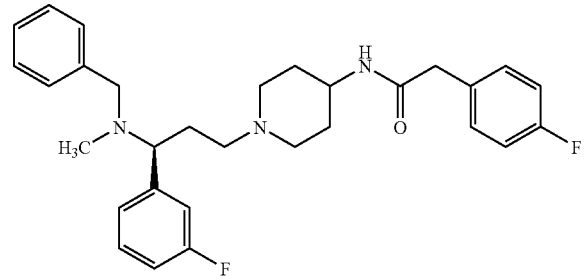

The title compound of preparation 57 (1.73 g, 3.55 mmol) was stirred for 30 minutes in a mixtur of trifluoroacetic acid:dichloromethane (34 ml, 1:1). The mixture was evaporated under reduced pressure and basified with saturated sodium carbonate solution before extracting with dichloromethane (×3). The organic layers were combined and dried (MgSO₄), filtered and evaporated under reduced pressure. The residue was purified by column chromatography on silica gel using an eluent of dichloromethane:methaniol:0.88 ammonia (90:10:1). The residue (250 mg, 0.65 mmol), benzaldehyde (70 mg, 0.65 mmol) and sodium triacetoxyborohydride (175 mg, 0.78 mmol) were stirred together for 15 minutes in a mixture of glacial acetic acid:dichloromethane (10 ml, 1:10). The mixture was evaporated under reduced pressure and basified with saturated sodium carbonate solution before extracting with dichloromethane (×3). The organic layers were combined and dried (MgSO₄), filtered and evaporated under reduced pressure. The residue was heated for 1 hour at 100° C. in a 6 ml mixture of formic acid:formaldehyde (1:2). The mixture was evaporated under reduced pressure and basified with saturated sodium carbonate solution before extracting with dichloromethane (×3). the organic layers were combined and dried (MgSO₄), filtered and evaporated under reduced pressure. The residue was purified by column chromatography on silica gel using an elution gradient of dichloromethane:methanol:0.88 ammonia (98:2:0.25 to 95:5:0.5) to afford the title compound an a gum, 260 mg.

¹H NMR (400 MHz, CDCl₃): δ [ppm] 1.23–1.58 (2H, m), 1.81–1.90 (3H, m), 1.94–2.21 (4H, m), 2.06 (3H, s), 2.26–2.35 (1H, m), 2.61–2.74 (2H, m), 3.20–3.26 (1H, m), 3.48 (2H, s), 3.49–3.60 (2H, m), 3.68–3.80 (1H, m), 5.11–5.20 (1H, m), 6.90–7.06 (5H, m), 7.16–7.32 (8H, m).

LRMS: m/z 492.2 (MH+).

PREPARATION 61

N-(1-[(3R)-3-amino-3-phenylpropyl]-4-piperidinyl)-2-(4-methoxyphenyl)acetamide

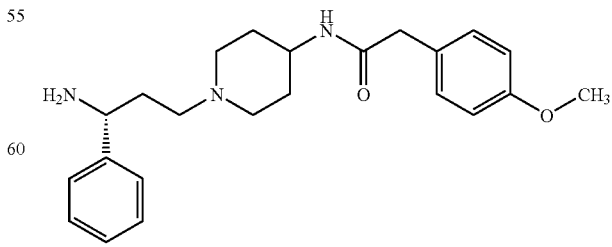

Trifluoroacetic acid (2 ml) was added dropwise to a solution of the title compound of preparation 58 (670 mg, 1.39 mmol) in dichloromethane (10 ml). The reaction was stirred at room temperature for 0.5 hours, then heated to reflux for 15 minutes. After cooling to room temperature more trifluoroacetic acid (2 ml) was added and the reaction was refluxed for further 10 minutes. After cooling to room temperature the reaction mixture was concentrated under reduced pressure. The residue was dissolved in dichloromethane, then washed with aqueous sodium carbonate solution. The organic layer was dried (MgSO$_4$), filtered and evaporated under reduced pressure. The residue was purified by column chromatography on silica gel, using an elution gradient of dichloromethane:methanol:0.88 ammonia (95:5:0.5 to 90:10:1) to afford the title compound as a white solid, 200 mg.

$^1$H NMR (400 MHz, CDCl$_3$): δ [ppm] 1.23–1.35 (2H, m), 1.74–1.87 (4H, m), 1.94–2.06 (2H, m), 2.20–2.29 (1H, m), 2.29–2.37 (1H, m), 2.64–2.77 (2H, m), 3.48 (2H, s), 3.68–3.84 (1H, m), 3.81 (3H, s), 3.94 (1H, m), 5.18 (1H, d), 6.87 (2H, d), 7.13 (2H, d), 7.19–7.35 (5H, m).

PREPARATIONS 62 TO 65

The compounds of the following tabulated examples with the general formula:

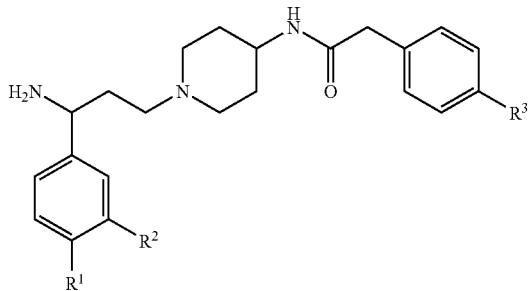

were obtained from the corresponding t-butyl carbamates, using a similar procedure to that in preparation 61.

| PREP. NO. | R1 | R2 | R3 | YIELD | CHARACTERIZATION DATA |
|---|---|---|---|---|---|
| 62 | OMe | H | OMe | 64% | $^1$H NMR(400MHz, CDCl$_3$): δ [ppm] 1.23–1.35(2H, m), 1.71–1.87(4H, m), 1.94–2.06(2H, m), 2.16–2.26(1H, m), 2.26–2.35(1H, m), 2.65–2.77(2H, m), 3.47(1H, m), 3.69–3.80(1H, m), 3.77(3H, s), 3.81(3H, s), 3.89(1H, t), 5.20 (1H, d), 6.81–6.90(4H, m), 7.13 (2H, d), 7.19(2H, d). |
| 63 | H | Cl | H | 73% | $^1$H NMR(400MHz, CDCl$_3$): δ [ppm] 1.42(2H, m), 1.91(4H, m), 2.06(2H, m), 2.40(2H, m), 2.60 (2H, br s), 2.78(2H, br m), 3.58 (2H, s), 3.79(1H, m), 3.98(1H, t), 5.38(1H, br d), 7.10–7.28(9H, m). LRMS: m/z 386(MH$^+$) |
| 64 | H | F | H | 79% | $^1$H NMR(400MHz, CDCl$_3$): δ [ppm] 1.20–1.35(3H, m), 1.68–1.89(5H, m), 2.02(2H, q), 2.30 (2H, m), 2.70(2H, t), 3.35(2H, s), 3.76(1H, m), 3.95(1H, t), 5.17(1H, d), 6.85–6.94(1H, m), 6.97–7.09 (2H, m), 7.20–7.39(6H, m). LRMS: m/z 369(MH$^+$) |
| 65 | Cl | H | H | 69% | $^1$H NMR(400MHz, CDCl$_3$): δ [ppm] 1.29(2H, m), 1.65–1.90(4H, m), 2.00(2H, m), 2.19–2.47(2H, m), 2.68(2H, br t), 3.53(2H, s), 3.76(1H, br m), 3.94(1H, t), 5.16 (1H, d), 7.11–7.40(9H, m). LRMS: m/z 386(MH$^+$) |

PREPARATION 66

N-{1-[3-Amino-3-(3,4-dichlorophenyl)propyl]-4-piperidinyl}-2-(4-methoxyphenyl)acetamide

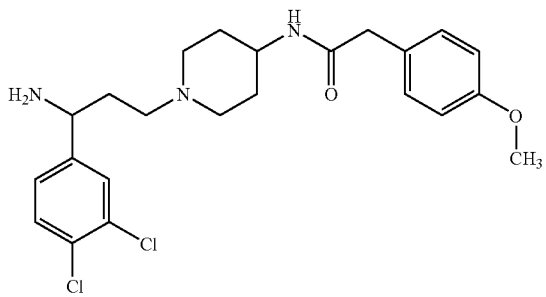

The title compound of preparation 59 (203 mg, 0.302 mmol) was dissolved in piperidine/dimethylformamide (0.65 ml, 15% solution) and dichloromethane (3 ml) and reaction stirred at room temperature for 18 hours. The solvent was the evaporated under reduced pressure and the residue partitioned between water and dichloromethane. The aqueous layer was further extracted with dichloromethane (×2), the combined organic layers were dried (MgSO$_4$), filtered and the solvent removed under reduced pressure. The crude product was purified by column chromatography on silica gel using dichloromethane:methanol:0.88 ammonia, (98:2:0.25) as eluant to afford the title compound as a clear oil, 80 mg.

$^1$H NMR (300 MHz, CDCl$_3$): δ [ppm] 1.20–1.41 (2H, m), 1.60–1.94 (4H, m), 2.04 (2H,) m), 2.31 (2H, m), 2.72 (2H, t), 3.49 (2H, s), 3.68–3.89 (4H, m), 3.96 (1H, t), 5.19 (1H, d), 6.90 (2H, d), 7.14 (3H, d), 7.36 (1H, d), 7.44 (1H, s).

LRMS: m/z 450 (MH$^+$).

PREPARATION 67

2-(4-Fluorophenyl)-N-{1-[(3S)-3-(3-fluorophenyl)-3-(methylamino)propyl]-4-piperidinyl}acetamide

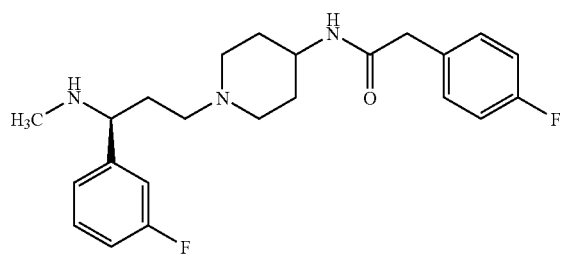

The title compound of preparation 60 (260 mg, 0.53 mmol), ammonium formate (260 mg, 4.12 mmol) and 20% palladium hydroxide on carbon (50 mg) were refluxed together in 10 ml of ethanol until gas evolution ceased. After cooling to room temperature, the fixture was filtered though a pad of Arbocel® to removed the catalyst and the filtrate evaporated under reduced pressure to afford the title compound as a gum, 200 mg.

$^1$H NMR (400 MHz, CDCl$_3$): δ [ppm] 1.29–1.45 (2H, m), 1.68–1.81 (1H, m), 1.81–1.92 (2H, m), 1.92–2.03 (2H, m), 2.03–2.19 (2H, m), 2.23–2.31 (1H, m), 2.27 (3H, s), 2.31–2.40 (1H, m), 2.66–2.76 (1H, m), 2.82–2.90 (1H, m), 3.48 (2H, s), 3.56–3.63 (1H, m), 3.68–3.84 (1H, m), 5.29–5.40 (1H, m), 6.89–7.00 (1H, m), 7.00–7.06 (3H, m), 7.06–7.11 (1H, m), 7.18–7.32 (3H, m).

LRMS: m/z 402.1 (MH+).

PREPARATION 68

Methyl (3S)-3-[(tert-butoxycarbonyl)amino]-3-phenylpropanoate

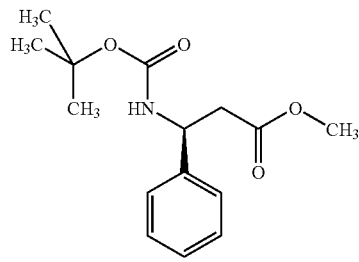

The title compound from preparation 24 (5.38 g, 30 mmol) and di-tert-butyl dicarbonate (8.72 g, 40 mmol) in tetrahydrofuran (50 ml) and 2N sodium hydroxide solution (25 ml) were stirred at room temperature for 2 hours. The reaction mixture was diluted with ethyl acetate, the layers separated and the aqueous phase extracted with ethyl acetate (2×). The combined organic solutions were washed with water, brine, dried (MgSO$_4$), filtered and evaporated under reduced pressure to afford the title compound as a white solid, 8.39 g.

$^1$H NMR (400 MHz, CDCl$_3$): δ [ppm] 1.41 (9H, s), 2.84 (2H, m), 3.61 (3H, s), 5.10 (1H, bs), 5.41 (1H, bs), 7.22–7.36 (5H, m).

LRMS: m/z 279.7 (MH$^+$).

PREPARATION 69 tert-Butyl (1S)-3-oxo-1-phenylpropylcarbamate

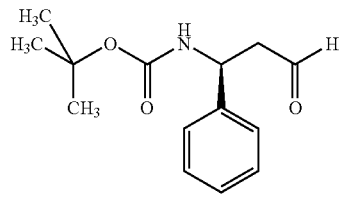

Diisobutylaluminium hydride (1M in dichloromethane, 60 ml, 60 mmol) was cooled to −78° C. and added dropwise to a solution of the title compound from preparation 68 (8.39 g, 30 mmol) in dichloromethane (150 ml) at −78° C. The reaction was stirred for 90 minutes, then methanol (pre-cooled to −78° C., 40 ml) was added. The mixture was allowed to warm to room temperature and poured into 2M hydrochloric acid (200 ml). The layers were separated and the aqueous phase extracted with dichloromethane (2×). The combined organic layers were dried (MgSO$_4$), filtered and evaporated under reduced pressure to afford the title compound as a white solid, 6.72 g.

$^1$H NMR (400 MHz, CDCl$_3$): δ [ppm] 1.42 (9H, s), 2.86–3.00 (2H, m), 5.06 (1H, bs), 5.20 (1H, bs), 7.22–7.38 (5H, m), 9.75 (1H, s).

LRMS: m/z 250.1 (MH$^+$).

PREPARATION 70

N-{1-[(3S)-3-Amino-3-phenylpropyl]-4-piperidinyl}-2-(4-fluorophenyl)acetamide

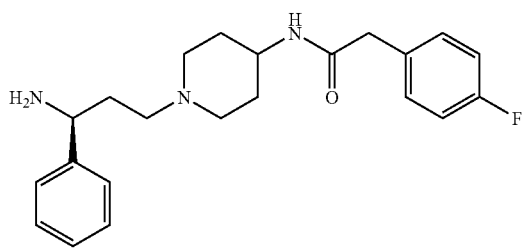

The title compound of preparation 69 (1.4 g, 5.62 mmol), the title compound of preparation 4 (1.45 g, 5.62 mmol) and sodium triacetoxyborohydride (1.9 g, 8.43 mmol) were stirred together for 18 hours in a 50 ml mixture of glacial acetic acid:dichloromethane (1:10). The mixture was evaporated under reduced pressure and basified with saturated sodium carbonate solution before extracting with dichloromethane (×3). The organics layers were combined and dried (MgSO$_4$), filtered and evaporated under reduced pressure. The residue was stirred for 2 hours in a 30 ml mixture of trifluoroacetic acid:dichloromethane (1:2). The mixture was evaported under reduced pressure and basified with saturated sodium carbonate before extracting with dichloromethane (×5). The organic layers were combined and dried (MgSO$_4$), filtered and evaporated under reduced pressure. The residue was purified by recrystallization from methyl t-butyl ether to afford the title compound as a crystalline solid, 1.55 g.

$^1$H NMR (400 MHz, CDCl$_3$): δ [ppm] 1.23–1.40 (2H, m), 1.74–2.10 (8H, m), 2.23–2.40 (2H, m), 2.66–2.80 (2H, m), 3.50 (2H, s), 3.68–3.80 (1H, m), 3.90–3.97 (1H, m), 5.20–5.27 (1H, m), 6.97–7.06 (2H, m), 7.16–7.37 (7H, m).

PREPARATION 71

N-[3-(4-Amino-1-piperidinyl)-1-phenylpropyl] cyclobutanecarboxamide

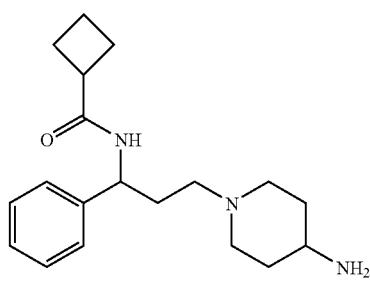

Sodium triacetoxyborohydride (3.02 g, 14.2 mmol) and acetic acid (0.54 ml, 9.52 mmol) was added to a solution of 2,2,2-trifluoro-N-(4-piperidinyl)acetamide (1.86 g, 9.52 mmol) [J. Med. Chem., (1991), 34(2), 656–663] and the title compound of preparation 21 (2.20 g, 9.52 mmol) in 1,1,1-trichloroethane (30 ml). The reaction mixture was stirred at room temperature for 18 hours, after which time 2N sodium hydroxide (30 ml) and ethanol (30 ml) were added to the mixture and stirring continued for 1 hour. The solvent was then removed under reduced pressure and the residue partitioned between water and dichloromethane, the aqueous layer was separated and extracted with dichloromethane (×2). The combined organic layers were dried (MgSO$_4$), filtered and the solvent removed under reduced pressure. The crude product was purified by column chromatography on silica gel using dichloromethane:methanol:0.88 ammonia (90:10:1) as the eluant to afford the title compound as a yellow oil, 1.50 g.

$^1$H-NMR (400 MHz, CDCl$_3$): δ [ppm] 1.30–2.40 (18H, m), 2.72 (1H, m), 2.80 (1H, d), 2.92–3.08 (2H, m), 5.13 (1H, m), 7.20–7.33 (5H, m), 7.80 (1H, d).

LRMS: m/z 316 (MH$^+$).

PREPARATION 72

N-(1S)-[3-(4-Amino-1-piperidinyl)-1-phenylpropyl]cyclobutanecarboxamide

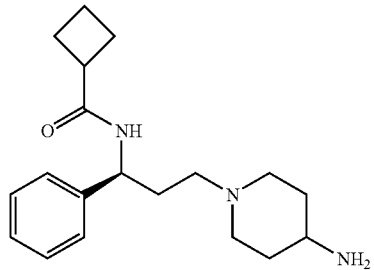

Obtained from the title compound of preparation 26 and 2,2,2-trifluoro-N-(4-piperidinyl)acetamide using a similar procedure to that described for the racemate in preparation 71.

EXAMPLE 1

N-(1-Phenyl-3-{4-[(2-phenylacetyl)amino]-1-piperidinyl}propyl)cyclobutanecarboxamide

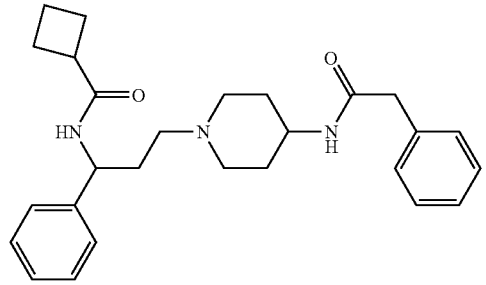

Benzoyl chloride (70 μl, 0.53 mmol) was added to a solution of the title compound of preparation 71 (140 mg, 0.44 mmol) and triethylamine (74 μl, 0.53 mmol) in dichloromethane (10 ml). The reaction mixture was stirred for 1 hour and purified directly by column chromatography on silica gel using dichloromethane:methanol:0.88 ammonia (95:5:0.5) as eluant to afford the title compound as a white foam, 49 mg.

Found C, 73.71; H, 8.20; N, 9.54%.

C$_{27}$H$_{35}$N$_3$O$_2$; requires C 74.79; H, 8.14; N, 9.69%.

$^1$H NMR (300 MHz, CDCl$_3$): δ [ppm] 1.21–1.46 (2H, m), 1.73–2.40 (15H, m), 2.69 (1H, d), 2.78 (1H, d), 2.98 (1H, m), 3.56 (2H, s), 3.80 (1H, m), 5.08 (1H, m), 5.25 (1H, d), 7.18–7.42 (10H, m).

LRMS: m/z 434 (MH$^+$).

EXAMPLE 2

N-[3-(4-{[2-(4-Methoxyphenyl)acetyl]amino}-1-piperidinyl)-1-(4-methoxyphenylpropyl]cyclobutanecarboxamide

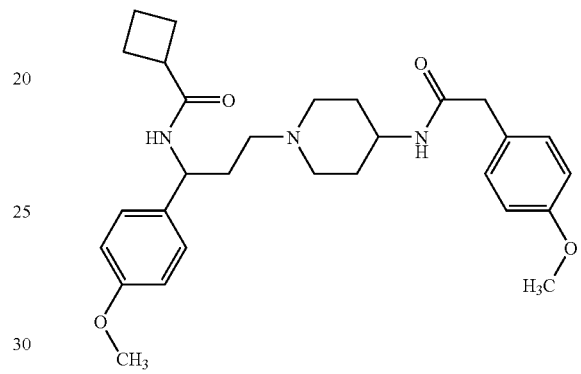

Cyclobutanecarbonyl chloride (42 μl, 0.37 mmol) was added to a solution of the title compound of preparation 62 (150 mg, 0.36 mmol) and triethylamine (54 μl, 0.39 mmol) in dichloromethane (6 ml) under ice cooling. The reaction mixture was allowed to warm to room temperature, stirred for 1 hour, then diluted with dichloromethane and water. The layers were separated and the aqueous layer extracted several times with dichloromethane. The combined organic layers were dried (MgSO$_4$), filtered and evaporated under reduced pressure. Purification by column chromatography on silica gel using dichloromethane:methanol:0.88 ammonia (95:5:0.5) afforded the title compound as a white solid which was recrystallised from ethyl acetate/isopropyl alcohol, 49 mg.

Found: C, 70.47; H, 8.00; N, 8.55%.

C$_{29}$H$_{39}$N$_3$O$_4$; requires C, 70.56; H, 7.96; N, 8.31%.

$^1$H NMR (400 MHz, CDCl$_3$): δ [ppm] 1.24–1.40 (2H, m); 1.74–2.00 (6H, m), 2.00–2.16 (4H, m), 2.16–2.35 (4H, m), 2.63–2.71 (1H, m), 2.71–2.80 (1H, m), 2.94 (1H, m), 3.50 (2H, s), 3.77 (3H, s), 3.80 (3H, s), 3.73–3.84 (1H, m), 5.02 (1H, m), 5.20 (1H, d), 6.84 (2H, d), 6.90 (2H, d), 7.03 (1H, d), 7.10–7.19 (4H, m).

LRMS: m/z 494 (MH$^+$).

Melting point [° C.]: 165–166 (ethyl acetate/isopropyl alcohol).

EXAMPLE 3–6

The compounds of the following tabulated examples with the general formula:

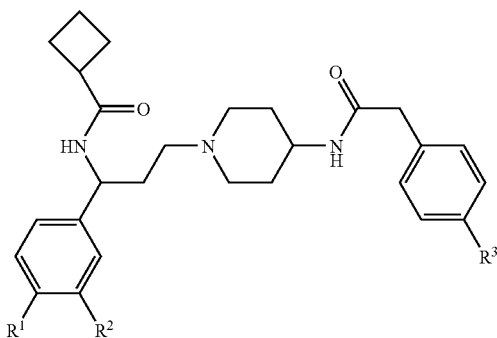

were prepared using a similar method to Example 2 from cyclobutanecarbonyl chloride and the corresponding amines.

| EX. NO. | R¹ | R² | R³ | YIELD (%) | CHARACTERIZATION DATA |
|---|---|---|---|---|---|
| 3 | Cl | Cl | OCH$_3$ | 85 | Found: C, 60.71; H, 6.52; N, 7.45% $C_{28}H_{35}Cl_2N_3O_3$; 1.1H$_2$O requires C, 60.71; H, 6.51; N 7.45% $^1$H NMR(300MHz, CDCl$_3$): δ[ppm] 1.20–1.44(1H, m); 1.64–2.40(11H, m); 2.60–2.86(2H, m); 2.98(1H, m); 3.51(2H, s); 3.70–3.80(1H, m); 3.83(3H, s); 4.99(1H, m); 5.23(1H, d); 6.90(2H, d); 7.05(1H, m); 7.18(2H, d); 7.26(1H, d); 7.44(1H, m). LRMS: m/z 532(MH$^+$) Melting point [° C.]: 80–81 |
| 4 | H | Cl | H | 62 | Found: C, 68.57; H, 7.37; N, 8.80% $C_{27}H_{34}N_3O_2Cl$; 0.3H$_2$O requires C, 68.50; H, 7.37; N 8.88% $^1$H NMR(300MHz, CD$_3$OD): δ[ppm] 1.43–1.58(2H, m), 1.79–2.40(15H, m), 2.81–2.90(2H, br m), 3.13(1H, m), 3.46(2H, s), 3.60–3.68(1H, broad m), 4.87(1H, t), 7.18–7.35(9H, m) |
| 5 | H | F | H | 48 | Found: C, 68.94; H, 7.38; N, 9.03% $C_{27}H_{34}FN_3O_2$; H$_2$O requires C, 69.06; H, 7.73; N 8.95% $^1$H NMR(400MHz, CDCl$_3$): δ[ppm] 1.21–1.45(2H, m), 1.68–1.80(1H, m), 1.80–2.37(14H, m), 2.55–2.71(1H, m), 2.71–2.87(1H, m), 2.97(1H, m), 3.57(2H, s), 3.80(1H, m), 5.03–5.12(1H, m), 5.18–5.27(1H, m), 6.83–6.94(2H, m), 6.99(1H, d), 7.19–7.27(2H, m), 7.27–7.42(3H, m), 7.58(1H, d) LRMS: m/z 452.1(MH$^+$) Melting point [° C.]: 160 |
| 6 | Cl | H | H | 61 | Found: C, 68.05; H, 7.41; N, 8.81% $C_{27}H_{33}FN_4O$; 0.5H$_2$O requires C, 67.98; H, 7.40; N 8.81% $^1$H NMR(400MHz, CDCl$_3$): δ[ppm] 1.32(2H, m), 1.66–1.80(1H, m), 1.80–2.35(13H, m), 2.57–2.70(1H, br d), 2.70–2.81(1H, br d), 2.97(1H, d), 3.58(2H, s), 3.81(1H, m), 5.04(1H, m), 5.20(1H, d), 7.15(2H, d), 7.24–7.40(6H, m), 7.43–7.56(1H, d) LRMS: m/z 468.0(MH$^+$) Melting point [° C.]: 70–71 |

EXAMPLE 7

N-[3-(4-{[2-(4-Methoxyphenyl)acetyl]amino}-1-piperidinyl)-1-phenylpropyl]cyclobutanecarboxamide

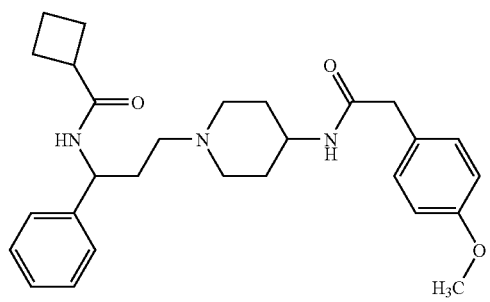

1-(3-Dimethylaminopropyl)-3-ethylcarbodiimide hydrochloride (109 mg, 0.57 mmol) was added to a solution of the title compound of preparation 71 (150 mg, 0.47 mmol), 2-(4-methoxyphenyl)acetic acid (7.9 mg, 0.47 mmol) and 1-hydroxybenzotriazole hydrate (80 mg, 0.52 mmol) in dichloromethane (10 ml). The reaction mixture was stirred for 56 hours after which time the mixture was washed with water and the organic layer separated and dried (MgSO$_4$). The crude product was purified by column chromatography on silica gel using dichloromethane:methanol:0.88 ammonia (95:5:0.5) as eluant to afford the title compound as a white foam, 60 mg.

Found: C, 71.72; H, 8.07; N, 9.02%.

$C_{28}H_{37}N_3O_3 \times 0.3H_2O$; requires C, 71.70; H, 8.07; N, 8.96%.

$^1$H-NMR (300 MHz, CDCl$_3$): δ [ppm] 1.20–1.42 (2H, m), 1.72–2.36 (15H, m), 2.67 (1H, d), 2.78 (1H, d), 2.98 (1H, m), 3.49 (2H, s), 3.72–3.85 (4H, m), 5.08 (1H, m), 5.25 (1H, d), 6.89 (2H, d), 7.12–7.34 (7H, m).

LRMS: m/z 464 (MH$^+$).

EXAMPLE 8–9

The compounds of the following tabulated examples with the general formula:

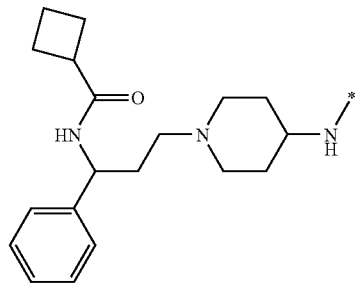

were prepared used a similar method to Example 7 from the title compound of preparation 71 and the corresponding acids.

| EX. NO. | R | YIELD (%) | CHARACTERIZATION DATA |
|---|---|---|---|
| 8 | 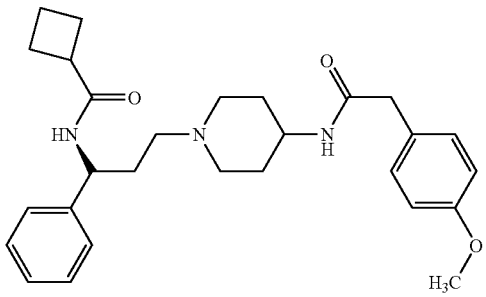 | 37 | Found: C, 73.98; H, 8.42; N, 9.13% $C_{28}H_{37}N_3O_2$; 0.4$H_2O$; requires C, 73.94; H, 8.38; N 9.24% $^1$H NMR (300 MHz, CDCl$_3$): mixture of diastereomers δ [ppm] 1.17–1.42(2H, m), 1.48 and 1.50(3H, 2xs), 1.72–2.38(15H, m), 2.57–2.82(2H, br m), 2.96(1H, m), 3.54(1H, m), 3.68–3.82(1H, br m), 5.01–5.18(2H, m), 7.13–7.40(10H, m) LRMS: m/z 448.5(MH$^+$) |
| 9 | | 53 | Found: C, 69.90; H, 7.77; N, 8.65% $C_{28}H_{37}N_3O_2$; 0.5CH$_2$Cl$_2$; requires C, 69.85; H, 7.82; N 8.57% $^1$H NMR(300 MHz, CDCl$_3$): mixture of diastereomers δ [ppm] 1.18–1.41(2H, m), 1.45 and 1.50(3H, 2xs), 1.72–2.40(15H, m), 2.58–2.81(2H, br m), 2.97(1H, m), 3.50(1H, m), 3.67–3.83(1H, br m), 5.00–5.20(2H, m), 7.12–7.39(10H, m) LRMS: m/z 448.9(MH$^+$) |

EXAMPLE 10

N-[(1S)-3-(4-{[2-(4-Methoxyphenyl)acetyl]amino}-1-piperidinyl)-1-phenylpropyl] cyclobutanecarboxamide

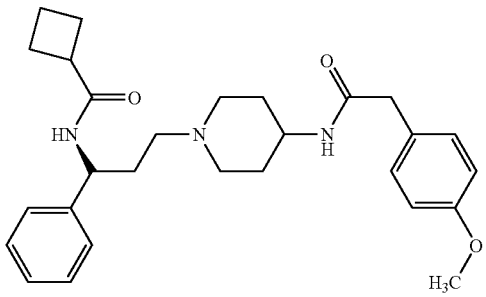

The title compound was prepared using a similar method to preparation 71 from the title compounds of preparations 26 and 6. The crude product was purified by column chromatography on silica gel using dichloromethane:methanol:0.88 ammonia (98:2:0.25) as the eluant, and the product was then recrystallised from ethyl acetate to afford the title compound as a solid, 90 mg.

Found: C, 72.39; H, 8.04; N, 9.01%.

$C_{28}H_{37}N_3O_3$; requires C, 72.54; H, 8.04; N, 9.06%.

$^1$H-NMR (300 MHz, CDCl$_3$); δ [ppm] 1.21–1.43 (2H, m), 1.75–2.37 (15H, m), 2.65 (1H, d), 2.78 (1H, d), 2.97 (1H, m), 3.49 (2H, s), 3.70–3.85 (4H, m), 5.09 (1H, m), 5.21 (1H, d), 6.88 (2H, d), 7.13–7.35 (7H, m).

LRMS: m/z 464 (MH$^+$).

EXAMPLE 11–12

The compounds of the following tabulated examples with the general formula:

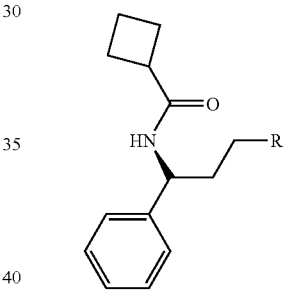

were prepared using a similar method to example 10 from the title compound of preparation 26 and the corresponding amines.

| EX. NO. | R | YIELD (%) | CHARACTERIZATION DATA |
|---|---|---|---|
| 11 | | 37 | Found: C, 72.00; H, 7.87; N, 9.30% $C_{27}H_{35}N_3O_3$; requires C, 72.13; H, 7.85; N 9.35% $^1$H NMR(300 MHz, CDCl$_3$): δ [ppm] 1.80–2.38(12H, m), 2.37(2H, m), 2.58(1H, t), 2.78(1H, m), 2.92(1H, m), 3.51(2H, s), 3.78(3H, s), 4.38(1H, m), 5.16(1H, m), 5.95(1H, br d), 6.57(1H, br d), 6.85(2H, d), 7.20(7H, m) LRMS: m/z 450.6(MH$^+$) Melting point [° C.]: 175–176 (ether) [α]$_D$ −33.5° (c = 0.27, MeOH) |

-continued

| EX. NO. | R | YIELD (%) | CHARACTERIZATION DATA |
|---|---|---|---|
| 12 | 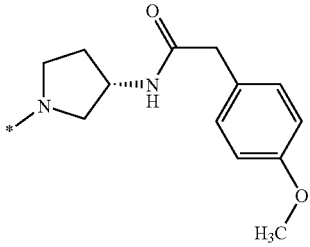 | 8 | Found: C, 71.97; H, 7.87; N, 9.33%<br>$C_{27}H_{35}N_3O_3$; requires C, 72.13; H, 7.85; N 9.35%<br>$^1$H NMR(300 MHz, CDCl$_3$): δ [ppm]<br>1.40–1.55(1H, m), 1.80–2.01(4H, m), 2.03–2.55(9H, m), 2.60–2.75(2H, m),<br>2.92(1H, m), 3.43(2H, s), 3.80(3H, s), 4.40(1H, m), 5.05(1H, m),<br>5.80(1H, br d), 6.60(1H, br d), 6.85(2H, d), 7.10–7.35(7H, m)<br>LRMS: m/z 449.3(MH$^+$)<br>Melting point [° C.]: 145–146 (ether)<br>[α]$_D$ –62.5° (c = 0.17, MeOH) |

EXAMPLE 13–14

The compounds of the following tabulated examples with the general formula:

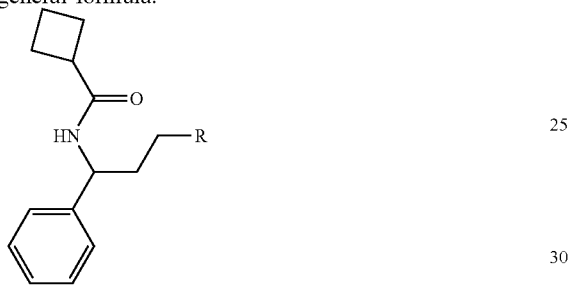

were prepared using a similar method to example 10 from the title compound of preparation 21 and the corresponding amine.

| EX. NO. | R | YIELD (%) | CHARACTERIZATION DATA |
|---|---|---|---|
| 13 | 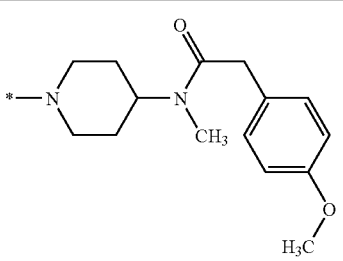 | 55 | Found: C, 70.30; H, 8.56; N, 8.61%<br>$C_{29}H_{39}N_3O_3$; H$_2$O requires C, 70.27; H, 8.34; N, 8.48%<br>$^1$H NMR(400 MHz, CDCl$_3$): δ [ppm]<br>1.25–1.39(1H, m), 1.58–2.20(13H, m), 2.20–2.38(3H, m), 2.80–2.95(3H, m),<br>2.95–3.08(2H, m), 3.58–3.72(2H, m), 3.78(3H, s), 4.45–4.58(1H, m),<br>5.05–5.15(1H, m), 6.82–6.90(2H, m), 7.12–7.35(7H, m)<br>LRMS: m/z 478.2 (MH$^+$) |
| 14 | 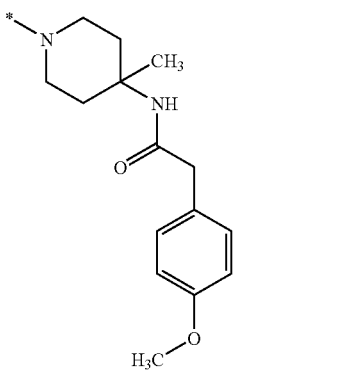 | 26 | Found: C, 71.36; H, 8.19; N, 8.51%<br>$C_{29}H_{39}N_3O_3$; 0.6H$_2$O; requires C, 71.31; H, 8.30; N, 8.60%<br>$^1$H NMR(400 MHz, CDCl$_3$): δ [ppm] 1.49–1.62(8H, m), 1.72–2.02(8H, m),<br>2.10–2.20(2H, m), 2.20–2.35(2H, m), 2.40–2.50(1H, m), 2.52–2.62(1H, m),<br>3.42(2H, s), 3.79(3H, s), 5.02–5.12(1H, m), 6.82–6.91(2H, m),<br>7.15–7.37(6H, m), 7.41–7.49(1H, m)<br>LRMS: m/z 478.2 (MH$^+$) |

EXAMPLE 15

N-[(1R)-3-(4-{[2-(4-Methoxyphenyl)acetyl]amino}-1-piperidinyl)-1-phenylpropyl] cyclobutanecarboxamide

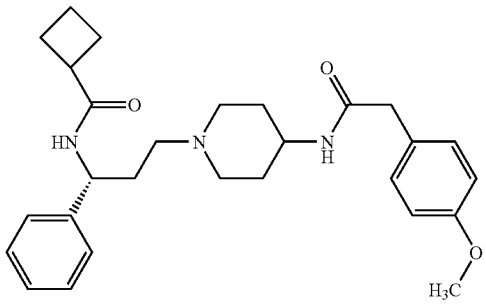

The title compound was prepared using a similar method to example 2 from the title compound of preparation 61 and cyclobutanecarbonyl chloride, 56%.

Found: C, 69.80; H, 7.80; N, 8.72%.

$C_{28}H_{37}N_3O_3$; $0.1H_2O$ requires C, 69.83; H, 8.16; N, 8.72%.

$^1$H NMR (400 MHz, CDCl$_3$): δ [ppm] 1.23–1.40 (2H, m), 1.74–2.32 (15H, m), 2.60–2.70 (1H, m), 2.70–2.80 (1H, m), 2.97 (1H, m), 3.48 (2H, s), 3.71–3.84 (1H, m), 3.81 (3H, s), 5.08 (1H, m), 5.21 (1H, d), 6.89 (2H, d), 7.13–7.23 (5H, m), 7.23–7.32 (2H, m).

LRMS: m/z 464 (MH$^+$).

[α]$_D$ +37.8° (c=0.18, MeOH).

EXAMPLE 16

N-((1S)-1-(3-Fluorophenyl)-3-{4-[(2-phenylacetyl)amino]-1-piperidinyl}propyl)-1-pyrrolidinecarboxamide

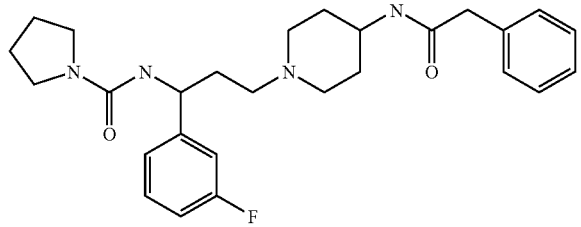

The title compound of preparaiton 56 (140 mg, 0.30 mmol) was stirred for 30 minutes in a 5 ml mixture of trifluoroacetic acid:dichloromethane. The solvents were removed under reduced pressure and basified with saturated sodium carbonate solution before extracting with dichloromethane (×3). The organic layers were combined and dried (MgSO$_4$), filtered and evaporated under reduced pressure. The residue (100 mg, 0.27 mmol) in 1 ml of dichloromethane was added to a mixture of 1,1'-carbonyldiimidazole (44 mg, 2.71 mmol) and imidazole (18 mg, 2.71 mmol) in 1 ml of dichloromethane at 0° C. The mixture was stirred for 15 minutes and then warmed slowly to room temperature over 1 hour. A solution of pyrrolidine (26 mg, 2.71 mmol) in 1 ml of dichloromethane was added and the mixture stirred for 18 hours. The mixture was diluted with dichloromethane and washed with water. The organic layer was dried (MgSO$_4$), filtered and evaporated under reduced pressure. the residue was purified by column chromatography on silica gel using an eluent of dichloromethane:methanol:0.88 ammonia (95:5:0.5) to afford the title compound as a colourless glass, 39 mg.

Found: C, 68.46; H, 7.68; N, 11.85%.

$C_{27}H_{35}FN_4O_2$; $0.5 H_2O$ requires C, 68.19; H, 7.63; N, 11.78%.

$^1$H NMR (400 MHz, CDCl$_3$): δ [ppm] 1.20–1.37 (2H, m), 1.71–1.81 (1H, m), 1.81–1.94 (6H, m), 1.94–2.11 (3H, m), 2.19–2.34 (2H, m), 2.60–2.71 (1H, m), 2.71–2.80 (1H, m), 3.26–3.37 (4H, m), 3.55 (2H, s), 3.73–3.82 (1H, m), 4.94–5.00 (1H, m), 5.13–5.23 (1H, m), 6.13–6.20 (1H, m), 6.84–6.90 (1H, m), 6.90–6.97 (1H, m), 7.00–7.03 (1H, m), 7.20–7.26 (3H, m), 7.26–7.32 (1H, m), 7.32–7.40 (2H, m).

LRMS: m/z 467.1 (MH$^+$).

EXAMPLE 17

N-((1S)-1-(3-Fluorophenyl)-3-{4-[(2-phenylacetyl)amino]-1-piperidinyl}propyl)-1-hydroxycyclopentanecarboxamide

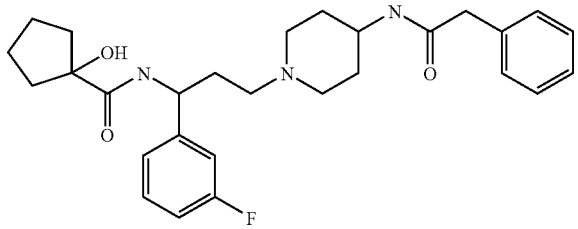

The title compound of preparation 56 (140 mg, 0.30 mmol) was stirred for 30 minutes in a mixture of trifluoroacetic acid:dichloromethane (5 ml, 1:1). The solvents were removed under reduced pressure and basified with saturated sodium carbonate solution before extracting with dichloromethane (×3). The organic layers were combined and dried (MgSO$_4$), filtered and evaporated under reduced pressure. The residue (100 mg, 2.71 mmol), 1-hydroxycyclopentanecarboxylic acid (39 mg, 2.98 mmol), 1-hydroxybenzotriazole monohydrate (44 mg, 3.25 mmol), 1-(3-dimethylaminopropyl)-3-ethyl-carbodiimide hydrochloride (67 mg, 3.52 mmol) and triethylamine (0.05 ml, 3.52 mmol) were stirred together for 18 hours in dichloromethane (6 ml). The solvent was removed under reduced pressure and the residue dissolved in ethyl acetate, then washed with water (×2). The organic layer was dried (MgSO$_4$), filtered and evaporated under reduced pressure. the residue was purified by column chromatography on silica gel using an eluent of dichlromethane:methanol:0.88 ammonia (95:5:0.5) to afford the title compound as a white foam, 93 mg.

Found: C, 68.69; H, 7.60; N, 8.55%.

$C_{28}H_{37}FN_3O_3$; $0.4 H_2O$ requires C, 68.66; H, 7.78; N, 8.58%.

$^1$H NMR (400 MHz, CDCl$_3$): δ [ppm] 1.35–1.48 (2H, m), 1.65–1.94 (7H, m), 1.94–2.24 (7H, m), 2.24–2.35 (2H, m), 2.60–2.69 (1H, m), 2.76–2.85 (1H, m), 3.56 (2H, s), 3.68–3.81 (1H, m), 5.05–5.11 (1H, m), 5.20–5.27 (1H, m), 6.87–6.94 (2H, m), 6.97–7.01 (1H, m), 7.23–7.40 (7H, m), 8.53–8.61 (1H, m).

LRMS: m/z 482.1 (MH$^+$).

EXAMPLE 18

N-((1S)-1-(3-Fluorophenyl)-3-{4-[(2-phenylacetyl)amino]-1-piperidinyl}propyl)tetrahydro-2H-pyran-4-carboxamide

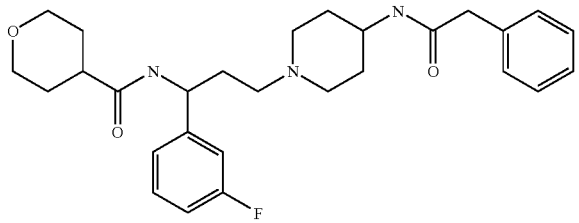

The title compound was prepared using a similar procedure to that described in example 17 from tetrahydro-2H-pyran-4-carboxylic acid and purifying by recrystallisation from ethyl acetate in a 51% yield, 66 mg.

$^1$H NMR (400 MHz, CDCl$_3$): δ [ppm] 1.21–1.40 (3H, m), 1.66–1.84 (5H, m), 1.84–2.16 (5H, m), 2.16–2.24 (1H, m), 2.24–2.39 (2H, m), 2.63–2.74 (1H, m), 2.77–2.87 (1H, m), 3.27–3.39 (2H, m), 3.55 (2H, s), 3.74–3.84 (1H, m), 3.90–4.00 (2H, m), 5.02–5.08 (1H, m), 5.20–5.27 (1H, m), 6.82–6.94 (2H, m), 6.94–6.99 (1H, m), 7.21–7.39 (5H, m), 7.97–8.05 (1H, m).

LRMS: m/z 482.3 (MH$^+$).

EXAMPLE 19

N-((1R,2S)-2-Methoxy-1-phenyl-3-{4-[(2-phenylacetyl)amino]-1-piperidinyl}propyl)cyclobutanecarboxamide

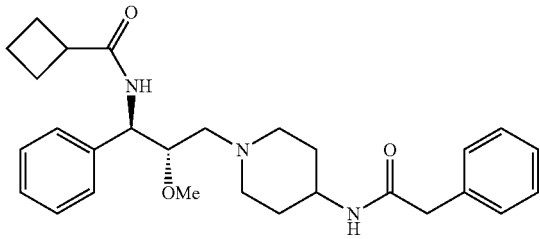

Diisobutylaluminium hydride (3.47 ml of a 1.0 M solution in dichloromethane, 3.47 mmol) was added dropwise to a solution of the title compound of preparation 51 (460 mg, 1.58 mmol) in dichloromethane (20 ml) at −78° C. The reaction mixture was stirred at this temperature for 1 hour, then methanol (2 ml) pre-cooled to −78° C. was added. The mixture was warmed to room temperature and washed with 2M hydrochloric acid, water and brine, dried (MgSO$_4$), filtered and the solvent evaporated under reduced pressure to afford the aldehyde as a clear oil, 400 mg. This oil (400 mg, 1.53 mmol), the title compound of preparation 2 (334 mg, 1.53 mmol) and sodium triacetoxyborohydride (483 mg, 2.28 mmol) were stirred together for 3 hours at room temperature in dichloromethane:acetic acid (30 ml, 10%). The solvents were evaporated under reduced pressure and the residue dissolved in ethyl acetate and washed with saturated aqueous sodium carbonate solution then water. The organic layer was dried (MgSO$_4$), filtered and evaporated under reduced pressure. The residue was purified by flash column chromatography on silica gel using dichloromethane:methanol:0.88 ammonia (95:5:0.5) as eluant to afford the title compound as a white solid, 117 mg.

$^1$H NMR (400 MHz, CDCl$_3$): δ [ppm] 1.31 (3H, m), 1.81 (4H, m), 2.05–2.18 (7H, m), 2.61 (1H, d), 2.76 (1H, d), 3.05 (1H, m), 3.25 (3H, s), 3.48 (1H, m), 3.58 (2H, m), 3.79 (1H, m), 5.23 (2H, m), 6.78 (1H, d), 7.18–7.38 (10H, m).

LRMS: m/z 464.1 (MH$^+$).

[α]$_D$: −28.1 (c=5.10, methanol).

EXAMPLE 20

N-[(1S)-3-(4-{[(2R)-2-Methoxy-2-phenylethanoyl]amino}-1-piperidinyl)-1-phenylpropyl]cyclobutanecarboxamide

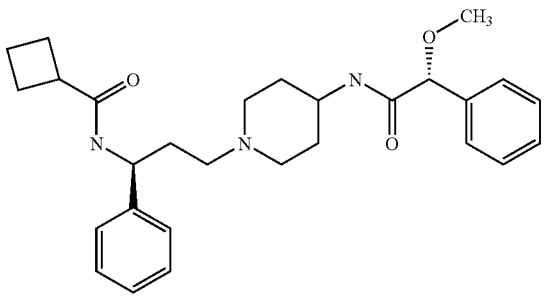

A solution of the title compound of preparation 72 (100 mg, 0.32 mmol) in dichloromethane (2.5 ml) was added to a solution of 1-(3-dimethylaminopropyl)-3-ethylcarbodiimide hydrochloride (60 mg, 0.32 mmol), (R)-α-methoxyphenyl acetic acid (53 mg, 0.32 mmol), 1-hydroxybenzotriazole hydrate (50 mg, 0.33 mmol), and diisopropylethylamine (55 µl, 0.32 mmol) in dichloromethane (2.5 ml). The reaction mixture was stirred for 30 hours, then diluted with dichloromethane and washed with 10% sodium carbonate. The layers were separated and the aqueous layer was extracted with dichloromethane (2×25 ml). The organic layers were combined, washed with brine, dried (MgSO$_4$), filtered and the solvent was evaporated. The crude product was purified by column chromatography on silica gel using dichloromethane:methanol:0.88 ammonia (95:5:0.5) as the eluant to yield the title product, 60 mg.

Found: C, 70.25; H, 8.18; N, 8.49%.

$C_{28}H_{37}N_3O_3$; 0.9H$_2$O requires C, 70.09; H, 8.15; N, 8.76%.

$^1$H NMR (400 MHz, CDCl$_3$): δ [ppm] 1.46 (2H, m), 1.76–2.41 (15H, m), 2.78 (1H, bm), 2.84 (1H, bm), 3.02 (1H, m), 3.36 (3H, s), 3.80 (1H, bm), 4.59 (1H, s), 5.12 (1H, m), 6.64 (1H, d), 7.16–7.42 (10H, m).

LRMS: m/z 464 (MH$^+$).

EXAMPLE 21

N-[(1S)-1-Phenyl-3-(4-{[2-(2-pyridinyl)acetyl]amino}-1-piperidinyl)propyl]cyclobutanecarboxamide

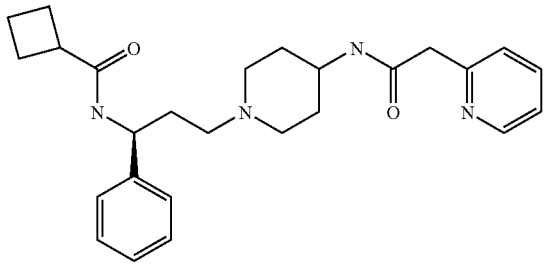

The title compound was prepared using a similar method to that described for Example 20 from the title compound of preparation 72 and 2-pyridyl acetic acid hydrochloride, 35%.

Found: C, 68.08; H, 8.05; N, 12.20%.

$C_{26}H_{34}N_4O_2$; 1.3$H_2O$ requires C, 68.08; H, 8.06; N, 12.21%.

$^1$H NMR (400 MHz, CDCl$_3$): δ [ppm] 1.46–2.41 (18H, m), 2.67 (1H, bm), 2.81 (1H, bm), 3.03 (1H, m), 3.72 (2H, s), 3.83 (1H, bm), 5.10 (1H, m), 7.14–7.32 (5H, m), 7.40 (1H, m), 7.52 (1H, m), 7.67 (1H, t), 8.54 (1H, d).

LRMS: m/z 436 (MH$^+$).

EXAMPLE 22

1-Acetyl-N-[(1S)-3-(4-{[2-(4-fluorophenyl)acetyl]amino}-1-piperidinyl)-1-phenylpropyl]-3-azetidinecarboxamide

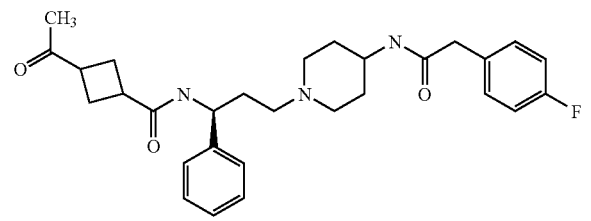

The title compound of preparation 70 (75 mg, 0.2 mmol), 1-acetyl-3-azetidinecarboxylic acid (29 mg, 0.2 mmol), 1-hydroxybenzotriazole monohydrate (30 mg, 0.22 mmol), 1-(3-dimethylaminopropyl)-3-ethyl-carbodiimide hydrochloride (47 mg, 0.24 mmol) and triethylamine (0.034 ml, 0.24 mmol) were stirred together for 4 hours in 5 ml of dichloromethane. The mixture was evaporated under reduced pressure and the residue dissolved in ethyl acetate before washing with water, saturated sodium carbonate solution then water. The organic layer was dried (MgSO$_4$), filtered and evaporated under reduced pressure. The residue was purified by column chromatography on silica gel using an eluant of dichloromethane:methanol:0.88 ammonia (95:5:0.5) to afford the title compound as a white foam, 45 mg.

$^1$H NMR (400 MHz, CDCl$_3$): δ [ppm] 1.20–1.52 (3H, m), 1.68–1.81 (1H, m), 1.18–1.85 (3H, m), 1.85–2.00 (2H, m), 2.00–2.24 (3H, m), 2.29–2.45 (1H, m), 2.71–2.80 (1H, m), 2.90–3.03 (1H, m), 3.23–3.35 (1H, m), 3.50 (2H, s), 3.74–3.87 (1H, m), 4.13–4.35 (4H, m), 5.06–5.13 & 5.13–5.21 (1H, m), 5.94–6.00 & 6.13–6.20 (1H, m), 6.98–7.03 (2H, m), 7.13–7.19 (2H, m), 7.19–7.34 (5H, m), 8.53–8.60 & 8.61–8.68 (1H, m).

LRMS: m/z 495.1 (MH$^+$).

EXAMPLE 23

N-[(1S)-3-(4-{[2-(4-Fluorophenyl)acetyl]amino}-1-piperidinyl)-1-phenylpropyl]-2,2-dimethylpropanamide

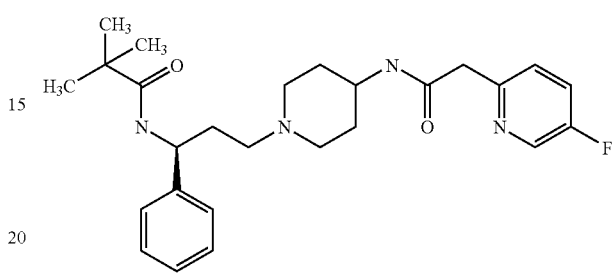

The title compound was prepared using a similar method to that described for example 1 from the title compound of preparation 70 and trimethylacetyl chloride using diisopropylethylamine as base, 43%.

Found: C, 66.74; H, 7.60; N, 8.59%.

$C_{27}H_{36}FN_3O_2$; 1.7$H_2O$ requires C, 66.97; H, 8.20; N, 8.68%.

$^1$H NMR (400 MHz, CDCl$_3$): δ [ppm] 1.19 (9H, s), 1.36 (2H, m), 1.72–1.84 (1H, m), 1.90 (2H, bm), 1.95–2.14 (3H, m), 2.14–2.24 (1H, m), 2.28–2.38 (1H, m), 2.72 (1H, m), 2.82 (1H, m), 2.97 (1H, m), 3.52 (2H, s), 3.78 (1H, m), 5.04 (1H, m), 5.11 (1H, d), 7.04 (2H, t), 7.13–7.14–7.34 (6H, m), 7.46 (1H, m).

LRMS: m/z 454 (MH$^+$).

Melting point [° C.]: 158–159.

EXAMPLE 24 UK-386739

N-[(1S)-1-(3-Fluorophenyl)-3-(4-{[2-(4-fluorophenyl)acetyl]amino}-1-piperidinyl)propyl]-N-methylcyclobutanecarboxamide

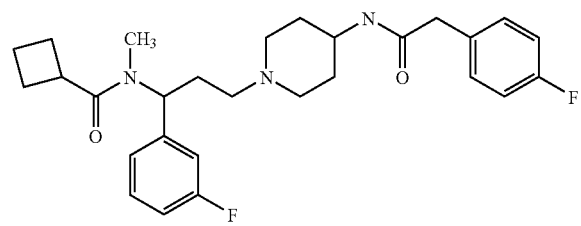

To a mixture of the title compound of preparation 67 (100 mg, 0.25 mmol) and triethylamine (0.04 ml, 0.28 mmol) in 5 ml of dichloromethane was added cyclobutylcarbonyl chloride (0.03 ml, 0.25 mmol). The mixture was evaporated under reduced pressure and the residue dissolved in ethyl acetate before washing with saturated sodium carbonate solution then water. The organic layer was dried (MgSO$_4$), filtered and evaporated under reduced pressure. The residue was purified by column chromatography on silica gel using an eluant of dichloromethane:methanol:0.88 ammonia (98:2:0.25) to afford the title compound as a gum, 20 mg.

$^1$H NMR (400 MHz, CDCl$_3$): δ [ppm] 1.26–1.40 (2H, m), 1.80–2.00 (5H, m), 2.00–2.40 (9H, m), 2.56 & 2.68 (3H, s), 2.69–2.80 (2H, m), 3.20–3.29 (1H, m), 3.50 (2H, s), 3.71–3.82 (1H, m), 5.13–5.23 (1H, m), 5.87–5.94 (1H, m), 6.84–7.00 (3H, m), 7.00–7.06 (2H, m), 7.20–7.32 (3H, m).
LRMS: m/z 484.2 (MH$^+$).
What is claimed is:
1. A compound which is selected from
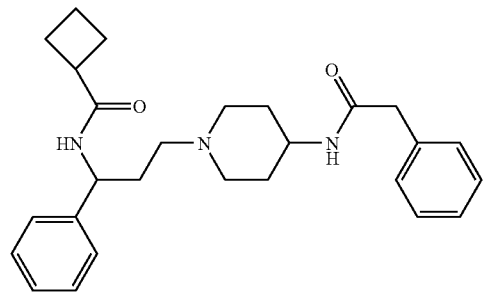
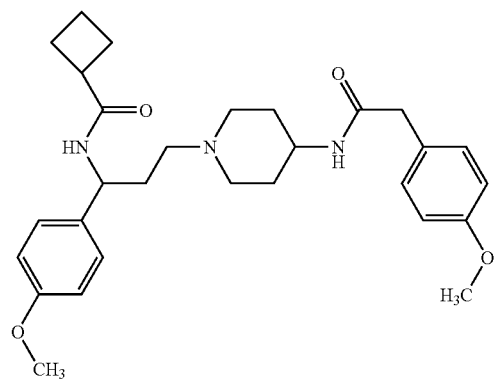
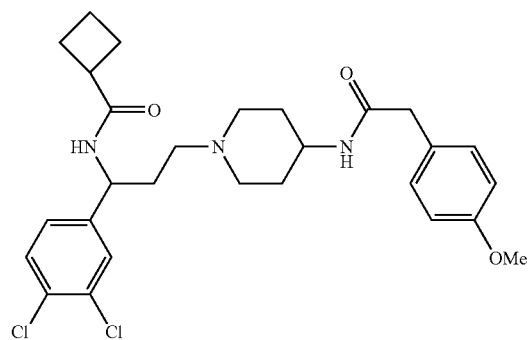
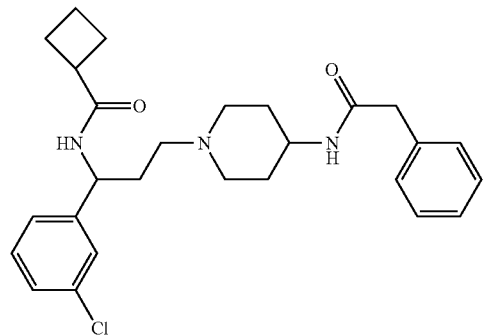
-continued
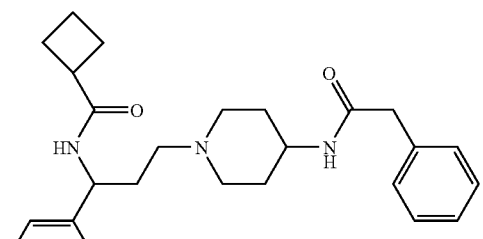
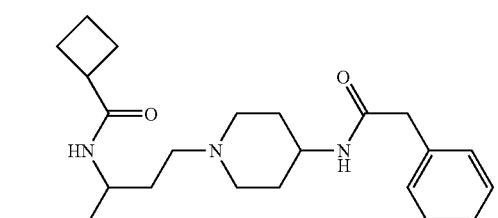
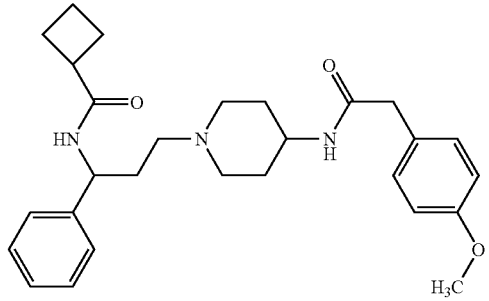
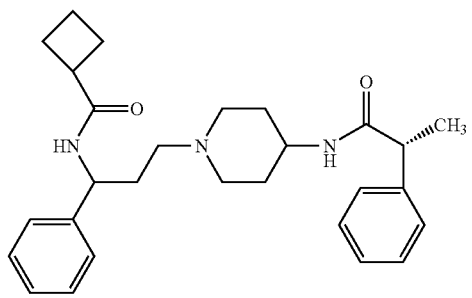
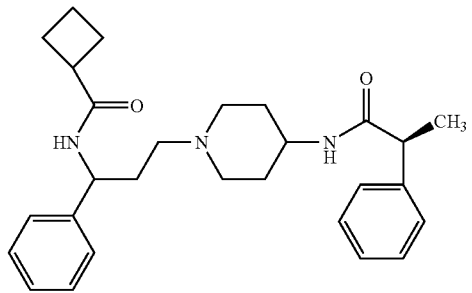

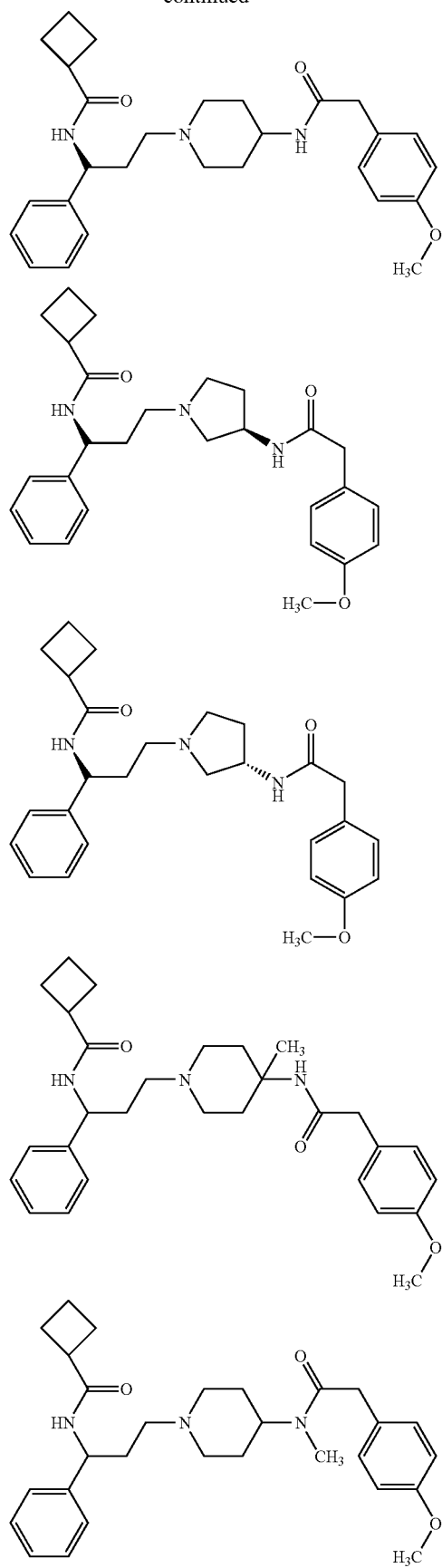
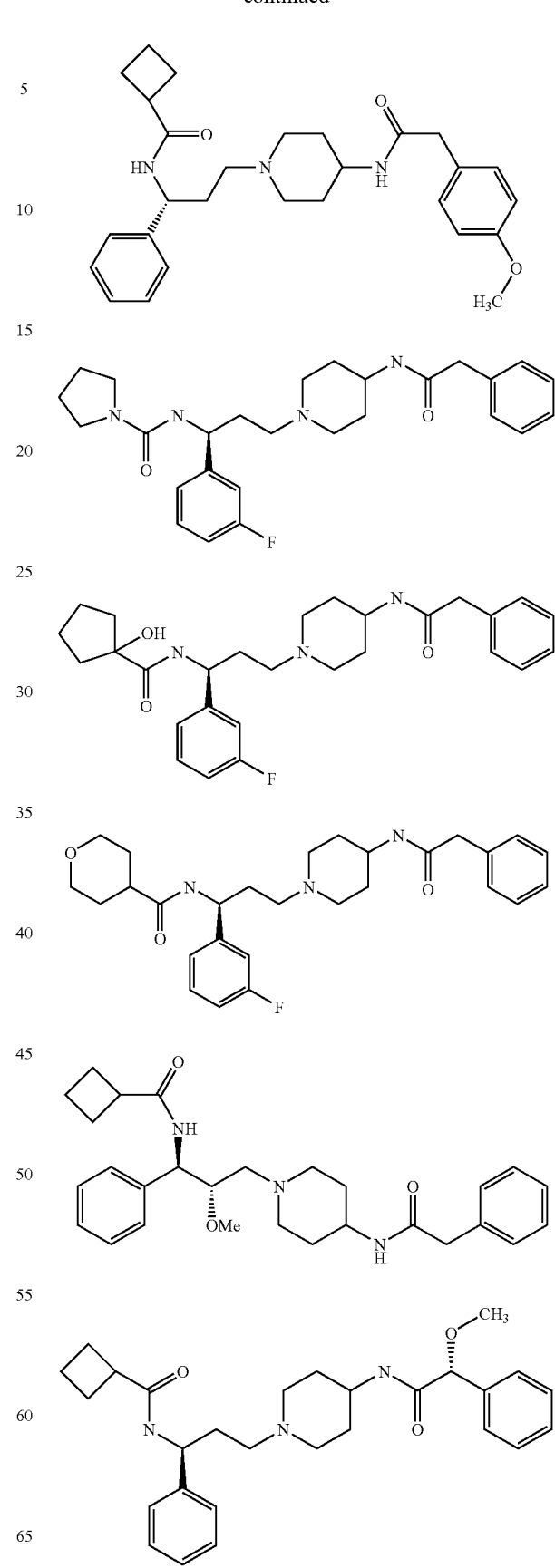

99
-continued
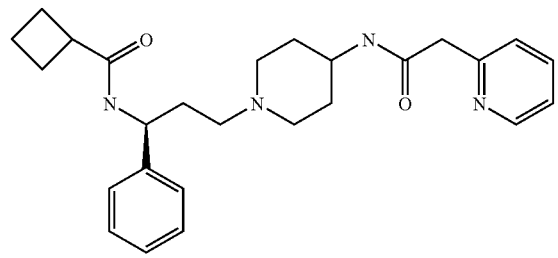
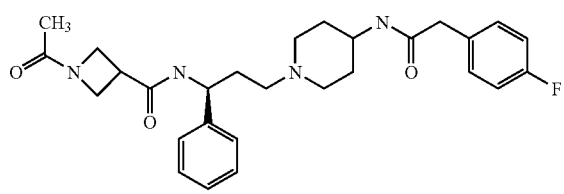
100
-continued
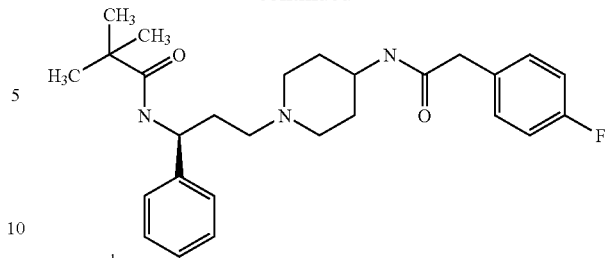
and
and the pharmaceutically acceptable salts thereof.
* * * * *